US010605799B2

(12) United States Patent
Chang et al.

(10) Patent No.: US 10,605,799 B2
(45) Date of Patent: Mar. 31, 2020

(54) SYSTEMS AND METHODS FOR DETECTING METAL ION CONCENTRATIONS IN SUBJECTS

(71) Applicant: The Regents of the University of California, Oakland, CA (US)

(72) Inventors: Christopher J. Chang, Berkeley, CA (US); Jeffrey R. Long, Oakland, CA (US); Sumin Lee, Berkeley, CA (US); Gokhan Barin, Albany, CA (US)

(73) Assignee: The Regents of The University of California, Oakland, CA (US)

( * ) Notice: Subject to any disclaimer, the term of this patent is extended or adjusted under 35 U.S.C. 154(b) by 87 days.

(21) Appl. No.: 15/593,117

(22) Filed: May 11, 2017

(65) Prior Publication Data
US 2018/0024112 A1    Jan. 25, 2018

Related U.S. Application Data

(60) Provisional application No. 62/337,627, filed on May 17, 2016.

(51) Int. Cl.
| | |
|---|---|
| *G01N 33/00* | (2006.01) |
| *G01N 33/487* | (2006.01) |
| *C22B 3/26* | (2006.01) |
| *G01N 33/84* | (2006.01) |
| *G01N 33/53* | (2006.01) |
| *B01J 20/30* | (2006.01) |
| *G01N 31/22* | (2006.01) |

(52) U.S. Cl.
CPC .... *G01N 33/48714* (2013.01); *B01J 20/3042* (2013.01); *C22B 3/0018* (2013.01); *G01N 31/22* (2013.01); *G01N 33/5306* (2013.01); *G01N 33/84* (2013.01); *B01D 2257/60* (2013.01)

(58) Field of Classification Search
CPC ............................................. G01N 33/48714
USPC ........................................................... 436/74
See application file for complete search history.

(56) References Cited

PUBLICATIONS

Afsana et al., 2014, Biosci. Biotechnol. Biochem 68, 584-592.
Ala et al., 2007, Lancet. 369, 397-408.
Alsbaiee et al., 2016, Nature 529, 190-194.
Aron et al., 2015, Acc. Chem. Res. 48, 2434-2442.
Babardo et al., Langmuir 2011, 27, 3451-3460.
Bandmann et al., 2015 Lancet 14, 103-113.
Bayramoğlu et al., 2003, Hazard. Mater. 101, 285-300.
Beatty et al., 1999, Ind. Eng. Chem. Res. 38, 4402-4408.
Ben and Qiu, 2013, CrystEngComm 15, 17-26.
(Continued)

*Primary Examiner* — Christopher Adam Hixson
*Assistant Examiner* — Emily R. Berkeley
(74) *Attorney, Agent, or Firm* — Morgan, Lewis & Bockius LLP

(57) ABSTRACT

A method of selective detection of a concentration of a metal ion species in a subject is provided in which a biofluid sample is obtained from the subject. The biofluid sample is exposed to a functionalized porous aromatic polymer. The polymer selectively captures and concentrates the metal ion species from the biofluid. Subsequently, the biofluid is washed from the polymer. The polymer is then exposed to a solution comprising a colorimetric indicator that extracts the metal ion species from the washed polymer thereby changing a color of the solution as a function of an amount of the metal ion species in the polymer. The concentration of the metal ion species in the subject is then spectroscopically determined from the color of the solution.

19 Claims, 46 Drawing Sheets

(56) References Cited

PUBLICATIONS

Ben et al., 2009, Angew. Chem. Int. Ed. 48, 9457-9460.
Bernardo et al., 1992, Inorg. Chem. 31, 191-198.
Burleigh et al., 2001, Separ. Sci. Technol. 36, 3395-3409.
Chandra et al., 2014, J. Am. Chem. Soc. 136, 6570-6573.
Colson et al., 2011, Science 332, 228-231.
Côte et al., 2005, Science 310, 1166-1170.
Cotruvo et al., 2015, J. Chem. Soc. Rev. 44, 4400-4414.
Davis and O'Halloran, 2008, Nat. Chem. Biol. 4, 148-151.
Ding and Wang, 2013, Chem. Soc. Rev. 42, 548-568.
Ding et al., 2016, J. Am. Chem. Soc. 138, 3031-3037.
Ding et al., J. Nutr. Biochem., Apr. 2011;22(4):301-310.
Dodani et al., 2011, J. Am. Chem. Soc. 133, 8606-8616.
Dodani et al., 2011, Proc. Natl. Acad. Sci. U.S.A. 108, 5980-5985.
Dodani et al., 2014, Proc. Natl. Acad. Sci. U.S.A. 111, 16280-16285.
Dogru and Bein, 2011, Nat. Nano. 6, 333-335.
Domaille et al., 2008, Nat. Chem. Biol. 4, 168-175.
Domaille et al., 2010, J. Am. Chem. Soc. 132, 1194-1195.
Ebraheem and Hamdi, 1997, React. Funct. Polym. 34, 5-10.
Eddaoudi et al., 2002, Science 295, 469-472.
Farkas et al., 1999, Polyhedron 18, 2391-2398.
Feng et al., 2004, Sep. Purif. Technol. 40, 61-67.
Feng et al., 2012, Chem. Soc. Rev. 41, 6010-6022.
Ferenci, 2006, Hum. Genet. 120, 151-159.
Gray et al., 2012, PloS One 7, e38327.
Hatcher et al., Future Med. Chem. Dec. 2009; 1(9): 1643-1670.
He et al., 2013, Am. Chem. Soc. 135, 7807-7810.
Hirayama et al., 2012, Proc. Natl. Acad. Sci. U.S.A. 109, 2228-2233.
Hong-Hermesdorf et al., 2014 Nat. Chem. Biol. 10, 1034-1042.
Huster, 2010, Best Practice & Research Clinical Gastroenterology 24, 531-539.
Jiang et al.al., 2007, Angew. Chem. Int. Ed. 46, 8574-8578.
Kim et al., 2012, Chem. Mater. 24, 2256-2264.
Kondo et al., 1997, Angew. Chem. Int. Ed. 36, 1725-1727.
Konstas et al., 2012, Angew. Chem., Int. Ed. 51, 6639-6642.
Kumar et al., 2007, Sep. Purif. Technol. 57, 47-56.
Langner and Denk, 2004, Virchows Arch 445, 111-118.
Lau et al., 2014, Chem. Mater. 27, 4756-4762.
Lech et al., 2007, Clin. Toxicol. 45, 688-694.
Lee et al., 2009, Chem. Soc. Rev. 38, 1450-1459.
Li et al., 1999, Nature 402, 276-279.
Li et al., 2009, Chem. Soc. Rev. 38, 1477-1504.
Li et al., 2014, J. Am. Chem. Soc. 136, 8654-8660.
Li et al., 2014, Nat. Commun. 5, 5537-5543.
Li et al., 2016, Chem. Sci. 7, 2138-2144.
Lu et al., 2010, Chem. Mater. 22, 5964-5972.
Lu et al., 2011, J. Am. Chem. Soc. 133, 18126-18129.
Lu et al., 2012, Angew. Chem. Int. Ed. 51, 7480-7484.
Ma et al., 2014, Polym. Chem. 5, 144-152.
Maekawa and Koshijima, 1990, J. Appl. Polym. Sci. 40, 1601-1613.
Miller et al., 2006, Nat. Protoc. 1, 824-827.
O'Connell et al., 2008, Biores. Tech. 99, 6709-6724.
Orena, 1986, Biochem. Biophys. Res. Commun. 139, 822-829.
Park et al., 2010, Dyes and Pigments 87, 49-54.
Petrić, 2004, Water Research 38, 1893-1899.
Que and Chang, 2006, J. Am. Chem. Soc. 128, 15942-15943.
Que and Chang, 2010, Chem. Soc. Rev. 39, 51-60.
Que et al., 2009, J. Am. Chem. Soc. 131, 8527-8536.
Que et al., 2010, Dalton Trans. 39, 469-476.
Que et al., 2012, Chem. Sci. 3, 1829-1834.
Ranganathan et al., 2011 Blood 118, 3146-3153.
Razmandeh et al., 2014, J. Diabetes. Metab. Disord. 13:43/1-43/6.
Say et al., 2005, Biores. Tech. 23, 313-322.
Shin et al., 2007, R. Adv. Funct. Mater. 17, 2897-2901.
Sumida et al., 2012, Chem. Rev. 112, 724-781.
Van Humbeck et al., 2014, J. Am. Chem. Soc. 136, 2432-2440.
Vanhoe, 1989, Anal. Chem. 61, 1851-1857.
Walshe, 2011, Q J Med. 104, 775-778.
Wang et al., 2015, ACS Appl. Mater. Interfaces 7, 2016-2024.
Witte et al., 2000, Free Radic. Biol. Med. 28, 693-700.
Wu et al., Analyst, 2016, 141, 243-250.
Yetisen et al., 2015, Anal. Chem. 87, 5101-5108.
Zeng et al., 2006, J. Am. Chem. Soc. 128, 10-11.
Zhou and Kitagawa, 2014, Chem. Soc. Rev. 43, 5415-5418.
Zhu et al., 2012, Talanta. 93, 55-61.

SYSTEMS AND METHODS FOR DETECTING METAL ION CONCENTRATIONS IN SUBJECTS

CROSS REFERENCE TO RELATED APPLICATION

This Application claims priority to U.S. Provisional Patent Application No. 62/337,627, entitled "Systems and Methods for Detecting Metal Ion Concentrations in Subjects," filed May 17, 2016, which is hereby incorporated by reference in its entirety.

STATEMENT OF GOVERNMENT RIGHTS

This invention was made with government support under Grant Number GM079465 awarded by the National Institutes of Health and Grant Number DE-SC0001015 awarded by the Department of Energy. The government has certain rights in the invention.

FIELD OF THE PRESENT DISCLOSURE

The present application relates to determining metal ion concentrations in subjects using a multi-dimensional polymer that can include recurring units of one or more structure.

BACKGROUND OF THE PRESENT DISCLOSURE

Metal ions such as copper are an essential element for human health (See, Lippard and Berg, *Principles of Bioinorganic Chemistry*, University Science Books, Mill Valley, Calif., which is hereby incorporated by reference). Enzymes harness the redox activity of copper to perform functions spanning energy generation, neurotransmitter and pigment synthesis, and epigenetic modification. On the other hand, misregulation of copper homeostasis is also connected to many diseases, including cancer (See, Brady et al., 2014, *Nature* 509, 492-496, which is hereby incorporated by reference) neurodegenerative Alzheimer's, Parkinson's, and Huntington's diseases (Que et al., 2008, *Chem. Rev.* 108, 1517-1549; and Barnham and Bush, 2014, *Chem. Soc. Rev.* 43, 6727-6749, each of which is hereby incorporated by reference), and genetic disorders such as Menkes and Wilson's diseases (Kaler, 2011, *Nat. Rev. Neurol.* 7, 15-29; Burkhead et al., 2011, *Biometals*, 24, 455-466; Merle et al., 2007, *Gut* 56, 115-120; Huster et al., 2006, *S. Am. J. Pathol.*, 168, 423-434, each of which is hereby incorporated by reference). Technologies that can monitor metal ion homeostasis may therefore serve as valuable diagnostic tools for such diseases and related conditions.

In one example of a copper-mediated disorder, Wilson's disease is caused by mutation of the gene that encodes the copper transporter ATP7B protein. Mutations in this protein may lead to hyperaccumulation of copper in the liver, brain, kidney, and cornea, which can result in lipid peroxidation and corresponding liver damage as well as neurologic and psychiatric abnormalities. See, Kaler, 2011, *Nat. Rev. Neurol.* 7, 15-29; Burkhead et al., 2011, *Biometals* 24, 455-466; Merle et al., 2007, *Gut* 56, 115-120; Huster et al., 2006, *Am. J. Pathol.* 168, 423-434; Ridge et al., 2008, *PLoS One* 3, e1378; Boal et al., 2009 *Chem. Rev.* 109, 4760-4779; Brewer, "*Wilson's disease A Clinician's Guide to Recognition, Diagnosis, and Management*, Springer Science+Business Media New York, 2001, Print, each of which is hereby incorporated by reference. Patients suffering from Wilson's disease also exhibit high urinary copper levels (>100 mg/day, compared to 20-40 mg/day in healthy individuals) and increased serum free copper levels (>25 µg/dL, compared to 11-25 µg/dL in healthy individuals). See Kaler, 2011, *Nat. Rev. Neurol.* 7, 15-29; Burkhead et al., 2011, *Biometals* 24, 455-466; Merle et al., 2007, *Gut* 56, 115-120; and Huster et al., 2006, *Am. J. Pathol.* 168, 423-434, each of which is hereby incorporated by reference. The source of this elevated copper is not sufficiently understood, but it is thought to derive from necrosis of damaged liver cells that are cleared through the blood stream. See, Ridge et al., 2008, *PLoS One* 3, e1378; and Boal and Rosenzweig, 2009, *Chem. Rev.* 109, 4760-4779, each of which is hereby incorporated by reference.

Wilson's disease is potentially fatal, although it is readily treated if diagnosed early in its development and before extensive tissue damage has occurred. Recognizing Wilson's disease is a challenge all its own, however, owing to a lack of targeted and readily implemented diagnostic tools. Magnetic resonance imaging (MRI) and electroencephalography (EEG) are two non-invasive techniques currently used to aid in Wilson's diagnosis. However, these techniques are not specific for Wilson's disease and instead serve primarily to identify secondary characteristics. While genetic tests can offer highly accurate diagnoses, over 300 different mutations for Wilson's disease are listed in the Human Genome Organization database and only a few are fully characterized or widespread. Thus, genetic tests based on selected exons are not globally applicable. See Huster, 2010, *Best Practice & Research Clinical Gastroenterology* 24, 531-539; Ala et al., 2007, *Lancet* 369, 397-408; Ferenci, 2006, *Hum. Genet.* 120, 151-159; and Bandmann et al., 2015, *Lancet* 14, 103-113, each of which is hereby incorporated by reference.

In contrast, non-invasive tests on biofluids such as urine and blood can alternatively provide an accurate diagnosis, although these methods can require cumbersome extraction procedures that include the concentration of urine collected over 24 hours or acid digestion of serum. Expensive characterization methods such as inductively coupled plasma mass spectrometry (ICP-MS) or atomic absorption spectroscopy (AAS) are then used for direct copper detection. See, Brewer, *Wilson's disease A Clinician's Guide to Recognition, Diagnosis, and Management*, Springer Science+Business Media New York, 2001, Print; Huster, 2010, *Best Practice & Research Clinical Gastroenterology* 24, 531-539; Ala et al., 2007, *Lancet* 369, 397-408; Ferenci, 2006, *Hum. Genet.* 120, 151-159; Bandmann et al., 2015 *Lancet* 14, 103-113; Orena, 1986, *Biochem. Biophys. Res. Commun.* 139, 822-829; and Malshe, 2011, *Q J Med.* 104, 775-778, each of which is hereby incorporated by reference.

SUMMARY

In exemplary embodiments, the present invention makes use of highly porous aromatic covalent framework (PAF) polymers, which are comparable to zeolites and metal-organic-framework (MOF) materials in terms of their porosity. Exemplary PAF polymers of the present invention are characterized by a rigid three-dimensional framework mainly comprised of aromatic rings. Exemplary frameworks are built up by polymerization of one monomer or copolymerization of more than one monomer. Typical reactions are C—C coupling reactions or addition reactions under ring formation conditions. Exemplary PAF polymers show water and temperature resistant behavior.

In various embodiments, the porous aromatic covalent framework polymer is characterized in that the polymer comprises at least a first aryl or heteroaryl monomer unit and at least a second aryl or heteroaryl monomer unit. The first and second monomer units each have different structures. Exemplary aryl or heteroaryl ring components of the first and second monomer are selected from phenyl, naphthyl, biphenyl, pyridyl, pyrimidinyl, pyridazinyl, pyrazinyl and triazinyl. The aryl and heteroaryl rings of the first monomer and the second monomer are independently selected, and they are optionally substituted at positions other than those positions through which polymerization to form the framework occurs.

One aspect of the present disclosure provides a method of selective detection of a concentration of a first metal ion (e.g., copper, iron, zinc, lead, cobalt) species in a subject. In the method, a biofluid sample (e.g., urine, serum, whole blood, saliva, tears, sweat, breast milk, mucus, blister fluid, cyst fluid, etc.) is obtained from the subject. The biofluid sample is exposed to a functionalized porous aromatic polymer (e.g., for 1 minute, 5 minutes, ten minutes, overnight). The functionalized porous aromatic polymer selectively captures and concentrates the first metal ion species from the biofluid sample.

The biofluid sample is then washed from the porous aromatic polymer. The washed functionalized porous aromatic polymer is then exposed to a solution comprising a colorimetric indicator that extracts the first metal ion species from the washed functionalized porous aromatic polymer thereby changing a color of the solution as a function of an amount of the first metal ion species in the washed functionalized porous aromatic polymer. In typical embodiments, the solution comprising a colorimetric indicator is colorless prior to exposure to the washed functionalized porous aromatic polymer and the metal ion in the polymer causes the solution to turn color. In this way, the concentration of the first metal ion species in the subject can be spectroscopically determined from the color of the solution.

In some embodiments, the first metal ion species is copper and the functionalized porous aromatic polymer is functionalized with an alkyl thioether, a dialkyl thioether, 2,5-dithiahexane, 3,4-dithiahexane, 4,5-dithiahexane, (2-methoxyethyl)(methyl)sulfane, (2-methoxyethyl)(methyl)sulfane, 3-(methylthio)propanoic acid, ethylglycine, N-hydroxy-2-(methylamino)acetamide, 2-thiopentane, N-hydroxyacetamide, or 2-methylhydrazine-1-carbothioamide.

In some embodiments, the first metal ion species is copper and the method further comprises pretreating the biofluid sample prior to the exposing b) with a chelator for a second metal ion species. In some embodiments the second metal ion species is iron and the chelator is acetohydroxamic acid, desferoxamine (DFO), 2,2'-bypyridyl, 1,10-phenantholine, or ethylenediaminetetraacetic acid (EDTA).

In some embodiments, the first metal ion species is copper and the functionalized porous aromatic polymer is formed from the monomer of Formulas (I), (II), (III) or (IV):

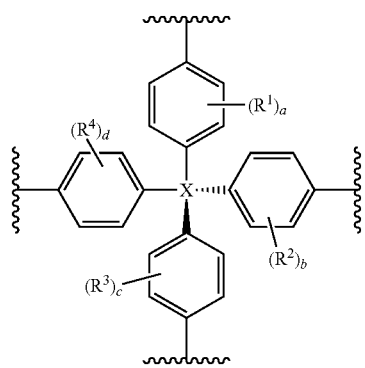

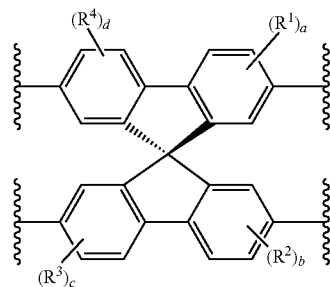

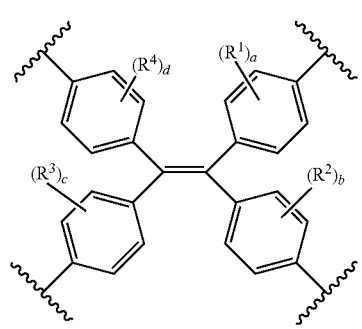

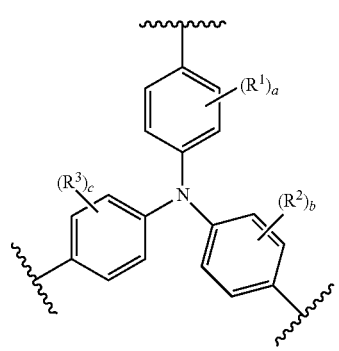

In such embodiments, X is selected from C, Si, and a three-dimensional polycyclic cycloalkyl moiety. Further, $R^1$, $R^2$, $R^3$ and $R^4$ are independently selected from an alkyl thioether, a dialkyl thioether, 2,5-dithiahexane, 3,4-dithiahexane, 4,5-dithiahexane, (2-methoxyethyl)(methyl)sulfane, (2-methoxyethyl)(methyl)sulfane, 3-(methylthio)propanoic acid, ethylglycine, N-hydroxy-2-(methylamino)acetamide, 2-thiopentane, N-hydroxyacetamide and 2-methylhydrazine-1-carbothioamide. Also, the indeces a, b, c and d are members independently selected from the integers 0, 1, 2, 3, and 4, such that when a, b, c, or d is greater than 1, each $R^1$, $R^2$, $R^3$ and $R^4$, respectively, is independently selected.

In some embodiments, the first metal ion species is copper, and the functionalized porous aromatic polymer is a copolymer formed from a first monomer of Formula (I), (II), (III) or (IV) and a second monomer according to Formula (V):

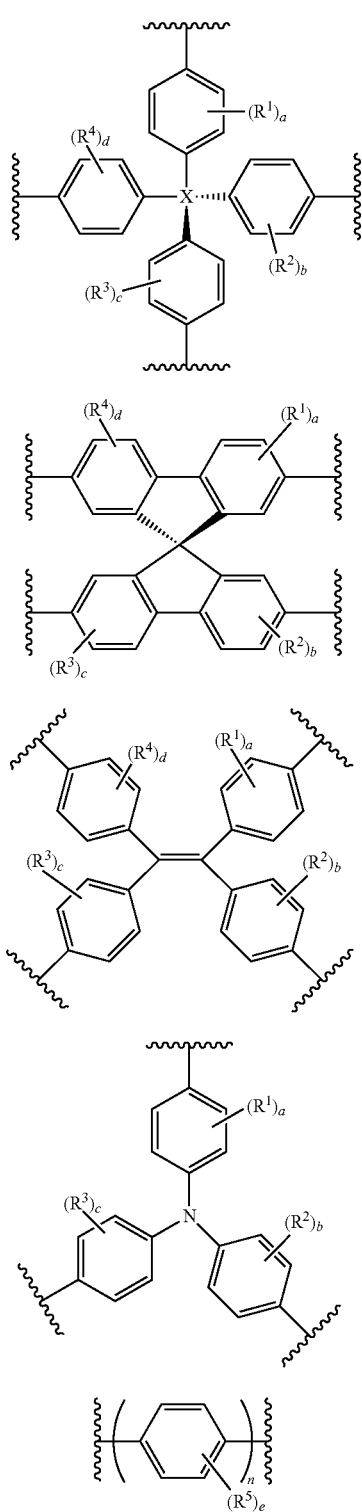

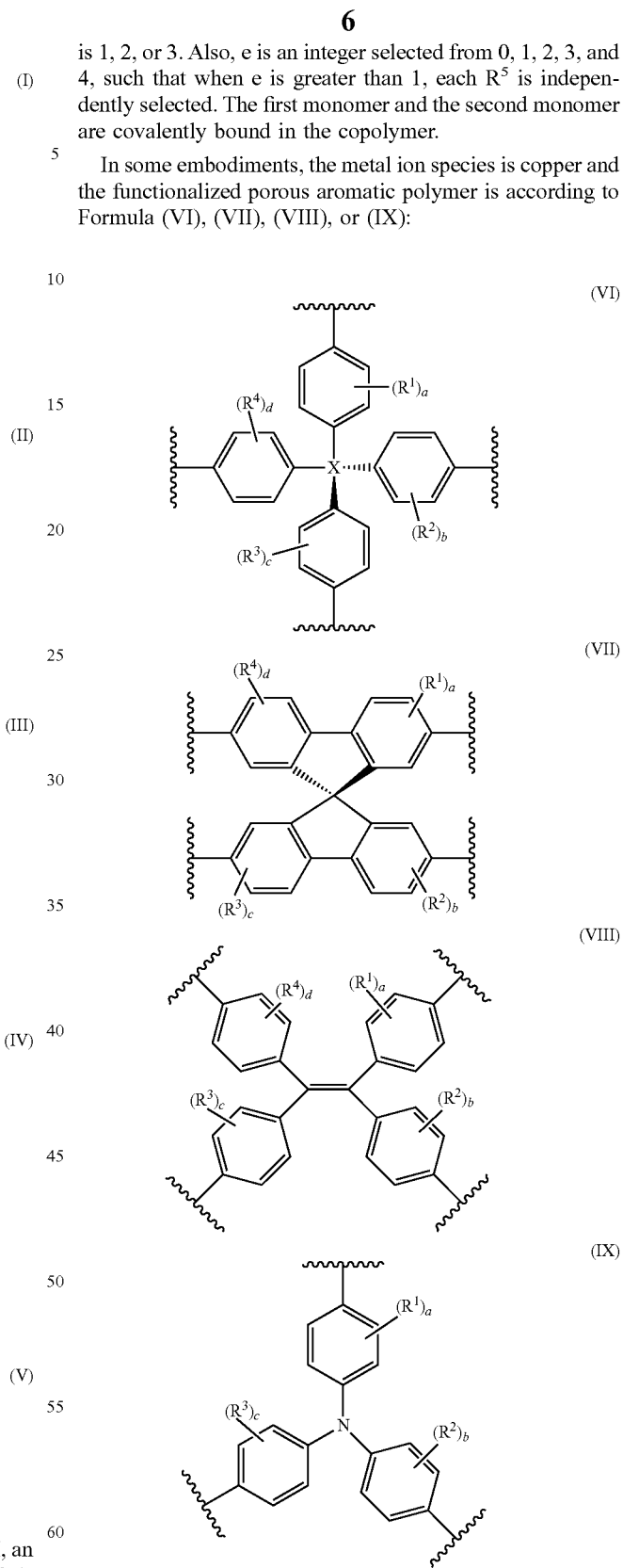

is 1, 2, or 3. Also, e is an integer selected from 0, 1, 2, 3, and 4, such that when e is greater than 1, each $R^5$ is independently selected. The first monomer and the second monomer are covalently bound in the copolymer.

In some embodiments, the metal ion species is copper and the functionalized porous aromatic polymer is according to Formula (VI), (VII), (VIII), or (IX):

In such embodiments, $R^5$ is a member selected from H, an alkyl thioether, a dialkyl thioether, 2,5-dithiahexane, 3,4-dithiahexane, or 4,5-dithiahexane, (2-methoxyethyl)(methyl)sulfane, (2-methoxyethyl)(methyl)sulfane, 3-(methylthio)propanoic acid, ethylglycine, N-hydroxy-2-(methylamino)acetamide, 2-thiopentane, N-hydroxyacetamide and 2-methylhydrazine-1-carbothioamide. Further, n is 1, 2, or 3.

In such embodiments, X is selected from C, Si, and a three-dimensional polycyclic cycloalkyl moiety. $R^1$, $R^2$, $R^3$ and $R^4$ are each independently selected from Formula (X) or (XI)

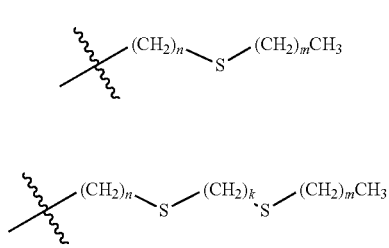
(X)

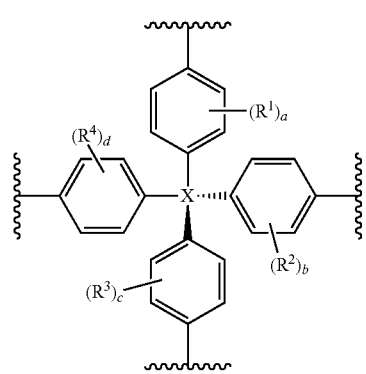
(XI)

Further, n is a zero or positive integer, m is zero or a positive integer, and k is a positive integer. Also, the indeces a, b, c and d are members independently selected from the integers 0, 1, 2, 3, and 4, such that when a, b, c, or d is greater than 1, each $R^1$, $R^2$, $R^3$ and $R^4$, respectively, is independently selected.

In some embodiments, the first metal ion species is copper and the functionalized porous aromatic polymer is a copolymer formed from a first monomer of Formula (VI), (VII), (VIII) or (IX) and a second monomer of Formula (XII):

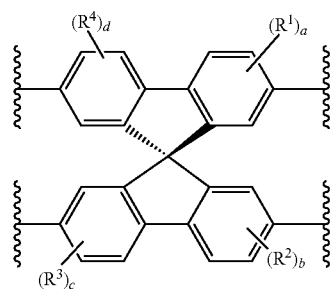
(VI)

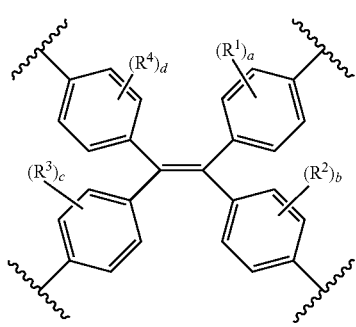
(VII)

(VIII)

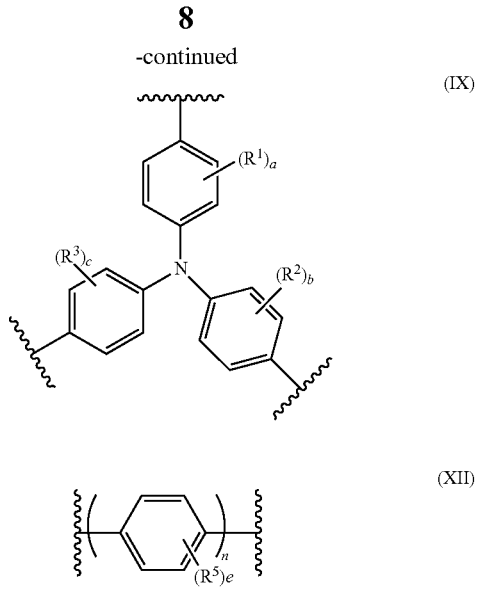
(IX)

(XII)

In such embodiments, $R^5$ is a member selected from H, an alkyl thioether, a dialkyl thioether, 2,5-dithiahexane, 3,4-dithiahexane, 4,5-dithiahexane, (2-methoxyethyl)(methyl)sulfane, (2-methoxyethyl)(methyl)sulfane, 3-(methylthio)propanoic acid, ethylglycine, N-hydroxy-2-(methylamino)acetamide, 2-thiopentane, N-hydroxyacetamide and 2-methylhydrazine-1-carbothioamide. Further, e is an integer selected from 0, 1, 2, 3, and 4, such that when e is greater than 1, each $R^5$ is independently selected. The first monomer and the second monomer are covalently bound in the copolymer.

In some embodiments, the first metal ion species is copper, and the colorimetric indicator comprises 8-hydroxyquinoline, 2,2'-bipyridine, or 1,10-phenanthroline.

In some embodiments, the first metal ion species is copper and the spectroscopically determination described herein determines whether the subject has Wilson's disease from the color of the solution.

In some embodiments, the first metal ion species is iron, and the functionalized porous aromatic polymer is according to Formula (XIII), (XIV), (XV), or (XVI):

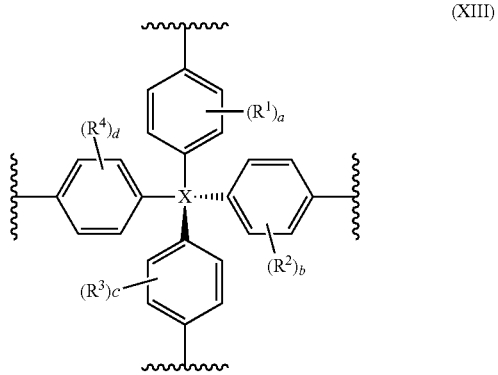
(XIII)

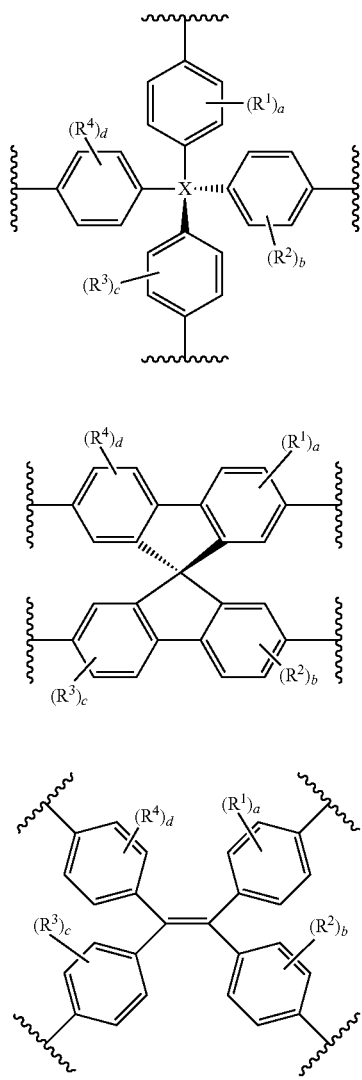

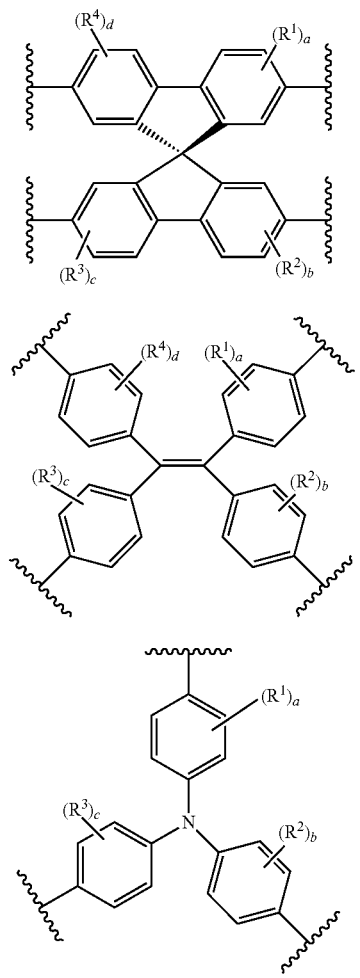

In such embodiments, X is selected from C, Si, and a three-dimensional polycyclic cycloalkyl moiety. Further, $R^1$, $R^2$, $R^3$ and $R^4$ are independently selected from Formula (XVII) or (XVIII)

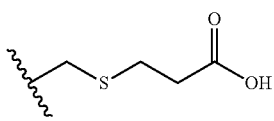

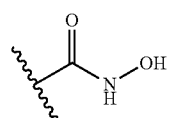

Further, the indeces a, b, c and d are members independently selected from the integers 0, 1, 2, 3, and 4, such that when a, b, c, or d is greater than 1, each $R^1$, $R^2$, $R^3$ and $R^4$, respectively, is independently selected.

In some embodiments, the first metal ion species is iron, and the functionalized porous aromatic polymer is a copolymer formed from a first monomer of Formula (XIII), (XIV), (XV) or (XVI) and a second monomer according to Formula (XIX):

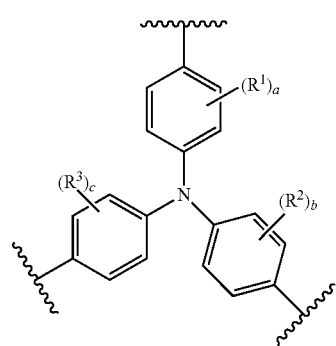

In such embodiments, $R^5$ is independently selected from Formula (XX) or (XXI):

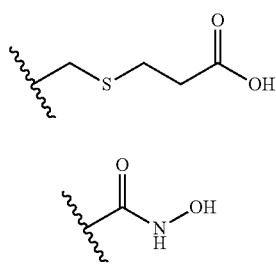

(XX)

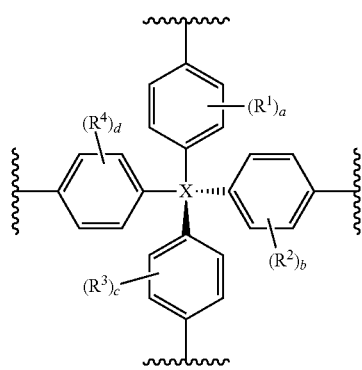

(XXIII)

(XXI)

Further, e is an integer selected from 0, 1, 2, 3, and 4, such that when e is greater than 1, each $R^5$ is independently selected. The first monomer and the second monomer are covalently bound in the copolymer.

In some embodiments, the first metal ion species is iron or copper, and the colorimetric indicator is according to Formula (XXII):

In some such embodiments, X is carbon. Further, $R^1$, $R^2$, $R^3$ and $R^4$ are independently selected from Formula (XXIV) or (XXV):

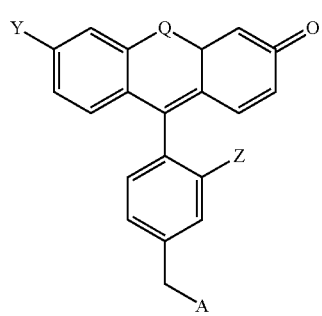

(XXII)

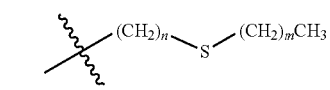

(XXIV)

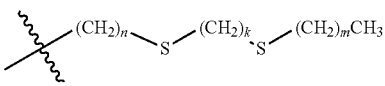

(XXV)

In such embodiments, Q is O, Si(Me)$_2$, or C(Me)$_2$. Further, Y is —OH, morpholine, piperidine, pyrrolidine, or a piperazine derivative. Further still, Z is —CH$_3$, —CF$_3$, or —COOH, and A is a metal ion acceptor. For example, in some embodiments, the first metal ion is copper and A is 3, 6, 12, 15-tetrathia-9-monoazaheptadecane.

Another aspect of the present disclosure provides a method of detecting copper in a subject. The method comprises obtaining a biological fluid (e.g., urine, serum, whole blood, saliva, tears, sweat, breast milk, mucus, blister fluid, or cyst fluid) from the subject. The biological fluid is exposed to a functionalized porous aromatic polymer, where the functionalized porous aromatic polymer selectively captures and concentrates copper from the biological fluid. The biological fluid is then washed from the functionalized porous aromatic polymer and the polymer is then exposed to a solution comprising a colorimetric indicator that extracts the copper from the washed functionalized porous aromatic polymer thereby changing a color of the solution as a function of an amount of the copper in the washed functionalized porous aromatic polymer. After this exposing step, the concentration of the copper in the subject is spectroscopically determined from the color of the solution by measuring a characteristic absorption wavelength of a complex between copper and the colorimetric indicator.

In some such embodiments, the functionalized porous aromatic polymer is formed from the monomer of Formula (XXIII):

Here, n is 1, 2 or 3 and m is 1 or 2, whereas k is 1, 2 or 3. Further, the indeces a, b, c and d are members independently selected from the integers 0, 1, 2, 3, and 4, such that when a, b, c, or d is greater than 1, each $R^1$, $R^2$, $R^3$ and $R^4$, respectively, is independently selected. In some embodiments, the method further comprises pretreating the biofluid sample with a chelator for iron (e.g., acetohydroxamic acid, desferoxamine (DFO), or 2,2'-bypyridyl) prior to the exposing the biofluid with the polymer.

Another aspect of the present disclosure provides a functionalized porous aromatic polymer according to Formula (XXVI), where

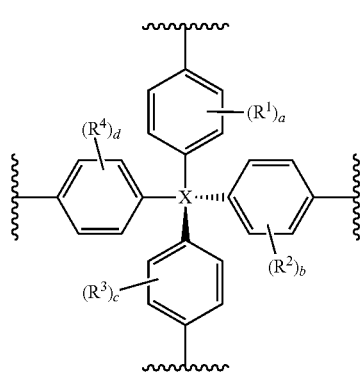

(XXVI)

In such embodiments, X is carbon. Further, $R^1$, $R^2$, $R^3$ and $R^4$ are independently selected from Formula (XXVII) or (XXVIII):

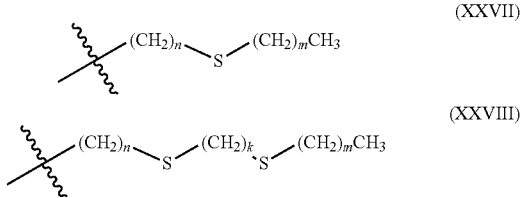

(XXVII)

(XXVIII)

In such embodiments, n is 1, 2 or 3. Further, m is 1 or 2. Further still, k is 1, 2 or 3, and the indeces a, b, c and d are members independently selected from the integers 0, 1, 2, 3, and 4, such that when a, b, c, or d is greater than 1, each $R^1$, $R^2$, $R^3$ and $R^4$, respectively, is independently selected.

Another aspect of the present disclosure provides the functionalized porous aromatic polymer according to formula (XXVI) reacted with copper in a biofluid sample collected from a subject.

As described below, the present disclosure provides compounds, devices, systems and methods based on porous aromatic polymers with multiple functional groups present in a spatial arrangement that leads to cooperative reactivity of these functional groups in the binding of metal ions such as copper and iron.

BRIEF DESCRIPTION OF THE DRAWINGS

FIG. 19A Iron uptake (10 ppm in 100 mM HEPES buffer, pH 6.7, light gray bar) showed a decrease (dark gray bar) upon addition of copper ions (10 ppm). FIG. 19B Copper uptake (10 ppm, light gray bar) showed a slight decrease (dark gray bar) after adding additional iron ions (10 ppm).

DETAILED DESCRIPTION OF THE INVENTION

I. Introduction

Figure 1A:
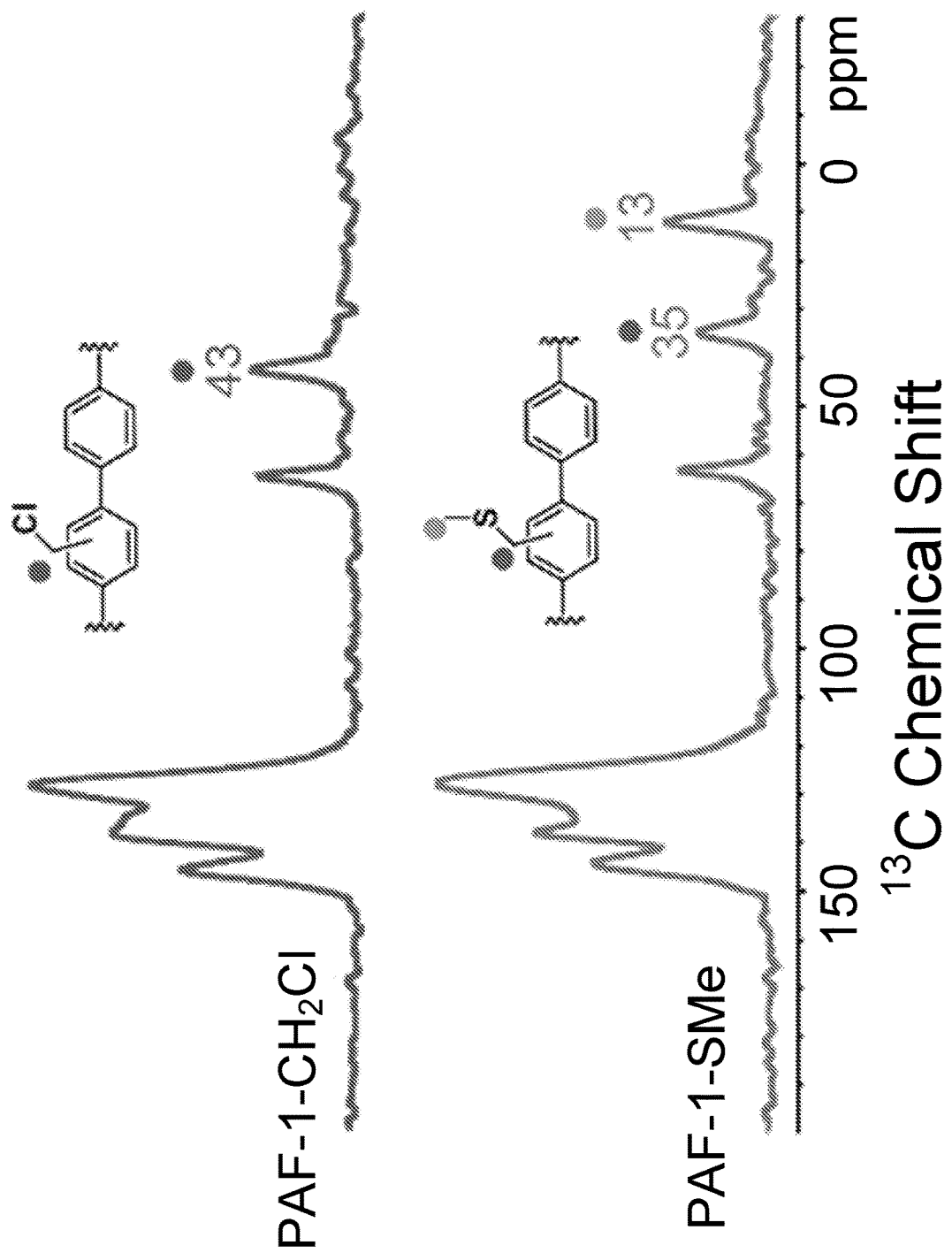
FIG. 1A illustrates Solid-state $^{13}C$ NMR spectra of PAF-1-CH2Cl and PAF-1-SMe.
Figure 1B:
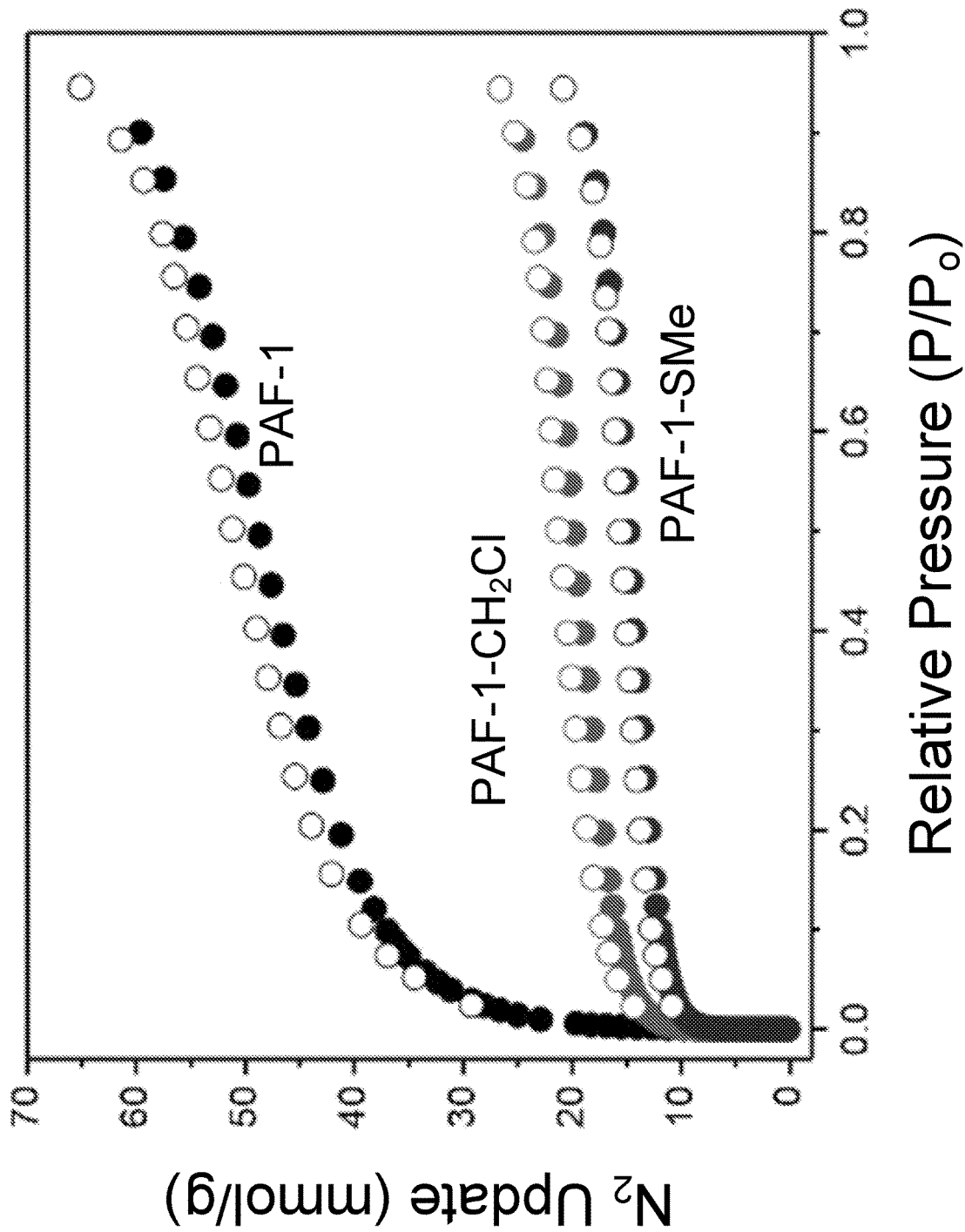
FIG. 1B illustrates $N_2$ sorption isotherms of PAF-1, PAF-1-CH2Cl, and PAF-1-SMe at 77 K. Closed and open symbols represent adsorption and desorption branches, respectively.

Given the difficulty in assaying for metal ions, such as copper, discussed above, we envisioned an alternative approach that would enable metal ion detection and readout of corresponding levels directly from biofluids as well as environmental samples in a colorimetric assay, thereby circumventing extensive sample processing.

This strategy relies on the utilization of solid-state adsorbents to capture metal ions such as copper selectively and efficiently from the biosample of interest followed by treatment with a colorimetric agent to quantify metal ion levels.

This divide-and-conquer approach is broadly applicable to detection of many biological and environmental analytes.

In this context, porous polymers represent a promising class of such adsorbents for this purpose, owing to their high thermal and chemical stability, particularly to aqueous media, as well as high surface area, permanent porosity, and diversity of functional groups. See, for example, Cote et al., 2005, *Science* 310, 1166-1170; Jiang et alai, 2007, *Angew. Chem. Int. Ed.* 46, 8574-8578; Dogru and Bein, 2011, *Nat. Nano.* 6, 333-335; Colson et al., 2011, *Science* 332, 228-231; Chandra et al., 2014, *J. Am. Chem. Soc.* 136, 6570-6573; Ding and Wang, 2013, *Chem. Soc. Rev.* 42, 548-568; Feng et al., 2012, *Chem. Soc. Rev.* 41, 6010-6022; Li et al., 1999, *Nature* 402, 276-279; Kondo et al., 1997, *Angew. Chem. Int. Ed.* 36, 1725-1727; Eddaoudi et al., 2002, *Science* 295, 469-472; Zhou and Kitagawa, 2014, *Chem. Soc. Rev.* 43, 5415-5418; Sumida et al., 2012, *Chem. Rev.* 112, 724-781; Li et al., 2009, *Chem. Soc. Rev.* 38, 1477-1504; Lee et al., 2009, *Chem. Soc. Rev.* 38, 1450-1459; Ben et al., 2009, *Angew. Chem. Int. Ed.* 48, 9457-9460; Ben and Qiu, 2013, *CrystEngComm* 15, 17-26; Lu et al., 2011, *J. Am. Chem. Soc.* 133, 18126-18129; Lu et al., 2012, *Angew. Chem. Int. Ed.* 51, 7480-7484; Konstas et al., 2012, *Angew. Chem., Int. Ed.* 51, 6639-6642; Ma et al., 2014, *Polym. Chem.* 5, 144-152; Van Humbeck et al., 2014, *J. Am. Chem. Soc.* 136, 2432-2440; Lau et al., 2014, *Chem. Mater.* 27, 4756-4762; Li et al., 2014, *J. Am. Chem. Soc.* 136, 8654-8660; and Li et al., 2016, *Chem. Sci.* 7, 2138-2144, each of which is hereby incorporated by reference.

The canonical material porous aromatic framework (PAF)-1 in particular exhibits a high Brunauer-Emmett-Teller (BET) surface area (up to 5600 $m^2/g$) (See, for example, Ben et al., 2009, *Angew. Chem. Int. Ed.* 48, 9457-9460; and Ben and Qiu, S. CrystEngComm 2013, 15, 17-26, each of which is hereby incorporated by reference) and is readily modified post-synthetically to introduce a variety of desired chemical functionalities in a dense and accessible manner. See, Lu et al., 2011, *Am. Chem. Soc.* 133, 18126-18129; Lu et al., 2012, *Angew. Chem. Int. Ed.* 51, 7480-7484; Konstas et al., 2012, *Angew. Chem., Int. Ed.* 51, 6639-6642; Ma et al., 2014 *Polym. Chem.* 5, 144-152; Van Humbeck et al., 2014, *J. Am. Chem. Soc.* 136, 2432-2440; Lau et al., 2014, *Chem. Mater.* 27, 4756-4762; Li et al., 2014, 1 *Am. Chem. Soc.* 136, 8654-8660; and Li et al., 2016, *Chem. Sci.* 7, 2138-2144, each of which is hereby incorporated by reference. Indeed, a thiol (—SH) functionalized PAF-1 was recently reported as a platform for the capture of the toxic heavy metal mercury in water treatment. See Li et al., 2014, *Nat. Commun* 5537-5543, which is hereby incorporated by reference.

We sought to prepare a new PAF-1 analog with copper-selective appendages to allow for specific and sensitive capture of this naturally occurring biological metal from biofluid samples. Inspection of copper binding sites in cytosolic metalloregulatory proteins show that they are dominated by histidine, cysteine, and methionine residues. See, Davis and O'Halloran, 2008, *Nat. Chem. Biol.* 4, 148-151 and Bernardo et al., 1992, *Inorg. Chem.* 31, 191-198, hereby incorporated by reference, which feature —NH, —SH, and thioether (—SMe) functionalities, respectively. We reasoned that thioethers are less redox-active and pH-independent compared to their thiol counterparts and are also advantageous over nitrogen-containing binding moieties, such as histidine, to achieve high copper selectivity over other biologically relevant cations like Fe(II) and Zn(II).

Figure 6:
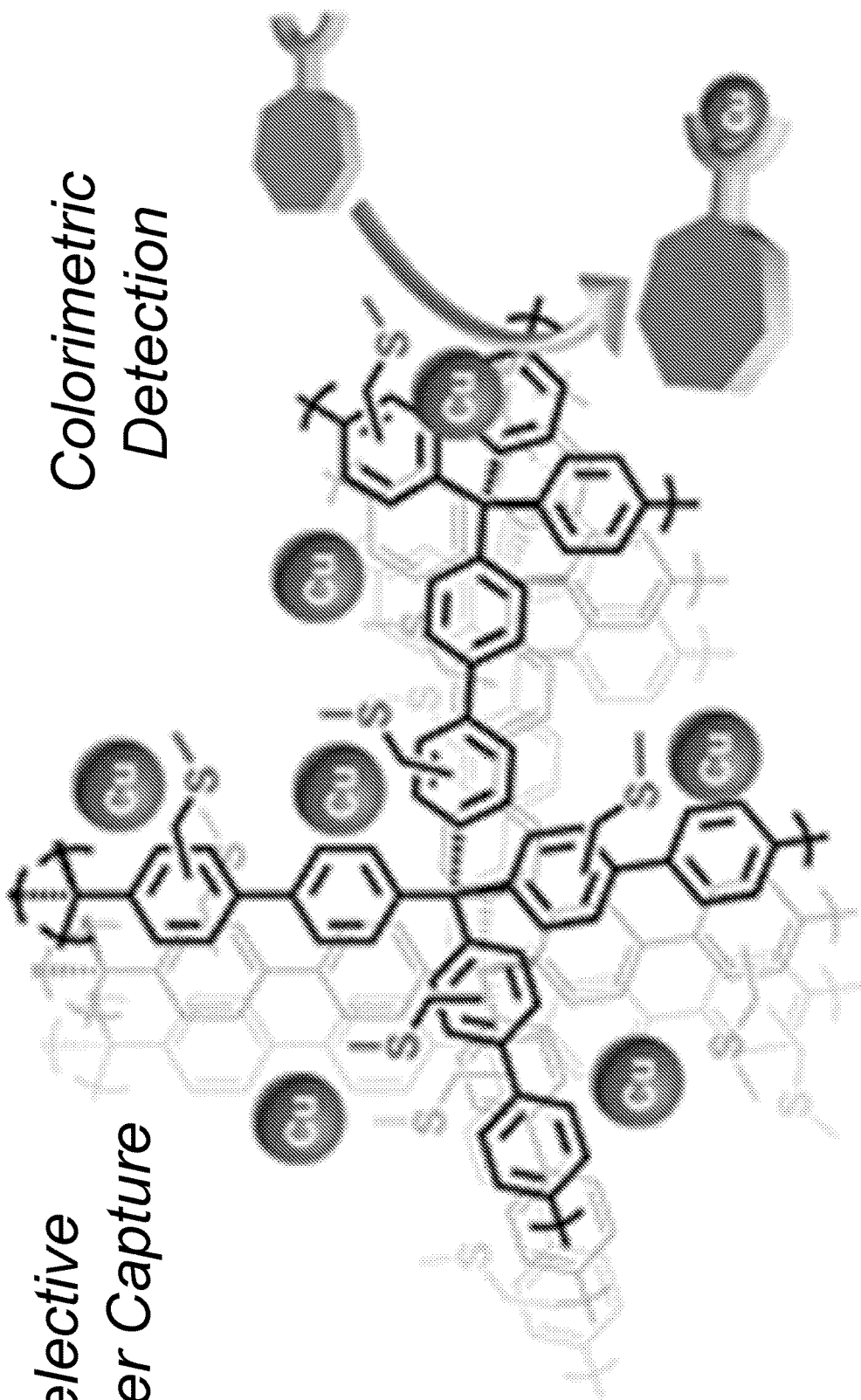
FIG. 6 illustrates a copper detection assay with PAF-1-SMe as a selective copper capture material coupled to a colorimetric indicator for detection and regeneration, in accordance with an embodiment of the present disclosure.

Indeed, our laboratory has previously reported synthetic fluorescent (Aron et al., 2015, *Acc. Chem. Res.* 48, 2434-2442; Cotruvo et al., 2015, *J. Chem. Soc. Rev.* 44, 4400-4414; Domaille et al., 2008, *Nat. Chem. Biol.* 4, 168-175; Zeng et al., 2006, *J. Am. Chem. Soc.* 128, 10-11; Miller et al., 2006, *Nat. Protoc.* 1, 824-827; Domaille et al., 2010, 1 *Am. Chem. Soc.* 132, 1194-1195; Dodani et al., 2011, *Proc. Natl. Acad. Sci. U.S.A.* 108, 5980-5985; Dodani et al., 2011, *J. Am. Chem. Soc.* 133, 8606-8616; Hirayama et al., 2012, *Proc. Natl. Acad. Sci. U.S.A.* 109, 2228-2233; Dodani et al., 2014, *Proc. Natl. Acad. Sci. U.S.A.* 111, 16280-16285; Hong-Hermesdorf et al., 2014 *Nat. Chem. Biol.* 10, 1034-1042, each of which is hereby incorporated by reference) and MRI copper probes (Que and Chang, 2010, *Chem. Soc. Rev.* 39, 51-60; Que and Chang, 2006, 1 *Am. Chem. Soc.* 128, 15942-15943; Que et al., 2009, 1 *Am. Chem. Soc.* 131, 8527-8536; Que et al., 2010, *Dalton Trans.* 39, 469-476; and Que et al., 2012, *Chem. Sci.* 3, 1829-1834, hereby incorporated by reference) with thioether rich receptors, which revealed high selectivity towards copper ions in biological samples from cells to tissues to whole organisms. We now report the thioether-functionalized solid-state porous polymer PAF-1-SMe, an adsorbent that is selective for the capture and concentration of copper from complex biofluid samples. In conjunction with a colorimetric reagent for assessing copper levels, we further demonstrate that PAF-1-SMe can be used in an assay to selectively adsorb copper and detect elevated copper levels in biosamples (FIG. 6). This work establishes the potential utility of porous polymeric materials for non-invasive diagnostic applications, without the need for extensive sample processing or complex and expensive instrumentation.

As such, the present invention provides a method of selective detection of a concentration of a metal ion species in a subject is provided in which a biofluid sample is obtained from the subject. The biofluid sample is exposed to a functionalized porous aromatic polymer. The polymer selectively captures and concentrates the metal ion species from the biofluid. Subsequently, the biofluid is washed from the polymer. The polymer is then exposed to a solution comprising a colorimetric indicator that extracts the metal ion species from the washed polymer thereby changing a color of the solution as a function of an amount of the metal ion species in the polymer. The concentration of the metal ion species in the subject is then spectroscopically determined from the color of the solution.

Before the invention is described in greater detail, it is to be understood that the invention is not limited to particular embodiments described herein as such embodiments may vary. It is also to be understood that the terminology used herein is for the purpose of describing particular embodiments only, and the terminology is not intended to be limiting. The scope of the invention will be limited only by the appended claims. Unless defined otherwise, all technical and scientific terms used herein have the same meaning as commonly understood by one of ordinary skill in the art to which this invention belongs. Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention. Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number, which, in the context in which it is presented, provides the substantial equivalent of the specifically recited number. All publications, patents, and patent applications cited in this specification are incorporated herein by reference to the same extent as if each individual publication, patent, or patent application were specifically and individually indicated to be incorporated by reference. Furthermore, each cited publication, patent, or patent application is incorporated herein by reference to disclose and describe the subject matter in connection with which the publications are cited. The citation of any publication is for its disclosure prior to the filing date and should not be construed as an admission that the invention described herein is not entitled to antedate such publication by virtue of prior invention. Further, the dates of publication provided might be different from the actual publication dates, which may need to be independently confirmed.

It is noted that the claims may be drafted to exclude any optional element. As such, this statement is intended to serve as antecedent basis for use of such exclusive terminology as "solely," "only," and the like in connection with the recitation of claim elements, or use of a "negative" limitation. As will be apparent to those of skill in the art upon reading this disclosure, each of the individual embodiments described and illustrated herein has discrete components and features which may be readily separated from or combined with the features of any of the other several embodiments without departing from the scope or spirit of the invention. Any recited method may be carried out in the order of events recited or in any other order that is logically possible. Although any methods and materials similar or equivalent to those described herein may also be used in the practice or testing of the invention, representative illustrative methods and materials are now described.

In describing the present invention, the following terms will be employed, and are defined as indicated below.

II. Definitions

Where substituent groups are specified by their conventional chemical formulae, written from left to right, the structures optionally also encompass the chemically identical substituents, which would result from writing the structure from right to left, e.g., —$CH_2O$— is intended to also optionally recite —$OCH_2$—.

The term "alkyl," by itself or as part of another substituent, means, unless otherwise stated, a straight or branched chain, or cyclic hydrocarbon radical, or combination thereof, which may be fully saturated, mono- or polyunsaturated and can include di-, tri- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to optionally include those derivatives of alkyl defined in more detail below, such as "heteroalkyl." Alkyl groups that are limited to hydrocarbon groups are termed "homoalkyl". Exemplary alkyl groups include the monounsaturated $C_{9-10}$, oleoyl chain or the diunsaturated $C_{9-10, 12-13}$ linoeyl chain.

The term "alkylene" by itself or as part of another substituent means a divalent radical derived from an alkane, as exemplified, but not limited, by —$CH_2CH_2CH_2CH_2$-, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The terms "aryloxy" and "heteroaryloxy" are used in their conventional sense, and refer to those aryl or heteroaryl groups attached to the remainder of the molecule via an oxygen atom.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —$CO_2$R'— represents both —C(O)OR' and —OC(O)R'.

The terms "cycloalkyl" and "heterocycloalkyl," by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Further exemplary cycloalkyl groups include steroids, e.g., cholesterol and its derivatives. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl substituent groups (or rings) that contain from one to four heteroatoms selected from N, O, S, Si and B, wherein the nitrogen and sulfur atoms are optionally oxidized, and the nitrogen atom(s) are optionally quaternized. An exemplary heteroaryl group is a six-membered azine, e.g., pyridinyl, diazinyl and triazinyl. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes aryl, heteroaryl and heteroarene rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl, and "heteroaryl") are meant to optionally include both substituted and unsubstituted forms of the indicated species. Exemplary substituents for these species are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: H, substituted or unsubstituted aryl, substituted or unsubstituted heteroaryl, substituted or unsubstituted heterocycloalkyl, —OR', =O, =NR', =N—OR', —NR'R", —SR', halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —$NO_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like). These terms encompass groups considered exemplary "alkyl group substituents", which are components of exemplary "substituted alkyl" and "substituted heteroalkyl" moieties.

Similar to the substituents described for the alkyl radical, substituents for the aryl heteroaryl and heteroarene groups are generically referred to as "aryl group substituents." The substituents are selected from, for example: groups attached to the heteroaryl or heteroarene nucleus through carbon or a heteroatom (e.g., P, N, O, S, Si, or B) including, without limitation, substituted or unsubstituted alkyl, substituted or unsubstituted aryl, substituted or unsubstituted heteroaryl, substituted or unsubstituted heterocycloalkyl, —OR', =O, =NR', =N—OR', —NR'R", —SR', -halogen, —SiR"R"', —OC(O)R', —C(O)R', —CO$_2$R', —CONR'R", —OC(O)NR'R", —NR" C(O)R', —NR'—C(O)NR"R'", —NR" C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system. Each of the above-named groups is attached to the heteroarene or heteroaryl nucleus directly or through a or a heteroatom (e.g., P, N, O, S, Si, or B); and where R', R", R"' and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R"' and R"" groups when more than one of these groups is present.

Two of the substituents on adjacent atoms of the aryl, heteroarene or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl, heteroarene or heteroaryl ring may optionally be replaced with a substituent of the formula —(CRR')$_s$—X—(CR"R"')$_d$—, where s and d are independently integers of from 0 to 3, and X is —O—, —NR'—, —S—, —S(O)—, —S(O)$_2$—, or —S(O)$_2$NR'—. The substituents R, R', R" and R"' are preferably independently selected from hydrogen or substituted or unsubstituted (C$_1$-C$_6$)alkyl. These terms encompass groups considered exemplary "aryl group substituents", which are components of exemplary "substituted aryl" "substituted heteroarene" and "substituted heteroaryl" moieties.

As used herein, the term "acyl" describes a substituent containing a carbonyl residue, C(O)R. Exemplary species for R include H, halogen, substituted or unsubstituted alkyl, substituted or unsubstituted aryl, substituted or unsubstituted heteroaryl, and substituted or unsubstituted heterocycloalkyl.

As used herein, the term "fused ring system" means at least two rings, wherein each ring has at least 2 atoms in common with another ring. "Fused ring systems" may include aromatic as well as non-aromatic rings. Examples of "fused ring systems" are naphthalenes, indoles, quinolines, chromenes and the like.

As used herein, the term "heteroatom" includes oxygen (O), nitrogen (N), sulfur (S) and silicon (Si), boron (B) and phosphorous (P).

The symbol "R" is a general abbreviation that represents a substituent group that is selected from H, substituted or unsubstituted alkyl, substituted or unsubstituted heteroalkyl, substituted or unsubstituted aryl, substituted or unsubstituted heteroaryl, and substituted or unsubstituted heterocycloalkyl groups.

The compounds disclosed herein may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

The term "salt(s)" includes salts of the compounds prepared by the neutralization of acids or bases, depending on the particular ligands or substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of base addition salts include sodium, potassium, calcium, ammonium, organic amino, or magnesium salt, or a similar salt. Examples of acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids, and the like, as well as the salts derived from relatively nontoxic organic acids like acetic, propionic, isobutyric, butyric, maleic, malic, malonic, benzoic, succinic, suberic, fumaric, lactic, mandelic, phthalic, benzenesulfonic, p-tolylsulfonic, citric, tartaric, methanesulfonic, and the like. Certain specific compounds of the present invention contain both basic and acidic functionalities that allow the compounds to be converted into either base or acid addition salts. Hydrates of the salts are also included.

As used herein, the term "active porous aromatic polymer" refers to a polymer of the invention that includes one or more Brønsted acid moiety available for binding to a nitrogenous species.

"Nitrogenous species," as this term is used refers to basic nitrogen-containing species such as ammonia and organic amines.

"—COOH" is meant to optionally include —C(O)O$^-$ and —C(O)O$^-$X$^+$, wherein X$^+$ is a cationic counter-ion. Likewise, a substituent having the formula —N(R)(R) is meant to optionally include —N$^+$H(R)(R) and —N$^+$H(R)(R)Y$^-$, wherein Y$^-$ represents an anionic counter-ion. Exemplary polymers of the invention include a protonated carboxylic moiety (COOH). Exemplary polymers of the invention include a deprotonated carboxylic moiety (COO$^-$). Various polymers of the invention include both a protonated carboxylic moiety and a deprotonated carboxylic moiety.

The terms "average diameter of the pore," "average diameter of the pore opening" or any grammatical variation thereof, refer to the pore size of a polymer of the invention. Pore sizes can, for example, be determined using nitrogen adsorption isotherms, microscopy or porosimetry.

The pores of the polymer can have any useful size. In a typical polymer, the average pore size is equal to or smaller than the nanoparticles, described herein below. The nominal pore size is typically measured in angstroms ($10^{-10}$ m, Å). In one example, the average diameter of the polymer pores is between about 5 and about 5000 Å. In another example, the volume average diameter of the polymer pores is between about 5 and about 500 Å, between about 5 and about 400 Å, between about 5 and about 300 Å, between about 5 and about 200 Å, between about 5 and about 100 Å, between about 5 and about 80 Å, between about 5 and about 60 Å, between about 5 and about 40 Å, between about 5 and about 20 Å, between about 5 and about 10 Å, between about 2 and about 20 Å, between about 2 and about 10 Å, between about 3 and about 20 Å, between about 3 and about 10 Å, between about 4 and about 20 Å, and between about 4 and about 10 Å.

"Ambient pressure," as used herein, refers to about 1 atmosphere.

"Low pressure" refers to the partial pressure of ammonia or an amine in a gaseous mixture in contact with a polymer of the invention. In exemplary embodiments, "low pressure" refers to a partial pressure of ammonia or amine at or below about 999 ppm in a mixture at ambient pressure.

"Ambient temperature," as used herein, refers to about 25° C.

The term "strong acid," as used herein, refers to acids having a pKa about that of anhydrous chlorosulfonic acid.

The term "strong base," as used herein, refers to bases having a $pK_b$ about that of KOH/DMSO ("superbase").

The term "high temperature," as used herein refers to temperatures above about 100° C., about about 150° C. or above about 200° C.

"Stable," as used herein refers to a compound of the invention undergoing minimal degradation when maintained under strong acid, strong base, and/or high temperature for about 24 hours. "Minimal degradation" refers to no more than about 10%, no more than about 8%, no more than about 6%, no more than about 4% or no more than about 2% of a sample undergoing degradation.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure or be stereoisomeric mixtures. In addition it is understood that, in any compound described herein having one or more double bond(s) generating geometrical isomers that can be defined as E or Z, each double bond may independently be E or Z a mixture thereof. Likewise, it is understood that, in any compound described, all tautomeric forms are also intended to be included.

Below are examples of specific embodiments of the present invention. The examples are offered for illustrative purposes only, and are not intended to limit the scope of the present invention in any way.

III. Compositions

In one aspect of the present disclosure, there is provided functionalized porous aromatic polymer is formed from the monomer of Formulas (I), (II), (III) or (IV):

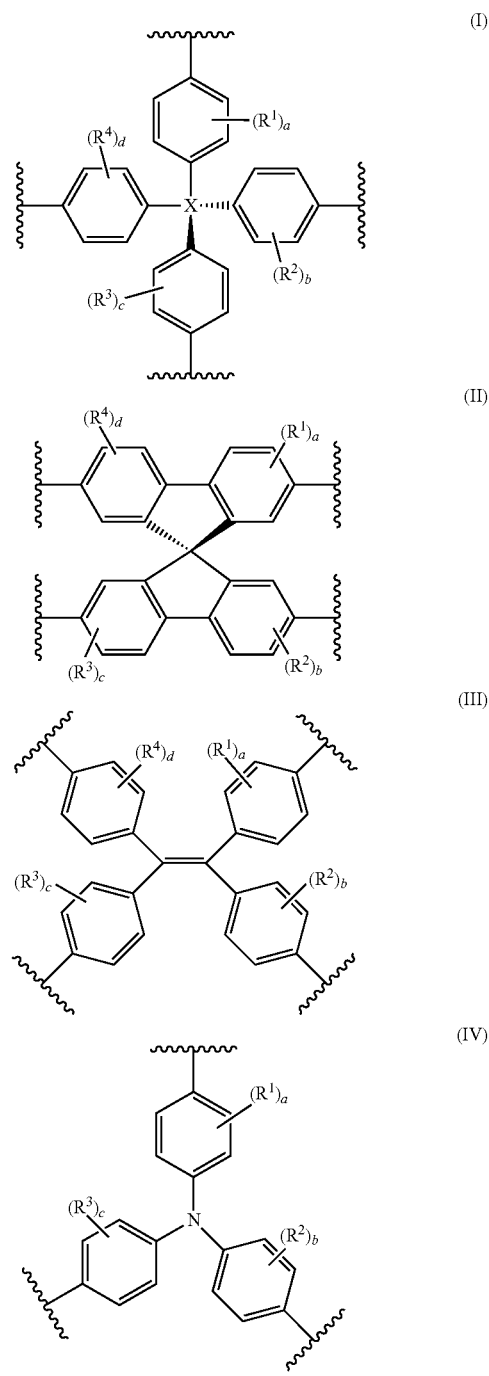

In these formulas, X is selected from C, Si, and a three-dimensional polycyclic cycloalkyl moiety. Further, $R^1$, $R^2$, $R^3$ and $R^4$ are independently selected from an alkyl thioether, a dialkyl thioether, 2,5-dithiahexane, 3,4-dithiahexane, 4,5-dithiahexane, (2-methoxyethyl)(methyl)sulfane, (2-methoxyethyl)(methyl)sulfane, 3-(methylthio)propanoic acid, ethylglycine, N-hydroxy-2-(methylamino)acetamide, 2-thiopentane, N-hydroxyacetamide and 2-methylhydrazine-1-carbothioamide. The indeces a, b, c and d are members independently selected from the integers 0, 1, 2, 3, and 4, such that when a, b, c, or d is greater than 1, each $R^1$, $R^2$, $R^3$ and $R^4$, respectively, is independently selected.

Another aspect of the present disclosure provides functionalized porous aromatic polymer that is a copolymer formed from a first monomer of Formula (I), (II), (III) or (IV) and a second monomer according to Formula (V):

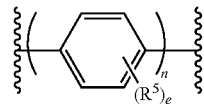
(V)

In this aspect, $R^5$ is a member selected from H, an alkyl thioether, a dialkyl thioether, 2,5-dithiahexane, 3,4-dithiahexane, or 4,5-dithiahexane, (2-methoxyethyl)(methyl)sulfane, (2-methoxyethyl)(methyl)sulfane, 3-(methylthio)propanoic acid, ethylglycine, N-hydroxy-2-(methylamino)acetamide, 2-thiopentane, N-hydroxyacetamide and 2-methylhydrazine-1-carbothioamide. The term "n" is 1, 2, or 3. The value "e" is an integer selected from 0, 1, 2, 3, and 4, such that when e is greater than 1, each $R^5$ is independently selected. The first monomer and the second monomer are covalently bound in the copolymer.

Yet another aspect of the present disclosure provides a functionalized porous aromatic polymer that is according to Formula (VI), (VII), (VIII), or (IX):

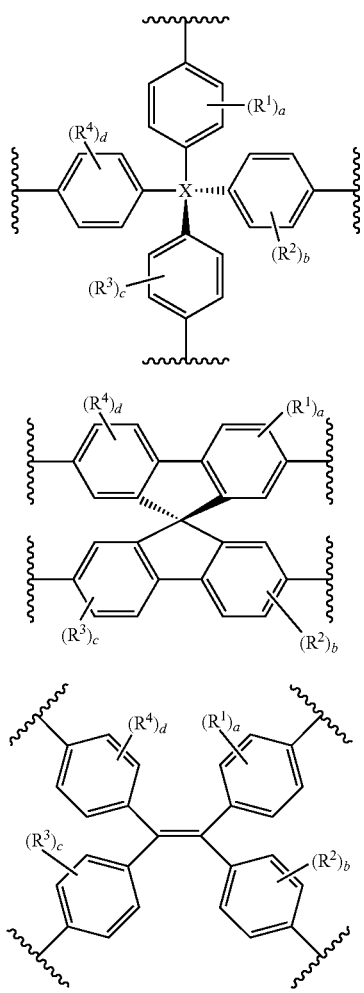

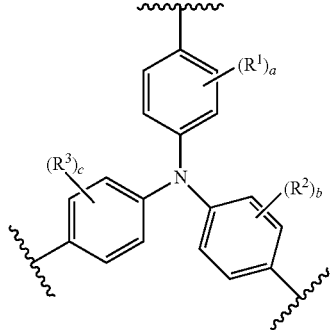
(IX)

In such embodiments, X is selected from C, Si, and a three-dimensional polycyclic cycloalkyl moiety. Further, $R^1$, $R^2$, $R^3$ and $R^4$ are each independently selected from Formula (X) or (XI):

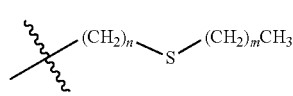
(X)

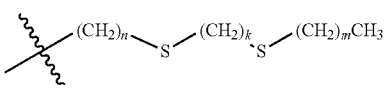
(XI)

Here, n is a zero or positive integer, m is zero or a positive integer, k is a positive integer, and the indeces a, b, c and d are members independently selected from the integers 0, 1, 2, 3, and 4, such that when a, b, c, or d is greater than 1, each $R^1$, $R^2$, $R^3$ and $R^4$, respectively, is independently selected.

Yet another aspect of the present disclosure provides a functionalized porous aromatic polymer is a copolymer formed from a first monomer of Formula (VI), (VII), (VIII) or (IX) and a second monomer of Formula (XII):

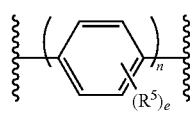
(XII)

In such embodiments, $R^5$ is a member selected from H, an alkyl thioether, a dialkyl thioether, 2,5-dithiahexane, 3,4-dithiahexane, 4,5-dithiahexane, (2-methoxyethyl)(methyl)sulfane, (2-methoxyethyl)(methyl)sulfane, 3-(methylthio)propanoic acid, ethylglycine, N-hydroxy-2-(methylamino)acetamide, 2-thiopentane, N-hydroxyacetamide and 2-methylhydrazine-1-carbothioamide. Further, the index "e" is an integer selected from 0, 1, 2, 3, and 4, such that when e is greater than 1, each $R^5$ is independently selected. The first monomer and the second monomer are covalently bound in the copolymer.

Still another aspect of the present disclosure provides the functionalized porous aromatic polymer according to Formula (XIII), (XIV), (XV), or (XVI):

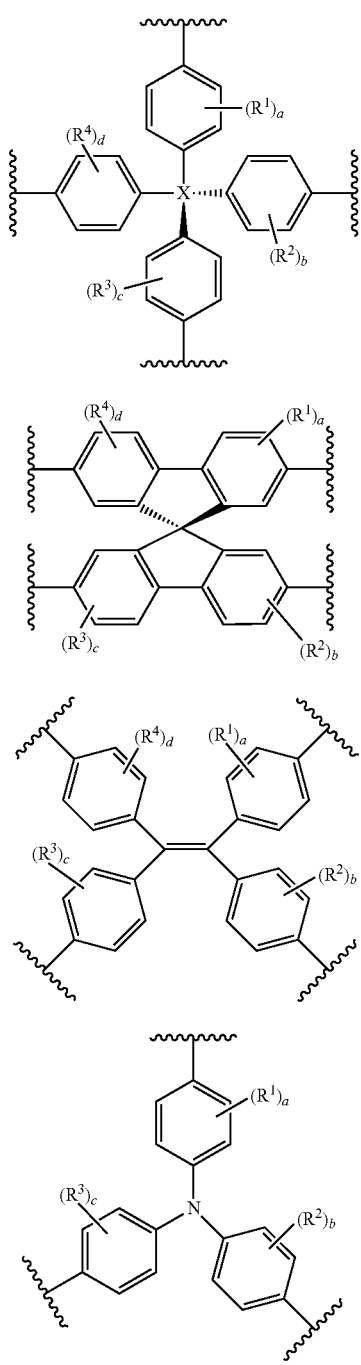

(XIII)

(XIV)

(XV)

(XVI)

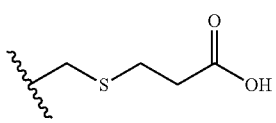

In such embodiments, X is selected from C, Si, and a three-dimensional polycyclic cycloalkyl moiety. Further, R', R², R³ and R⁴ are independently selected from Formula (XVII) or (XVIII):

(XVII)

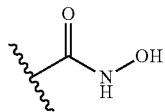

(XVIII)

Moreover, the indeces a, b, c and d are members independently selected from the integers 0, 1, 2, 3, and 4, such that when a, b, c, or d is greater than 1, each $R^1$, $R^2$, $R^3$ and $R^4$, respectively, is independently selected.

Still another aspect of the present disclosure provides the functionalized porous aromatic polymer is a copolymer formed from a first monomer of Formula (XIII), (XIV), (XV) or (XVI) and a second monomer according to Formula (XIX):

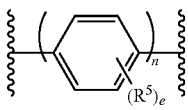

(XIX)

In such embodiments, $R^5$ is independently selected from Formula (XX) or (XXI):

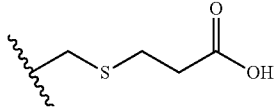

(XX)

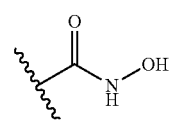

(XXI)

Morover, the index "e" is an integer selected from 0, 1, 2, 3, and 4, such that when e is greater than 1, each $R^5$ is independently selected. Furthermore, the first monomer and the second monomer are covalently bound in the copolymer.

IV. Examplary Assay

In addition to the polymers discussed above and in the Examples, the present invention provides a method of selective detection of a concentration of a metal ion species in a subject is provided in which a biofluid sample is obtained from the subject. The biofluid sample is exposed to a functionalized porous aromatic polymer. The polymer selectively captures and concentrates the metal ion species from the biofluid. Subsequently, the biofluid is washed from the polymer. The polymer is then exposed to a solution comprising a colorimetric indicator that extracts the metal ion species from the washed polymer thereby changing a color of the solution as a function of an amount of the metal ion species in the polymer. The concentration of the metal ion species in the subject is then spectroscopically determined from the color of the solution.

The following examples illustrate embodiments of the invention and are not intended to limit the scope of the compositions of the invention or the methods in which they find use.

EXAMPLES

Copper is an essential nutrient for life, but at the same time hyperaccumulation of this redox-active metal in biological fluids and tissues is a hallmark of pathologies such as Wilson's and Menkes diseases, various neurodegenerative diseases, and toxic environmental exposure. Diseases characterized by copper hyperaccumulation are currently challenging to identify due to costly diagnostic tools that involve extensive technical workup. Motivated to create simple yet highly selective and sensitive diagnostic tools, the present example details the development of new materials that enable monitoring of copper levels in biological fluid samples without complex and expensive instrumentation. The present examples disclose the design, synthesis, and properties of PAF-1-SMe, a robust diamondoid porous aromatic framework (PAF) densely functionalized with thioether groups for selective capture and concentration of copper from biofluids as well as aqueous samples. PAF-1-SMe exhibits a high selectivity for copper over other biologically-relevant metals, with a saturation capacity reaching over 600 mg/g. Moreover, the combination of PAF-1-SMe as a material for concentration and capture of copper from biological samples with 8-hydroxyquinoline as a colorimetric indicator affords a method for identifying aberrant elevations of copper in urine samples from mice with Wilson's disease and also tracing exogenously added copper in serum. This divide-and-conquer sensing strategy, where functional and robust porous materials serve as molecular recognition elements that can be used to capture and concentrate analytes in conjunction with molecular indicators for signal readouts, establishes a valuable starting point for the use of porous polymer materials in non-invasive diagnostic applications.

The present examples demonstrate that the robust thioether-functionalized porous aromatic framework, PAF-1-SMe, accomplishes selective and efficient copper uptake from aqueous media, including from biofluid samples. The example method differentiates between urine samples of healthy and Wilson's disease mice, and the combination of PAF-1-SMe with 8-HQ as a colorimetric indicator provides an efficient and accessible tool for metal detection directly from biological specimens with minimal processing and instrumentation needs. The data provided in this example serves as a basis for the use of functionalized porous materials in diagnostic or sensing applications for compatible biological, and environmental, field samples. In a broader sense, the divide-and-conquer strategy to indicator design provided in this example, where one materials component is involved in capture and concentration of analytes from samples with minimal processing, while the other molecular component offers a detection readout, is readily generalized and will offer a broad range of possibilities for mixing and matching different molecular, materials, and biological components for various sensing and imaging applications.

Synthesis and Characterization.

Figure 7:
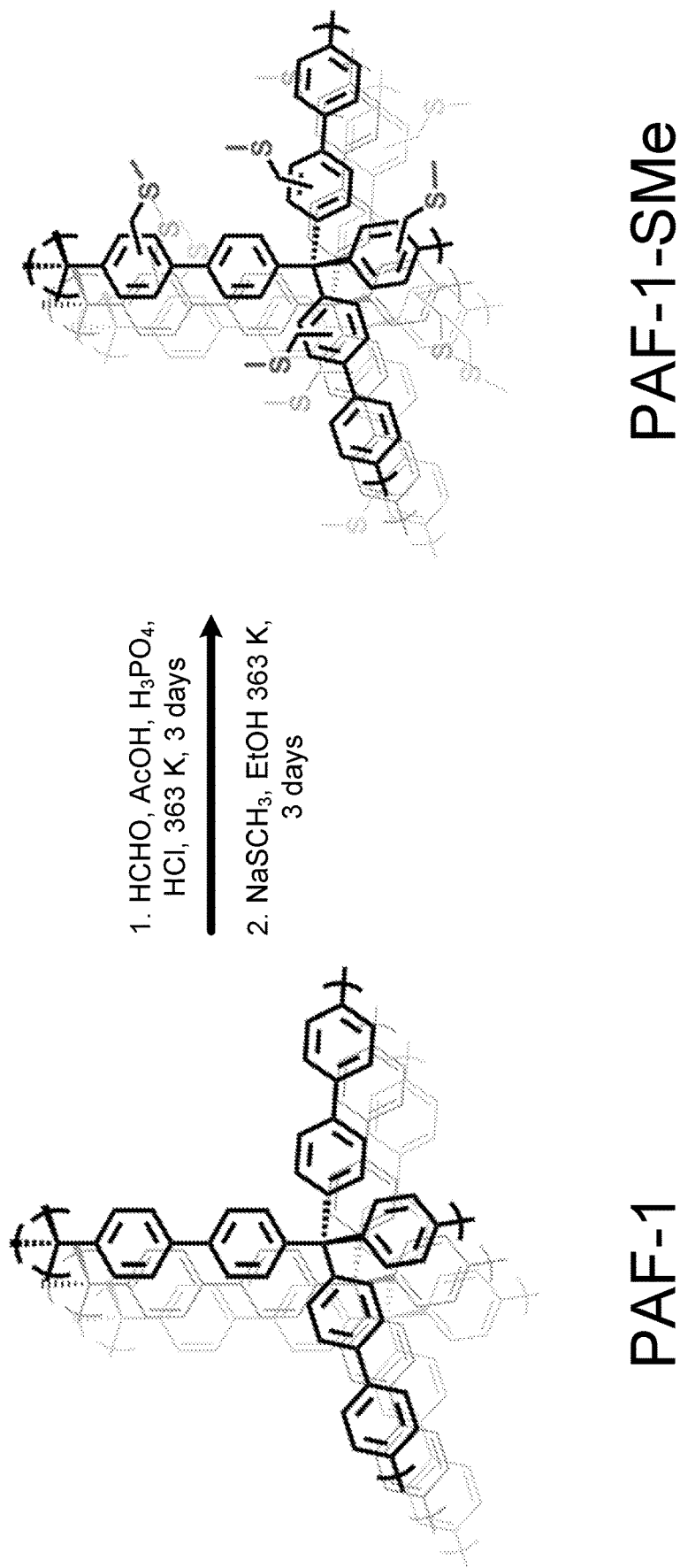
FIG. 7 illustrates synthesis of PAF-1-SMe in accordance with an embodiment of the present disclosure.

The parent material PAF-1- was synthesized following a procedure reported in the literature, (Ben et al., 2009, *Angew. Chem. Int. Ed.* 48, 9457-9460; Ben and Qiu, 2013, *CrystEngComm* 15, 17-26, hereby incorporated by reference) and chloromethylation of the phenyl rings of PAF-1 (Li et al, 2014, *Nat. Commun* 5, 5537-5543, hereby incorporated by reference) followed by treatment with NaSMe afforded the final PAF-1-SMe product. See FIG. 7. Infrared spectroscopy revealed the successful formation of PAF-1-SMe as evidenced by the disappearance of C—H wagging of the —CH$_2$Cl group at 1265 cm$^{-1}$ in PAF-1-CH$_2$Cl. See FIG. 8. Elemental analysis also revealed a decrease in chlorine content from 13.6% in PAF-1-CH$_2$Cl to 0.5% in the thioether-functionalized material, further supporting a successful transformation. The sulfur content in PAF-1-SMe was determined to be 9.6±1.3% via elemental analysis, providing further evidence for efficient thioether formation from the chloromethyl starting material. Finally, solid-state $^1$H—$^{13}$C cross-polarization magic angle spinning (CP/MAS) NMR (FIG. 1a) monitored distinct $^{13}$C chemical shifts associated with the PAF-1-CH$_2$Cl synthetic intermediate (43 ppm for —CH$_2$Cl group) and the final PAF-1-SMe product (35 and 13 ppm for —CH$_2$SCH$_3$ group), further confirming successful incorporation of —SMe groups.

In order to reveal the copper coordination in thioether groups, additional solid-state $^{13}$C NMR experiments were performed. Indeed, we observed that addition of copper to the PAF1-SMe material specifically broadened and decreased the intensities of peaks assigned to the thioether ligands and benzyl ring, which can be interpreted as copper being in proximity to these functionalities. Furthermore, data from EPR experiments provided a separate line of evidence for interaction between copper and thioether groups. See FIG. 9.

Figure 10B:
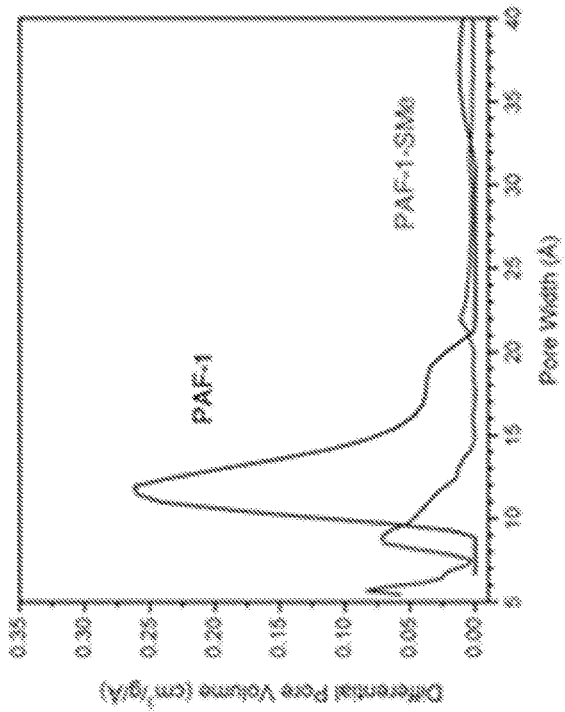
FIG. 10A illustrates $N_2$ sorption isotherms of PAF-1, PAF-1-CH$_2$Cl, and PAF-1-SMe at 77 K, FIG. 10B pore size distribution comparison of PAF-1 and PAF-1-SMe, FIG. 10C differential and cumulative pore volume graph of PAF-1, and FIG. 10D differential and cumulative pore volume graph of PAF-1-SMe, in accordance with some embodiments.
Figure 10D:
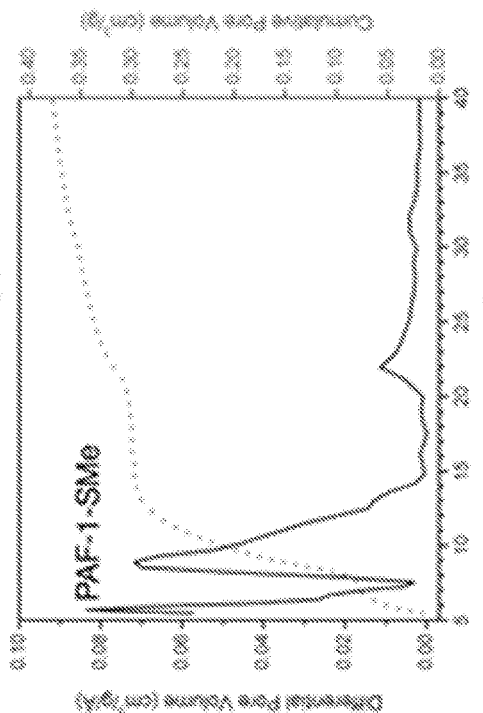

N$_2$ adsorption isotherms collected at 77 K (FIG. 10a) revealed that PAF-1-SMe retained high permanent porosity with a BET surface area of 1075 m$^2$/g, albeit smaller than the parent PAF-1 surface area of 3505 m$^2$/g. The pore size distributions obtained from the adsorption isotherms were also in agreement with the incorporation of —CH$_2$SMe groups. Indeed, while PAF-1 exhibited a uniform pore size distribution centered around 12 Å, PAF-1-SMe exhibited pore width maxima located at 6 Å and 9 Å (FIG. 10d). To the best of our knowledge, PAF-1-SMe possesses the highest surface area of any thioether-modified porous material, including mesoporous materials (~979 m$^2$/g), organosilicas (15-260 m$^2$/g), (See Kim et al., 2012, *Chem. Mater.* 24, 2256-2264, which is hereby incorporated by reference) metal-organic frameworks (~618 m$^2$/g), (See, He et al., 2013, *Am. Chem. Soc.* 135, 7807-7810, which is hereby incorporated by reference) silsesquioxane aerogels (90-272 m$^2$/g) (See, Wang et al., 2015, *ACS Appl. Mater. Interfaces* 7, 2016-2024, which is hereby incorporated by reference), and a thioether-based fluorescent covalent organic framework (454 m$^2$/g) (See Ding et al., 2016, *J. Am. Chem. Soc.* 138, 3031-3037, which is hereby incorporated by reference). Although we note elegant work that shows that high surface area is not a strict prerequisite for high performance (Alsbaiee et al., 2016, *Nature* 529, 190-194 hereby incorporated by reference), the relatively high surface area and permanent porosity of PAF-1-SMe are both good indicators of the accessibility of the thioether groups within the polymeric network.

Copper Uptake, Kinetics, and Selectivity.

Figure 14A:
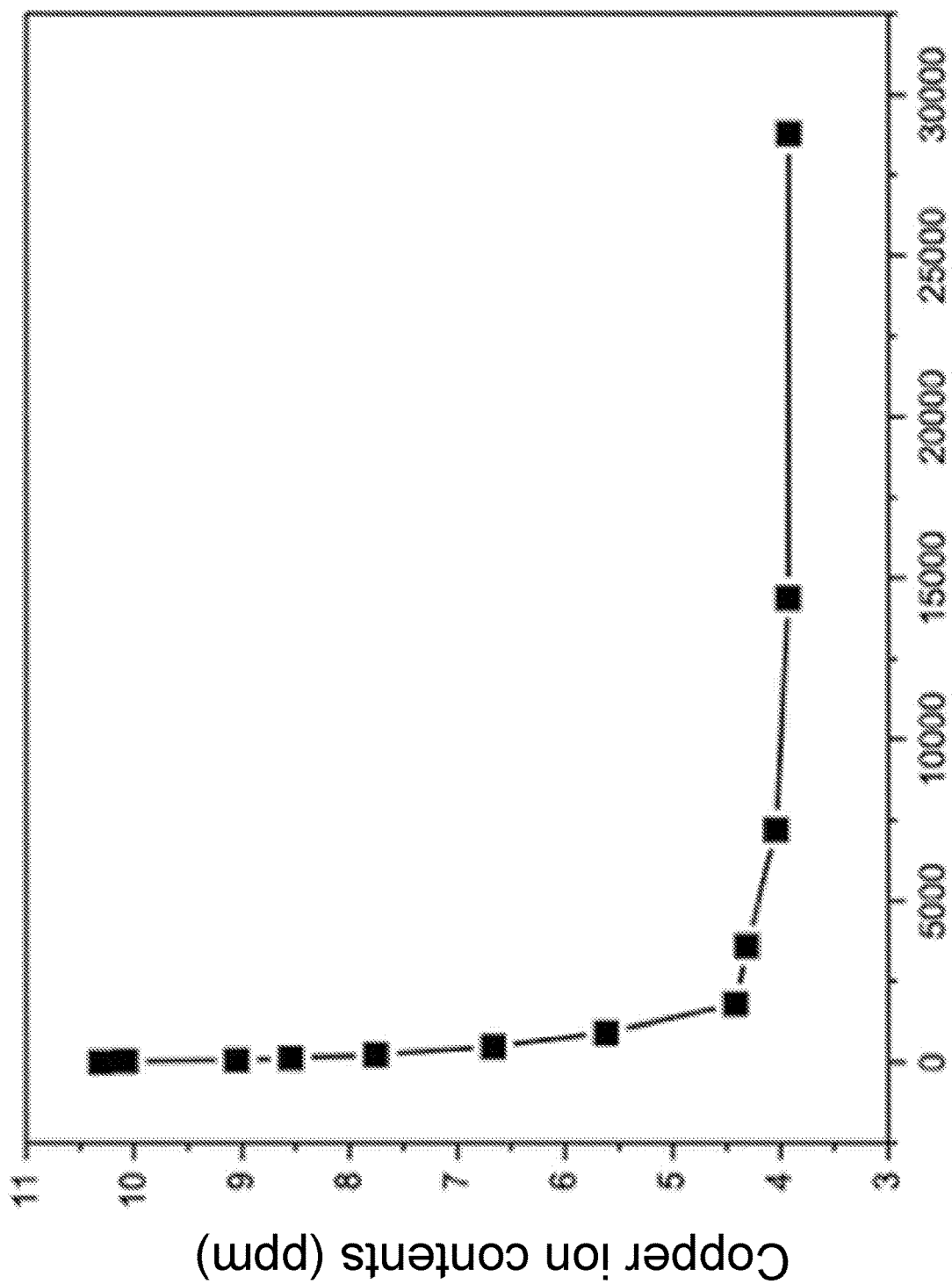
FIG. 14A and FIG. 14B illustrate Copper(II) adsorption kinetics of PAF-1-SMe using a copper(II) solution of 10 ppm (100 mM HEPES buffer, pH 6.7)
Figure 14B:
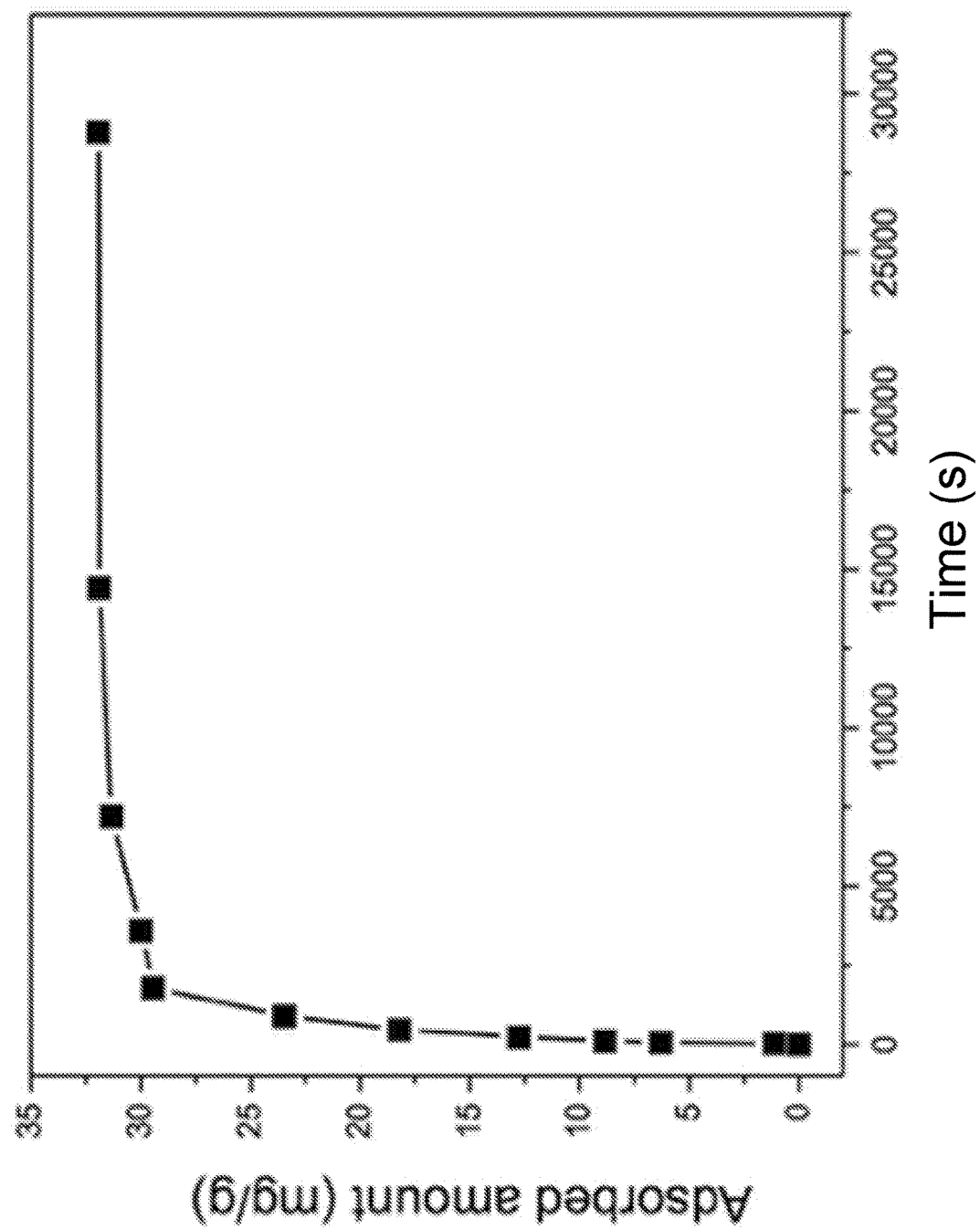
Figure 14C:
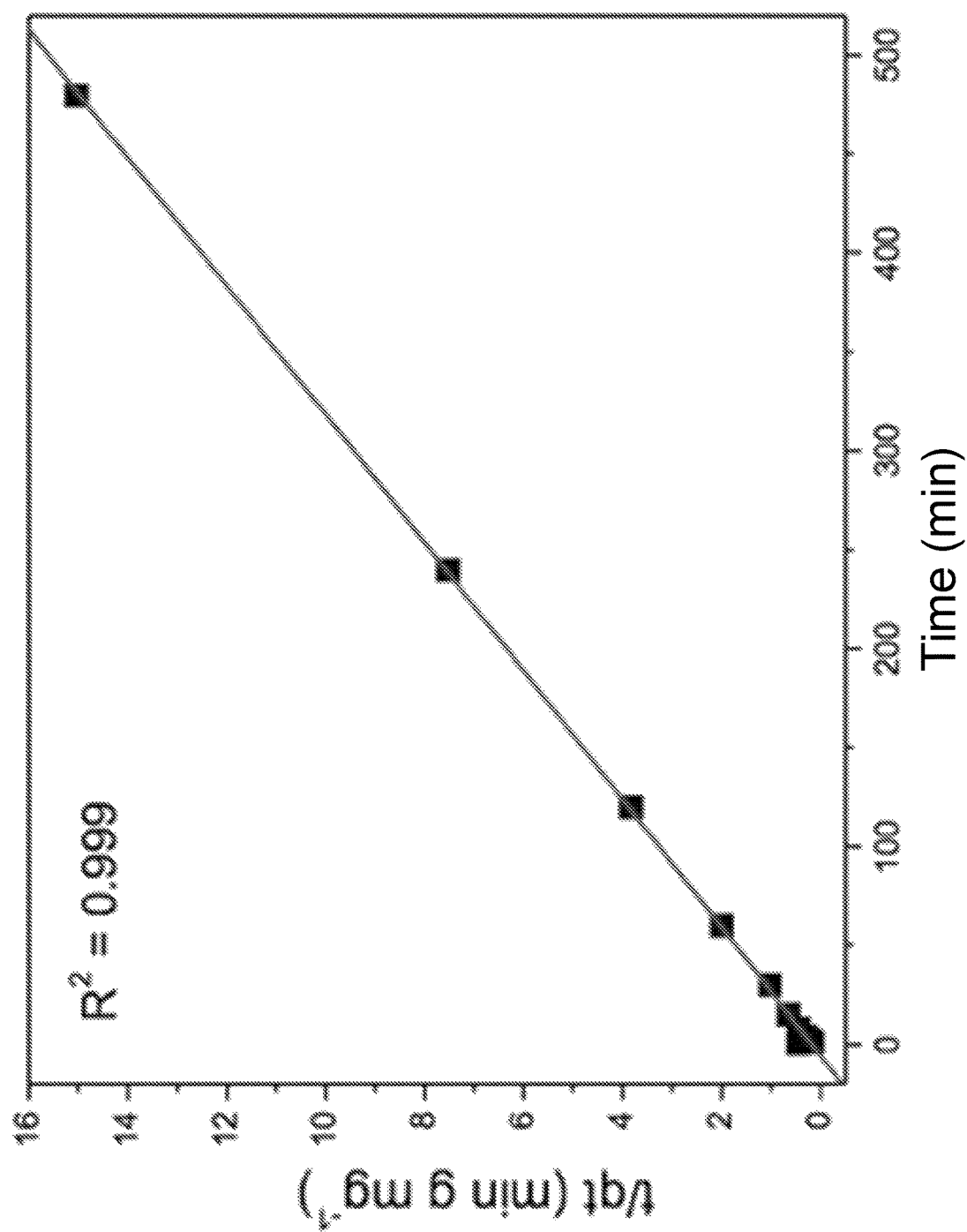
FIG. 14C Pseudo-second order kinetic plot for copper(II) adsorption provided a high correlation coefficient and a rate constant $k_2$ of 5.2 $mg^{-1}$ $min^{-1}$.
Figure 15A:
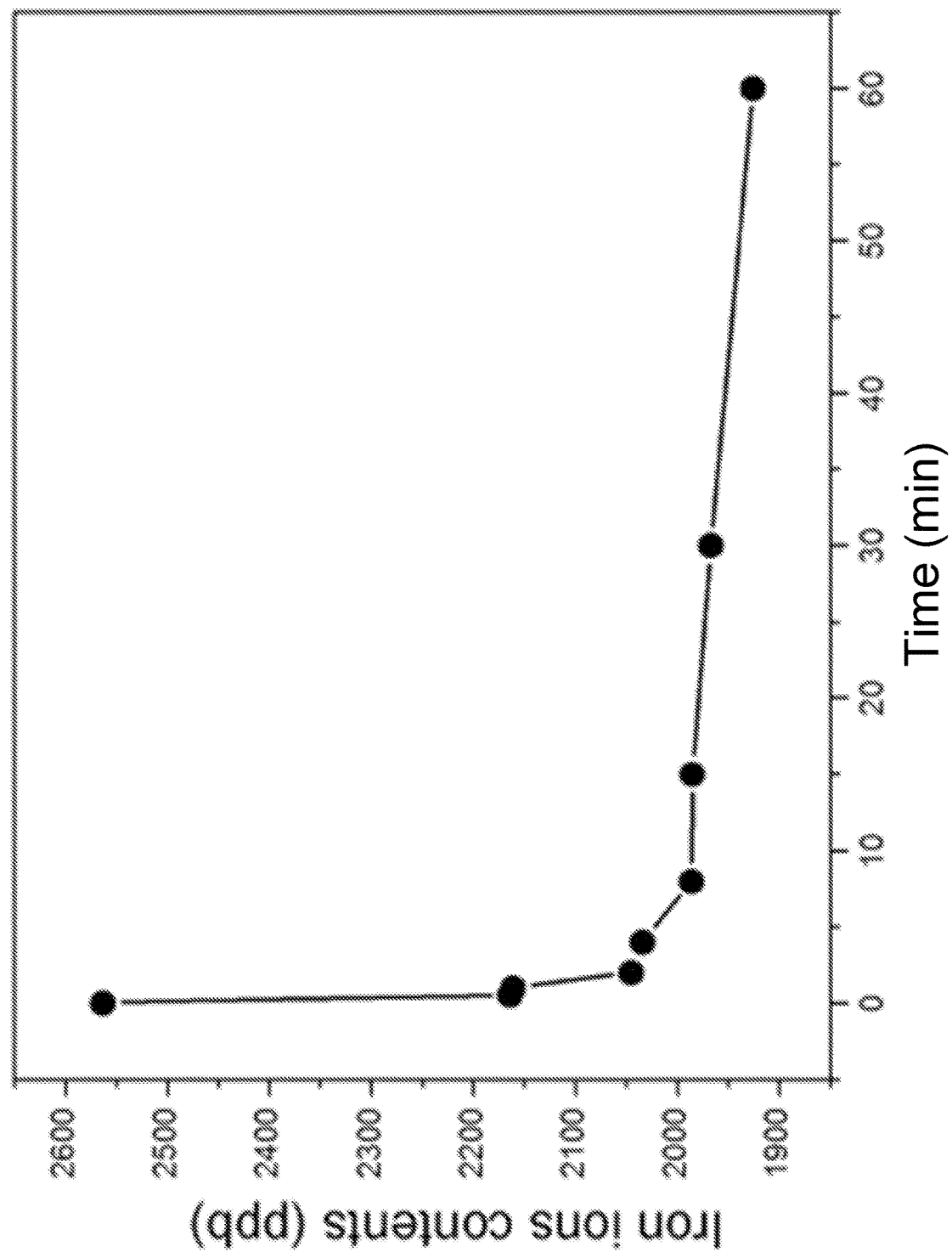
FIG. 15A and FIG. 15B illustrate Iron(II) adsorption kinetics of PAF-1-SMe using an iron(II) solution of 5 ppm (100 mM HEPES buffer, pH 6.7)
Figure 15B:
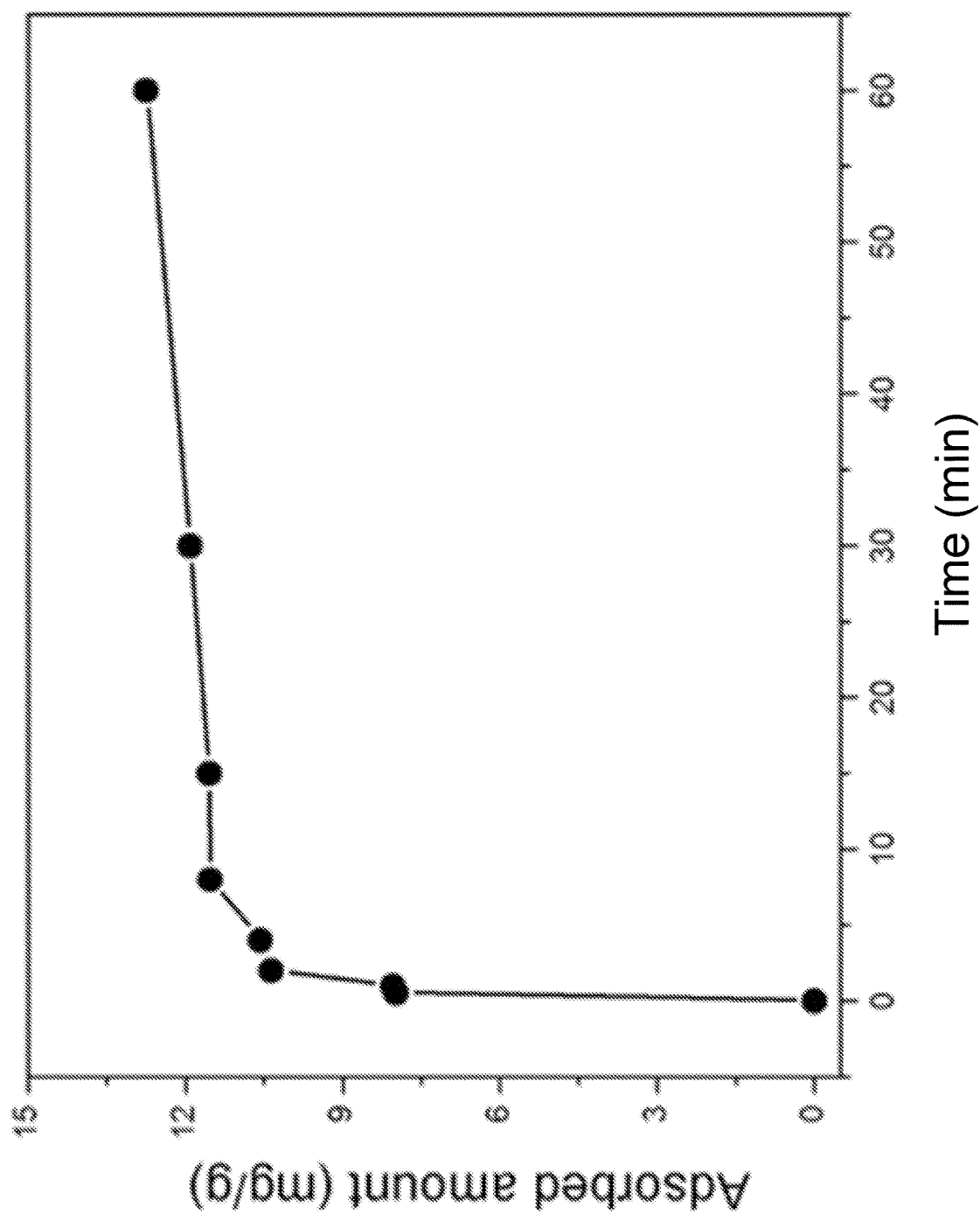
Figure 15C:
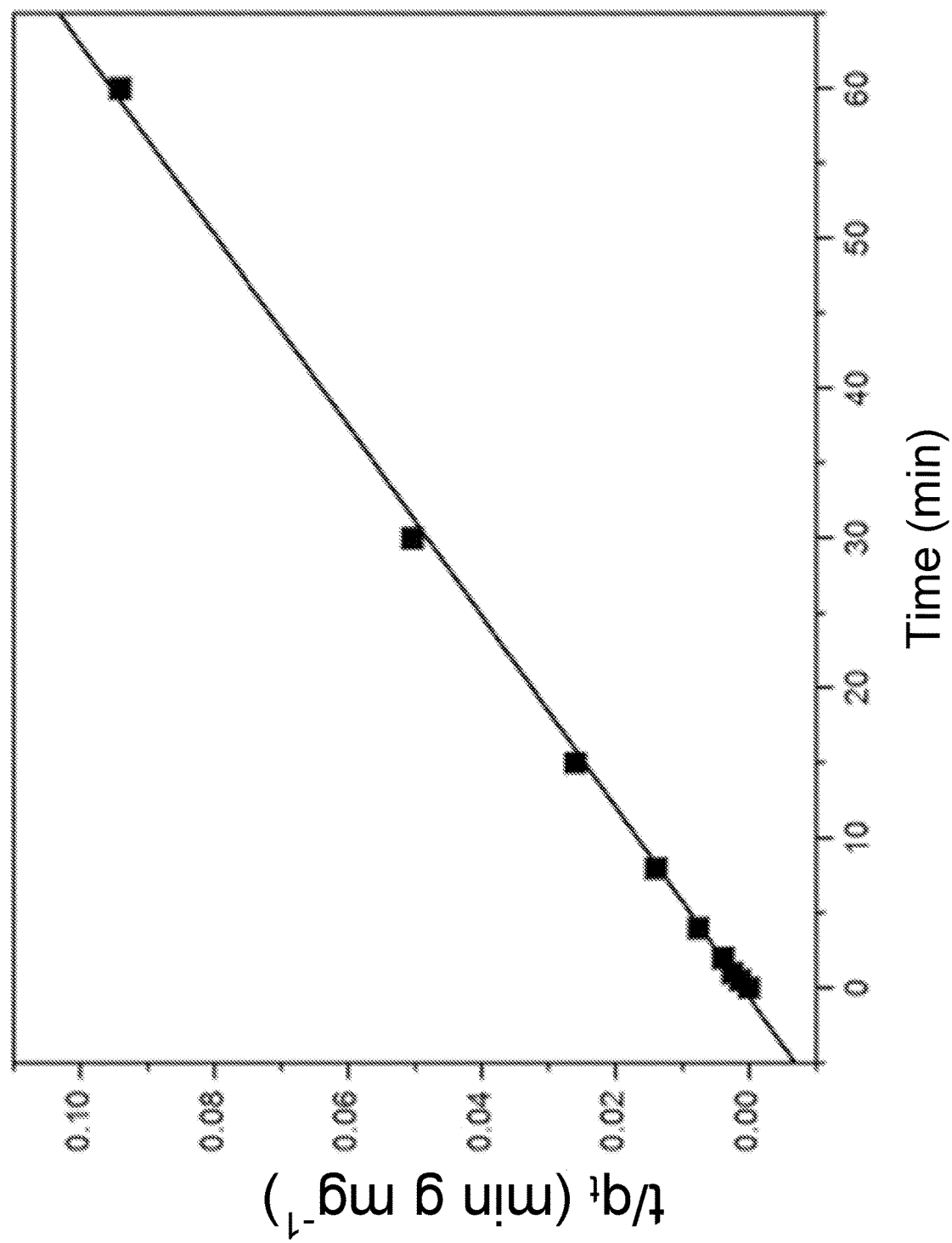
FIG. 15C pseudo-second order kinetic plot for iron(II) adsorption provided a high correlation coefficient and a rate constant $k_2$ of 2.2 $mg^{-1}$ $min^{-1}$.

After confirming the porosity and structural integrity of PAF-1-SMe upon post synthetic modification, we examined its ability to capture copper ions from aqueous solution. The distribution coefficient, $K_d$, was measured with 4 ppm copper in HEPES buffer at pH=6.7 and found $1.3\pm0.2\times10^5$ mL/g, indicating a high copper selectivity and a more than 10-fold improvement over the best copper adsorbent materials reported to date ($1.2\times10^4$ mL/g). See Burleigh et al., 2001, *Separ. Sci. Technol.* 36, 3395-3409; Ebraheem and Hamdi, 1997, *React. Funct. Polym.* 34, 5-10, each of which is hereby incorporated by reference. Time-course adsorption measurements further indicated that copper capture by PAF-1-SMe is kinetically efficient (FIG. 14), with a pseudo-second order adsorption rate constant of 5.2 mg/mg·min that reaches equilibrium capacity within ~30 min.

Figure 2A:
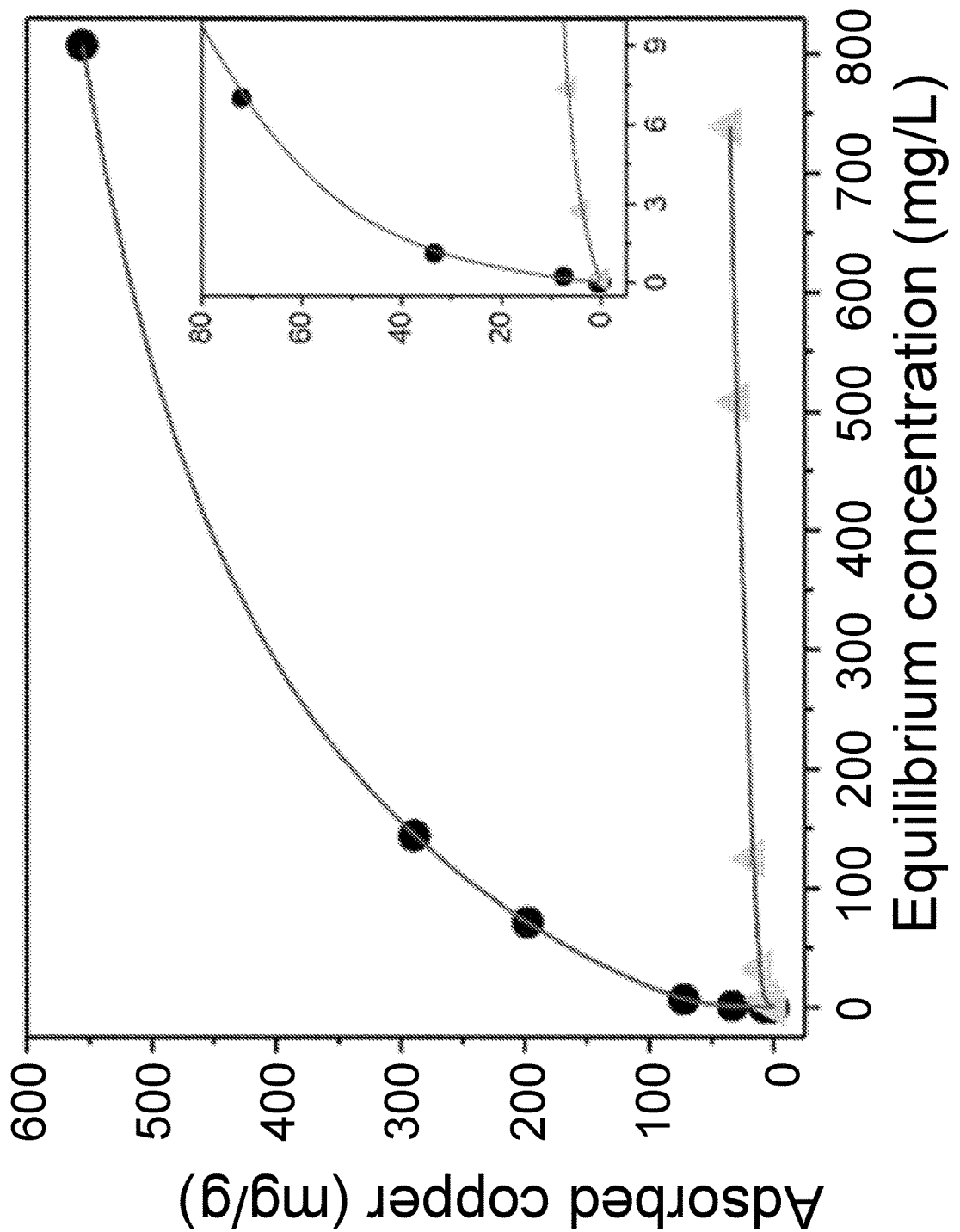
FIG. 2A illustrates Copper adsorption isotherm for PAF-1-SMe (black circles) and PAF-1-CH2Cl (triangles) fit using a dual-site Langmuir model (line connecting circles, line connecting triangls). The inset plot is magnified portion of initial equilibrium concentration range (0-10 mg/L) and absorbed amount of copper (mg/g)

We assessed the overall capacity of PAF-1-SMe for copper from fitting of adsorption isotherms collected after equilibrating the polymer with a wide range of copper levels (1 ppb-800 ppm, FIG. 2a). The best fit for the experimental data utilized a dual-site Langmuir model (Mason et al., 2011, *Energy. Environ. Sci.* 4, 3030-3040, hereby incorporated by reference) with a strong adsorption site (saturation capacity of 67 mg/g) and a weak adsorption site (saturation capacity of 662 mg/g). The strong adsorption site was correlated with the thioether groups within the framework, and this assignment is supported by comparing copper adsorption in PAF-1-CH$_2$Cl and PAF-1-SMe up to ~10 ppm (FIG. 2a, inset). For the low concentrations most relevant to diagnostic copper capture in biofluids, PAF-1-SMe displayed a much steeper uptake than PAF-1-CH$_2$Cl, and this enhanced uptake notably persisted for higher copper concentrations (35 mg/g at 740 ppm). By comparison, PAF-1-CH$_2$Cl showed higher uptake (~30-fold) in the range 3 ppb-740 ppm, providing evidence for the presence of copper ions trapped within the pores and/or adsorption at weaker binding sites in PAF-1-SMe. We note that the experimental saturation capacities for PAF-1-SMe were higher than predicted based on the calculated thioether density, and thus it is likely that each sulfur atom is capable of coordinating more than one copper ion. A similar observation was made with regard to sulfur-functionalized mesoporous carbons (Sing et al., 2007, R. *Adv. Funct. Mater.* 17, 2897-2901, which is hereby incorporated by reference). Notably, the total saturation capacity exhibited by PAF-1-SMe is higher than all previously reported copper adsorbents, including cellulose resin modified with sodium metaperiodate and hydroxamic acid groups (~246 mg/g), (O'Connell et al., 2008, *Biores. Tech.* 99, 6709-6724, which is hereby incorporated by reference) zeolites, biomass and lignin-derived adsorbents (5.1-133.4 mg/g) (Petrić, 2004, *Water Research* 38, 1893-1899; (b) Feng et al., 2004, *Sep. Purif. Technol.* 40, 61-67; (c) Say et al., 2005, *Biores. Tech.* 23, 313-322; and (d) Bayramoğlu et al., 2003, *Hazard. Mater.* 101, 285-300, each of which is hereby incorporated by reference), silica-polyamine composite resins (~80 mg/g), (Beatty et al., 1999, *Ind. Eng. Chem. Res.* 38, 4402-4408, which is hereby incorporated by reference) and silica-based polymers (0.5-147 mg/g) (Kumar et al., 2007, *Sep. Purif. Technol.* 57, 47-56, which is hereby incorporated by reference). More interestingly, the comparison of PAF-1-SMe to a commercially available thiol functionalized resin (Duolite GT-73) provided us valuable information on the highly accessible nature of —CH$_2$SMe groups in PAF-1-SMe. This resin, featuring a higher loading of thiol groups (sulfur content of 16%) yet a much lower surface area (50 m$^2$/g), was reported (Kumar et al., 2007, *Sep. Purif. Technol.* 57, 47-56, hereby incorporated by reference) to have a copper uptake of 25 mg/g at an equilibrium concentration of 160 ppm. Such a striking difference in uptake capacities underlines the importance of functional group accessibility which we believe is enabled by the highly porous nature of PAF-1-SMe.

Figure 2B:
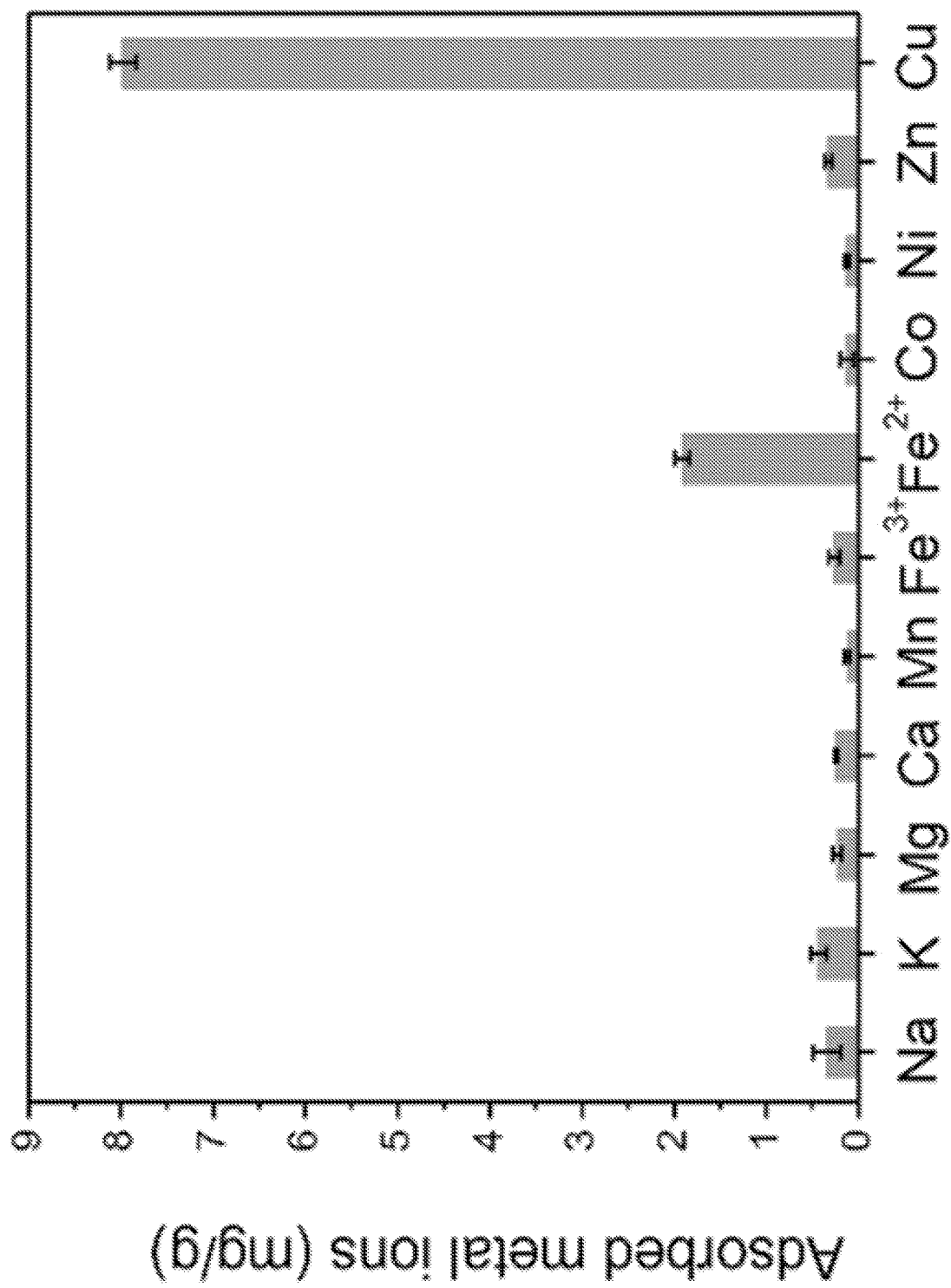
FIG. 2B illustrates PAF-1-SMe capture capacities of physiologically relevant metal ions (10 ppm). Data collected in 100 mM HEPES pH=6.7.
Figure 19A:
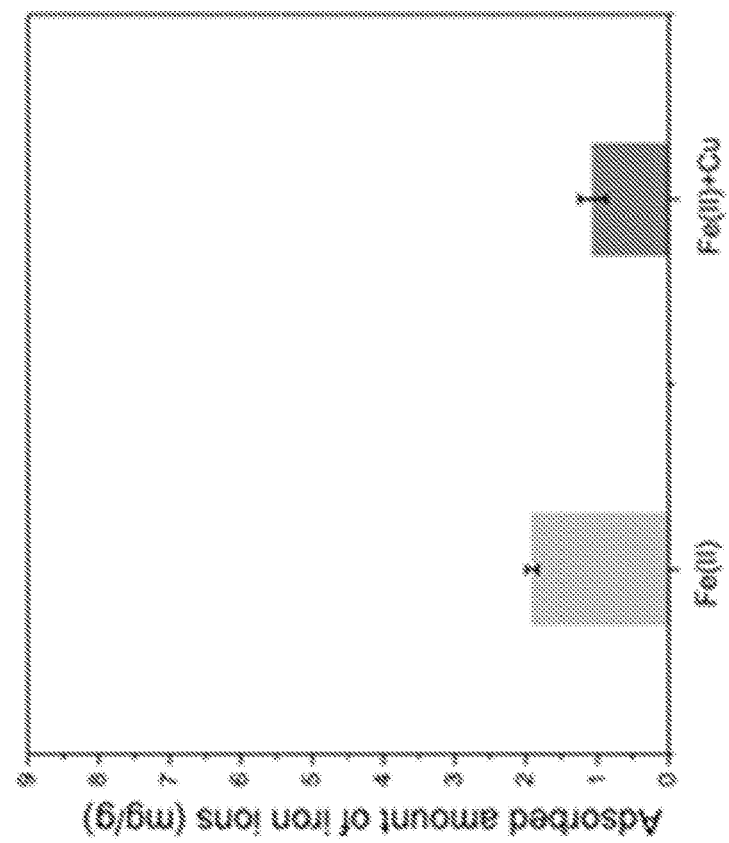
FIG. 19A and FIG. 19B illustrate a competitive assay for iron and copper ion uptake.
Figure 19B:
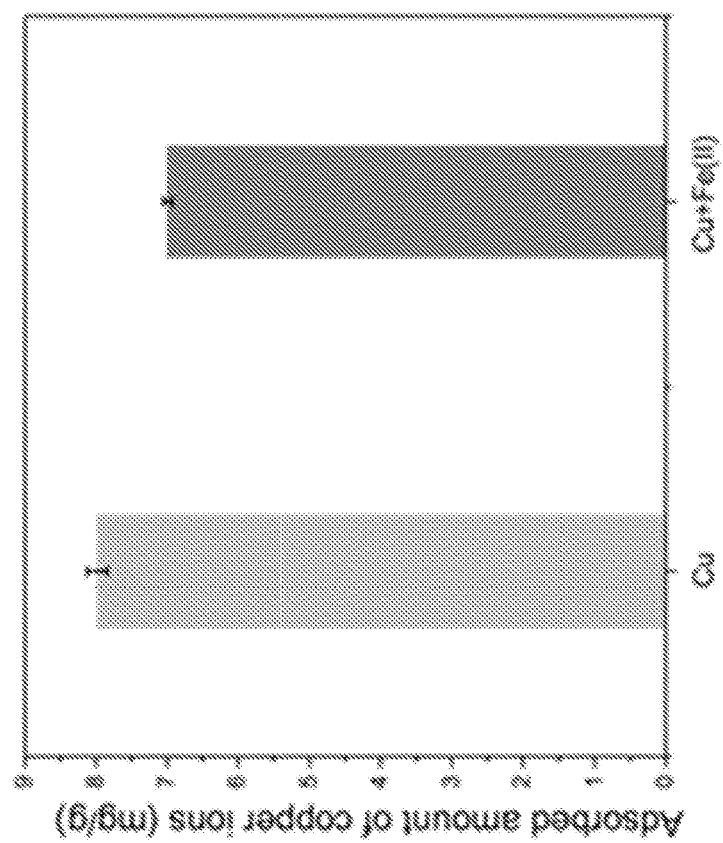
Figure 20:
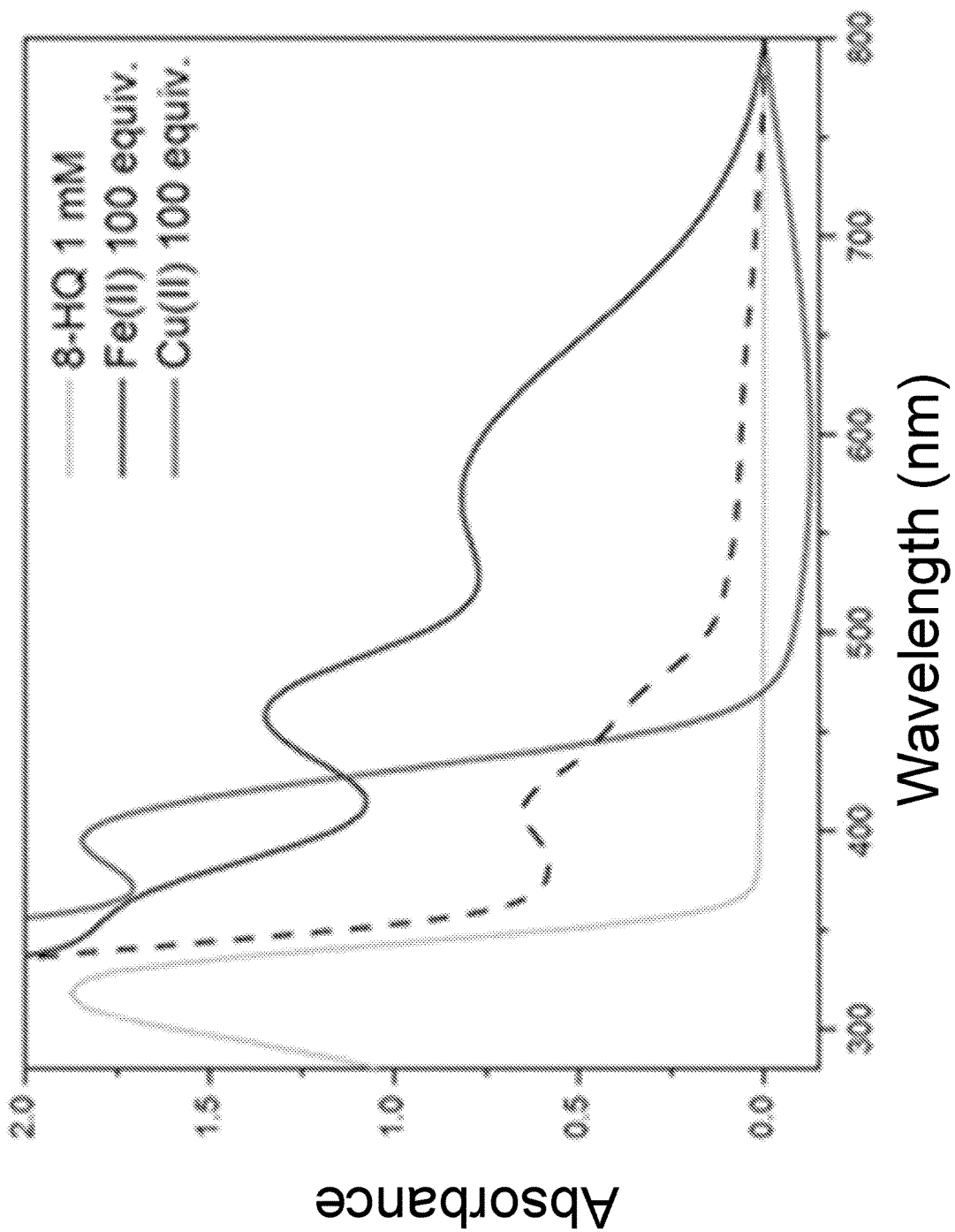
FIG. 20 illustrates UV-Vis absorption spectra of 8-hydroxyquinoline with copper and iron ions (100 equiv. to 8-HQ in DMSO, red and blue, respectively) and spectra of 8-hydroxyquinoline (8-HQ) treated with PAF-1-SMe (2 mg) applied in serum without acetohydroxamic acid (AHA), which reveals absorption at 400 nm, 450 nm (sh) and 600 nm (sh) (dashed).
Figure 21:
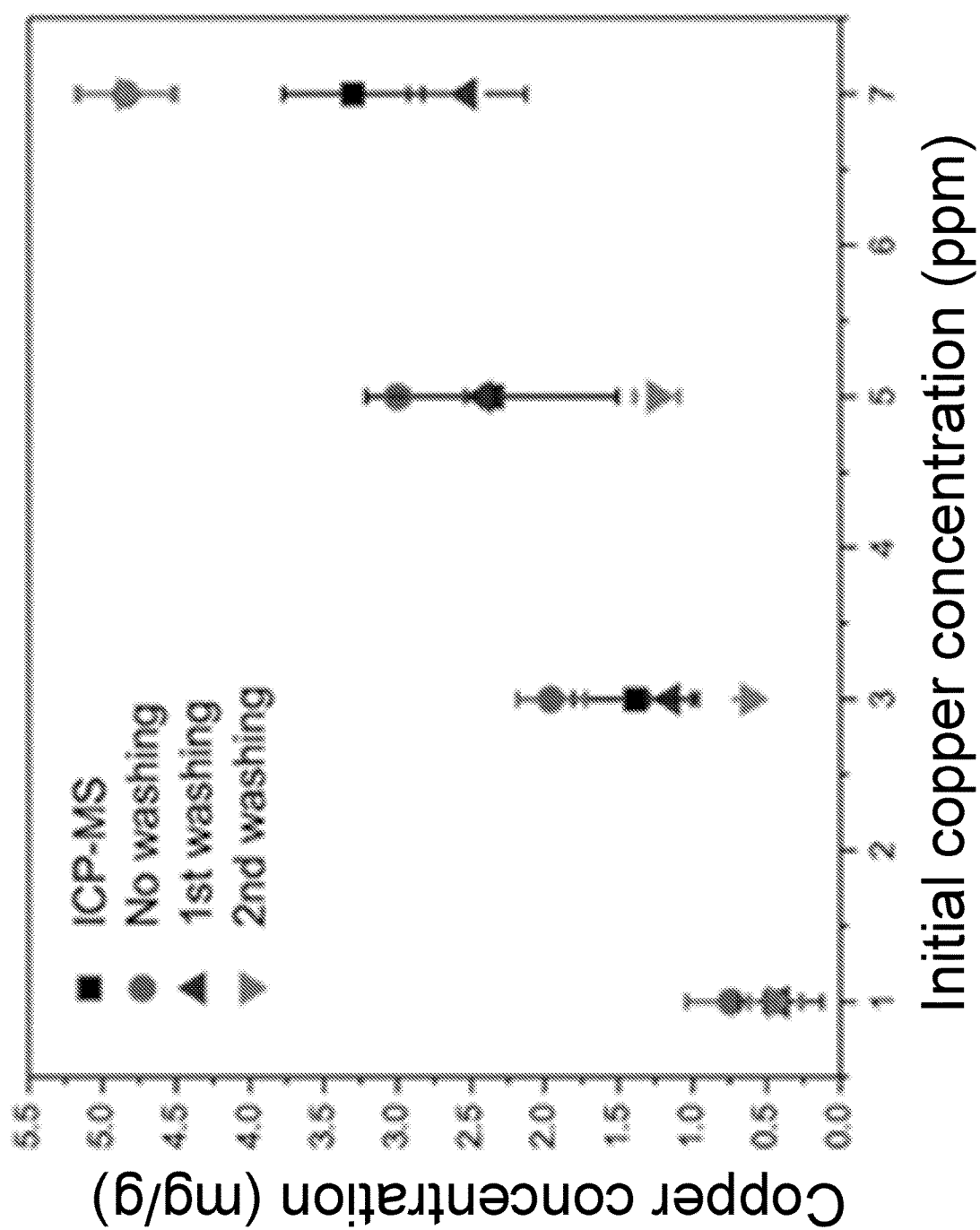
FIG. 21 illustrates the washing effect before adding 1 mM 8-hydroxyquinoline (8-HQ) to dried PAF-1-SMe. The calculated copper concentrations embedded into PAF-1-SMe based on absorption at 410 nm, without washing before adding 1 mM 8-HQ, are represented as red circled. Data taken after washing with DMSO once or twice before treating with 8-HQ are represented as regular and inverted triangles, respectively.
Figures 22A, 22B:
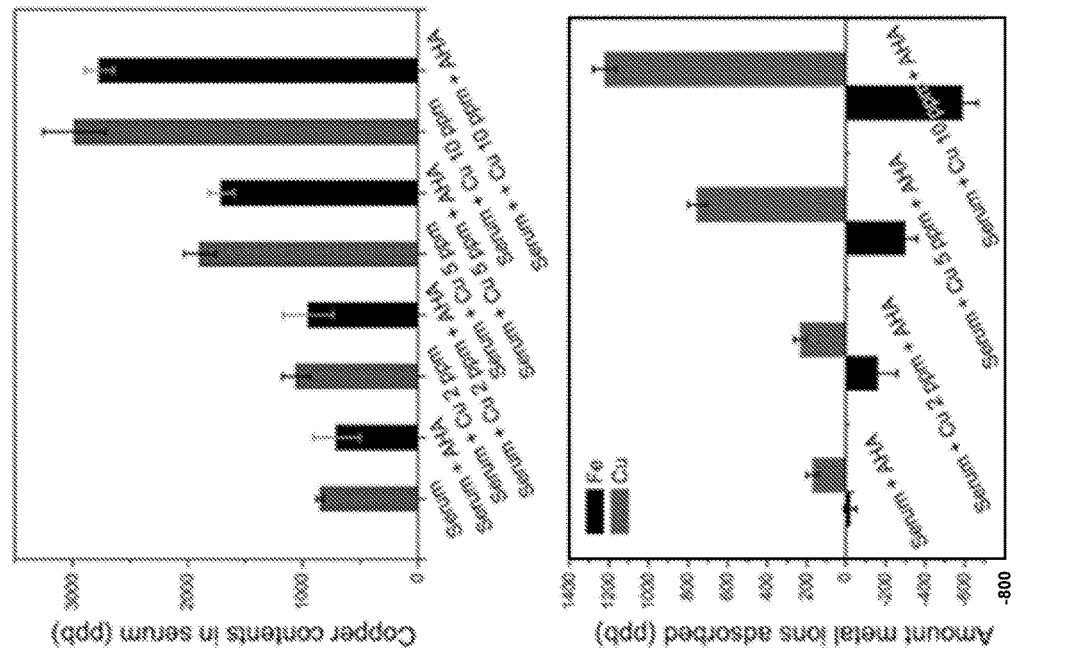
FIG. 22A illustrates Iron contents in serum (4 mL) in the absence (light gray bar) and presence (gray bar) of acetohydroxamic acid (AHA)
FIG. 22B Copper contents in serum in the absence (dark gray bar) and presence (black bar) of acetohydroxamic acid (AHA). Adsorbed amount of iron and copper ions by PAF-1-SMe (2 mg) in the absence of AHA is shown in FIG. 22C and in presence of AHA is shown in FIG. 22D.
Figures 22C, 22D:
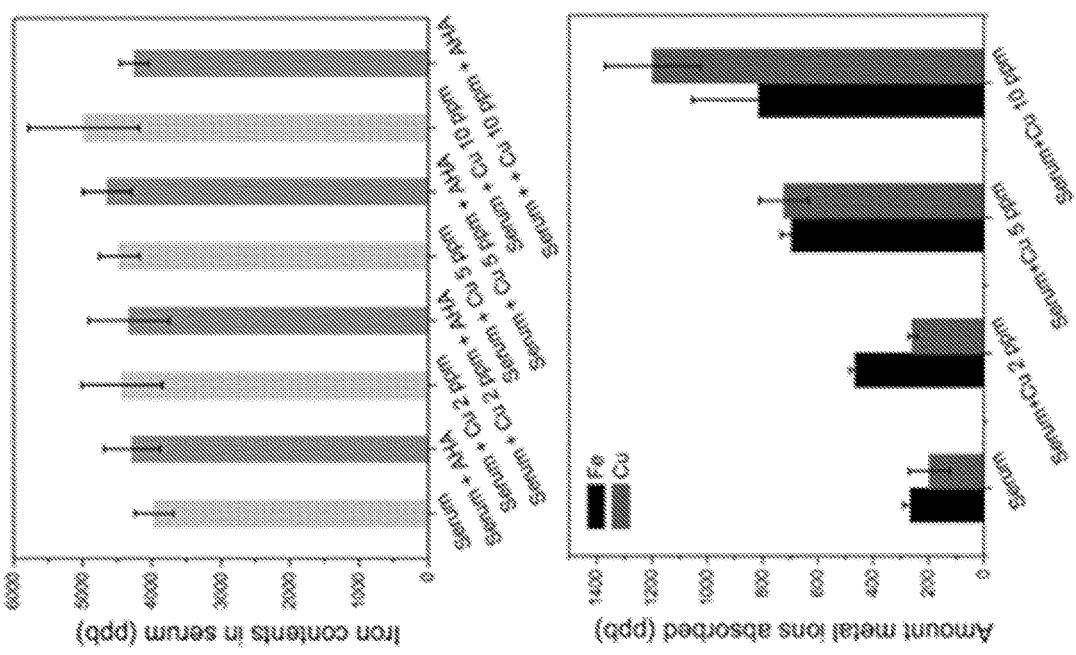
Figure 23A:
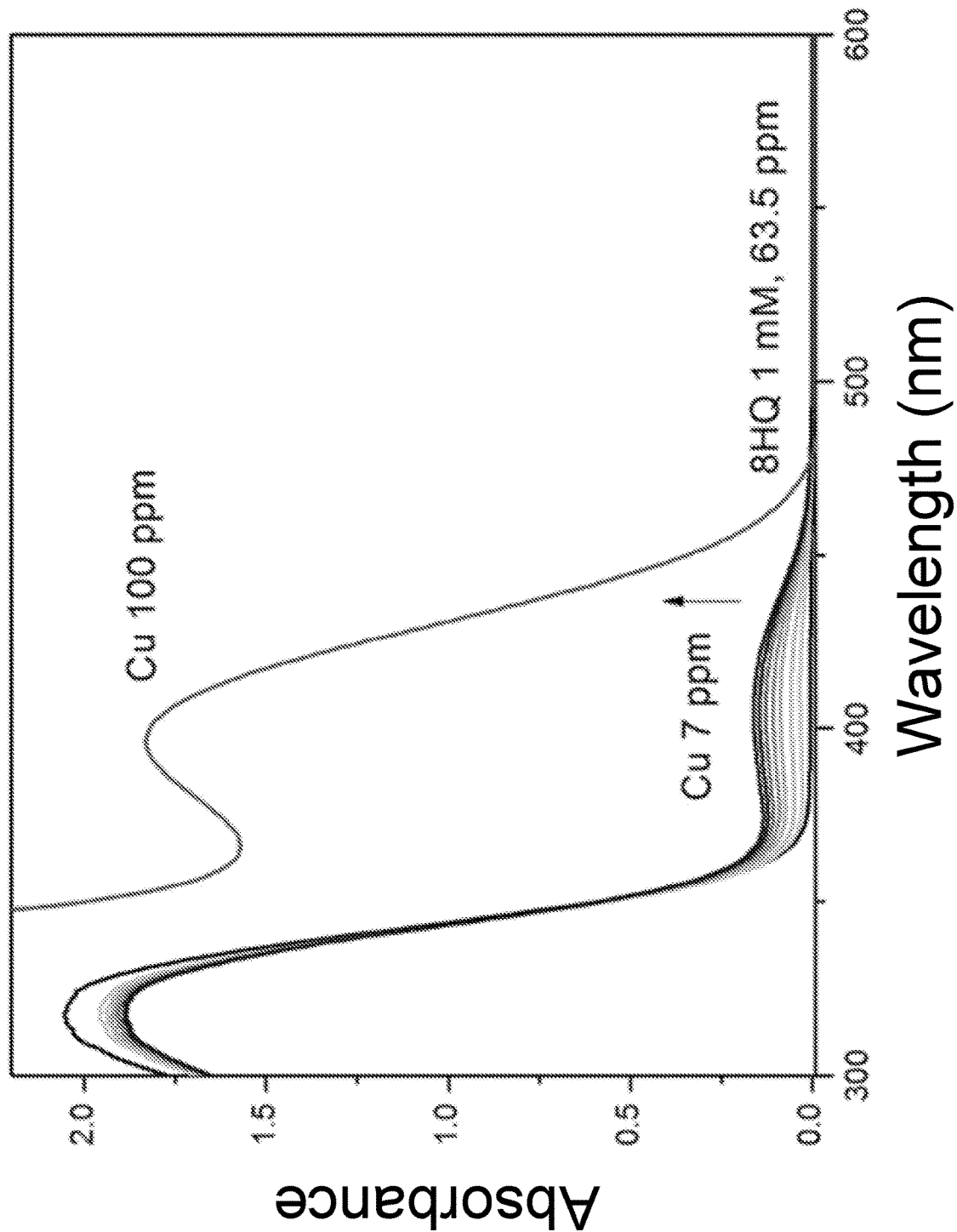
FIG. 23A-FIG. 23F illustrate the detection limits (three-sigma method 3σ/k) of 8-hydroxyquinoline (1 mM) in DMSO (FIG. 23A and FIG. 23B), serum (FIG. 23C and FIG. 23D), and urine (FIG. 23E and FIG. 23F) were calculated to be 186, 756, and 552 ppb, respectively.
Figure 23B:
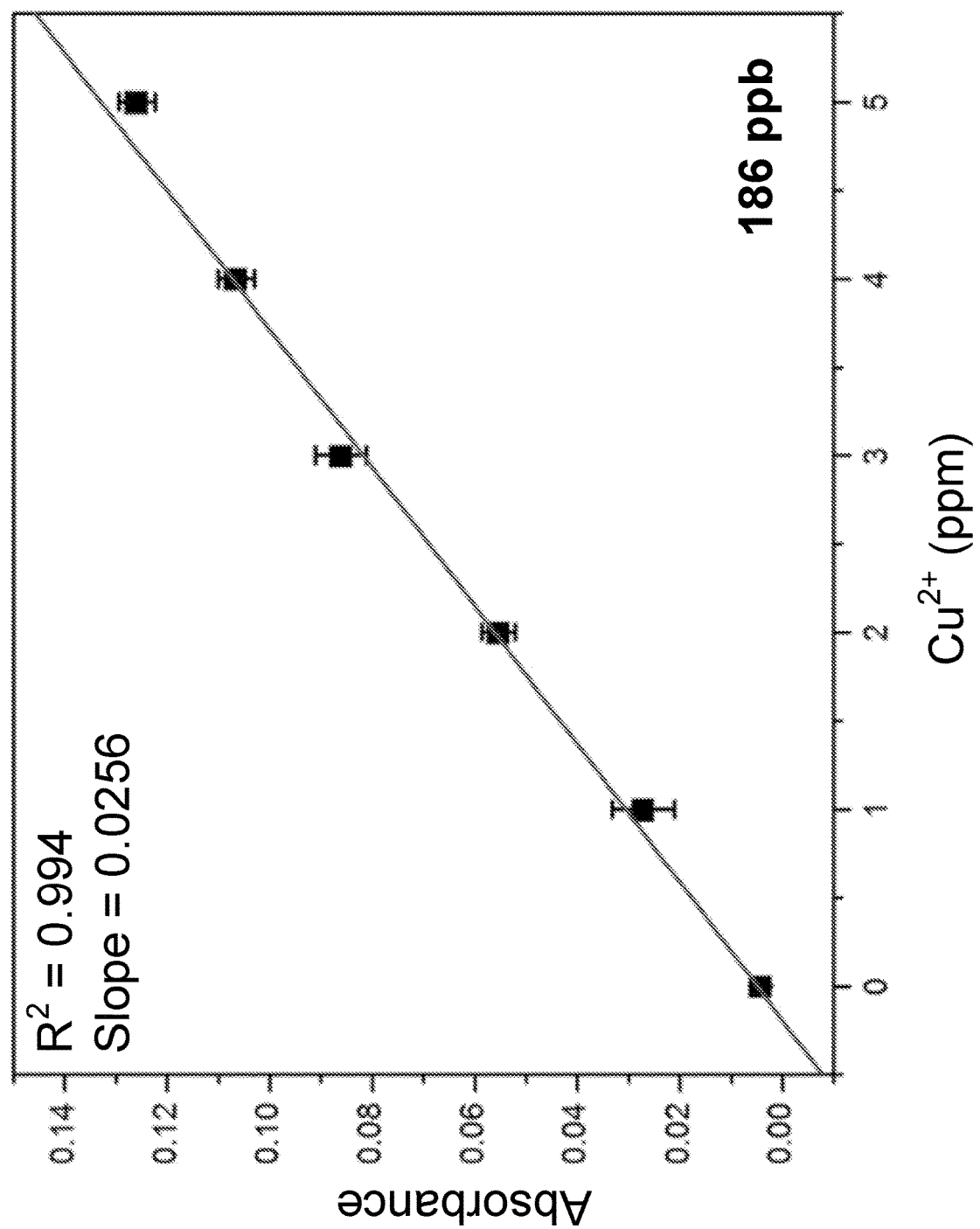
Figure 23C:
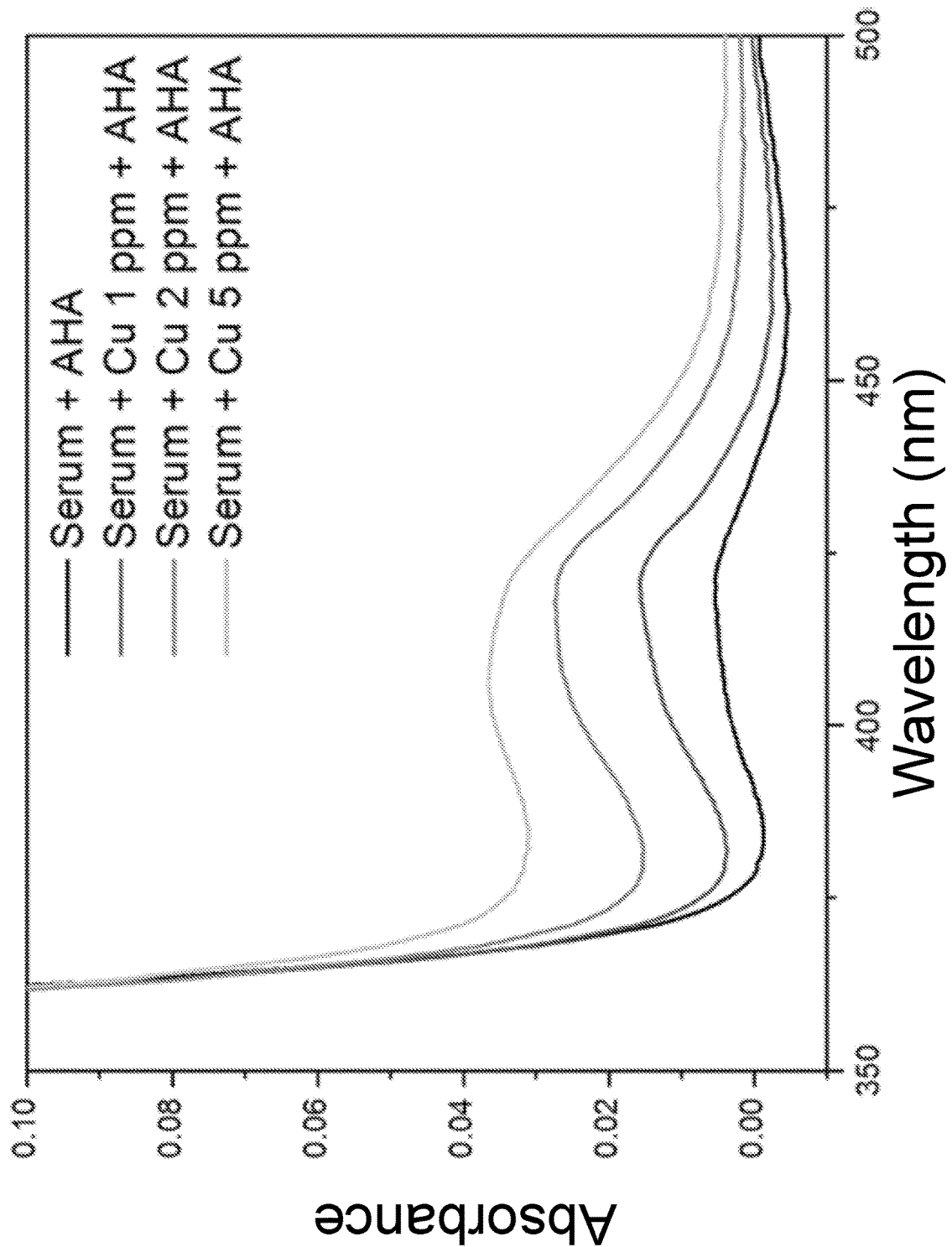
Figure 23D:
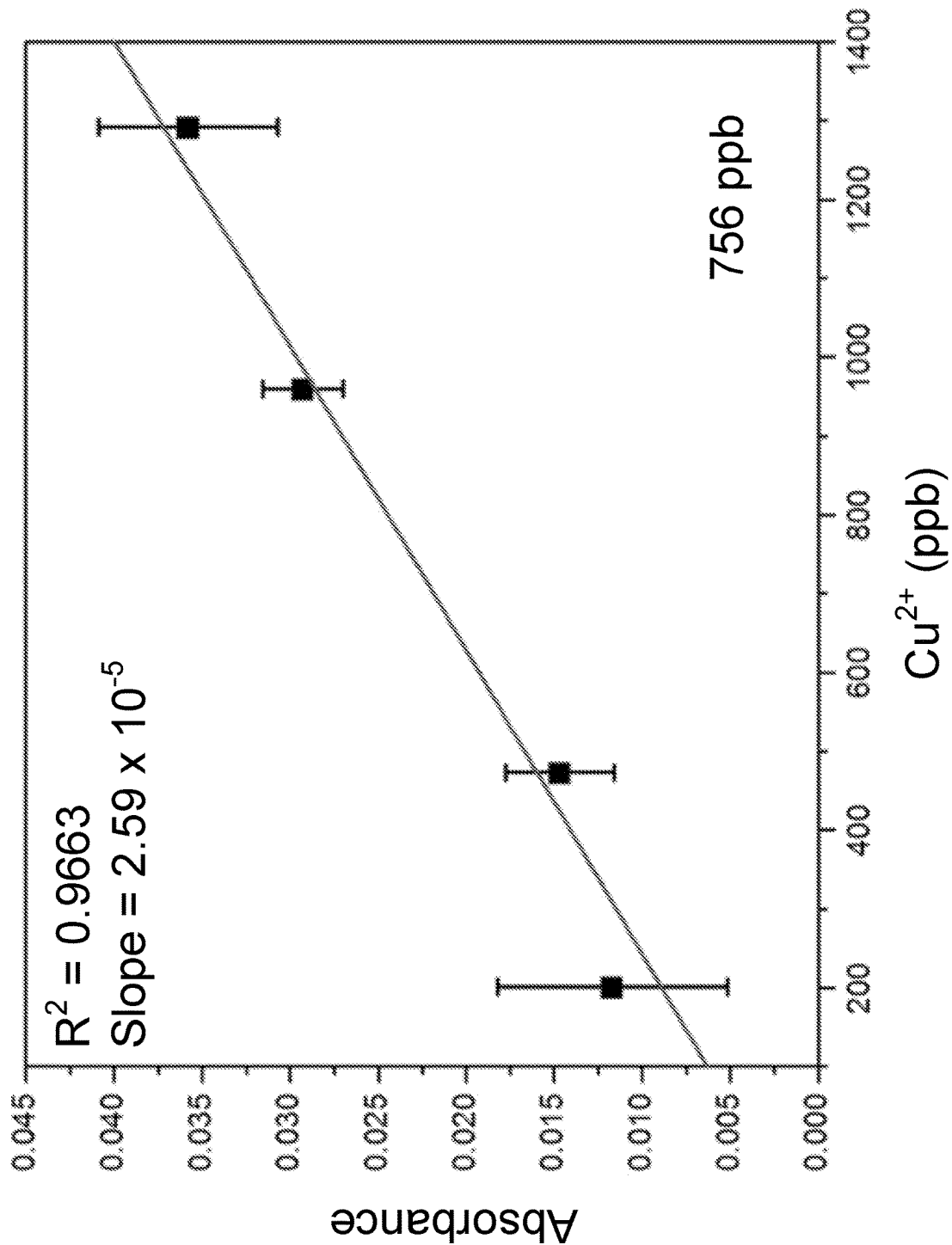
Figure 23E:
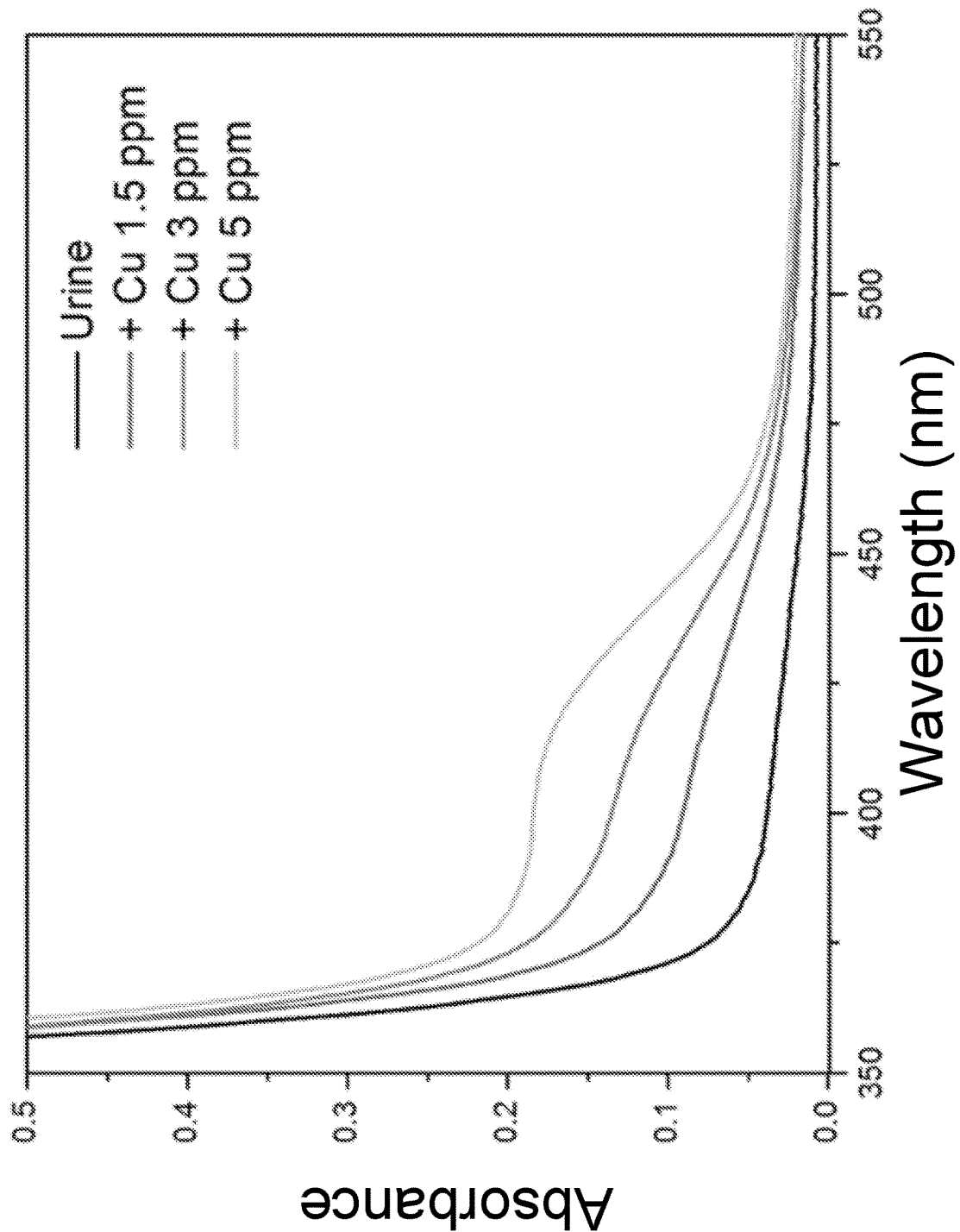
Figure 23F:
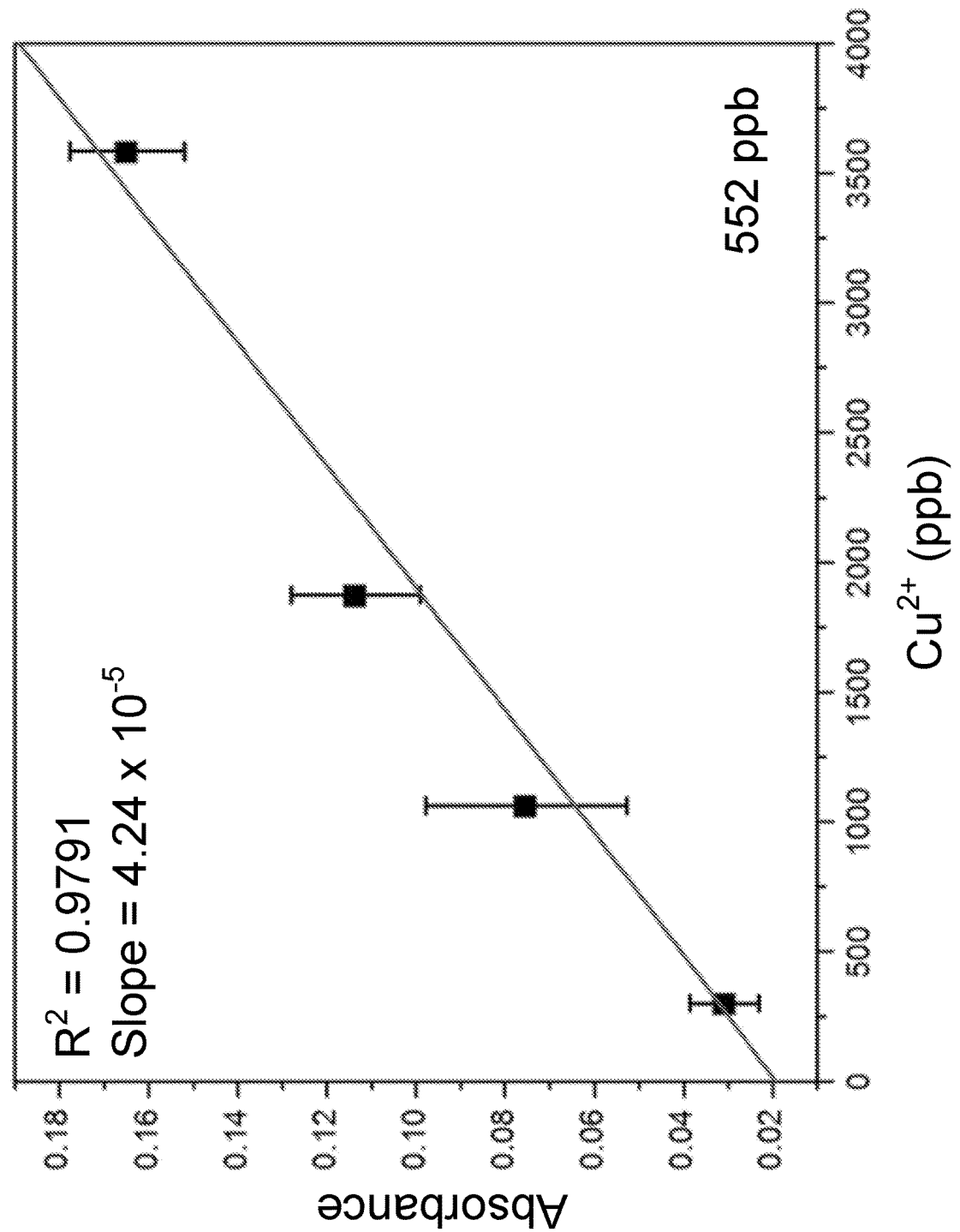

PAF-1-SMe shows high selectivity for copper over other biologically relevant metal ions with minor background from only iron(II) (FIG. 2b). Moreover, a direct competition assay revealed that PAF-1-SMe binds copper(II) much more tightly than iron(II) (FIG. 19), suggesting its potential utility for selective copper capture in biological and environmental samples.

Copper Capture and Detection in Biofluids.

Figure 3A:
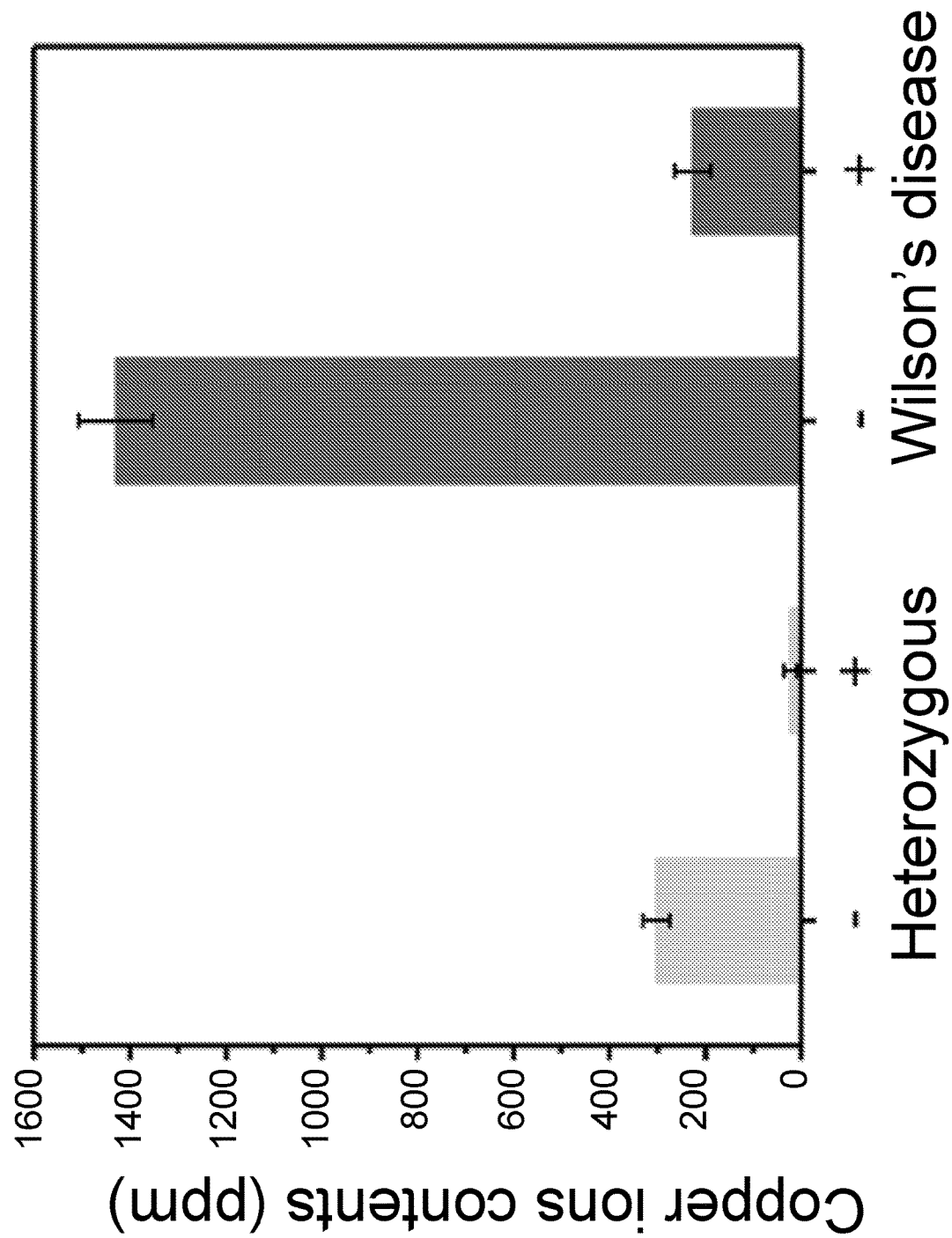
FIG. 3A illustrates Urine samples (1 mL) from 14-week old heterozygous (light gray bars) and Wilson's disease (dark gray bars) mice analyzed by ICP-MS before (−) and after (+) exposure to 2 mg of PAF-1-SMe.
Figure 3B:
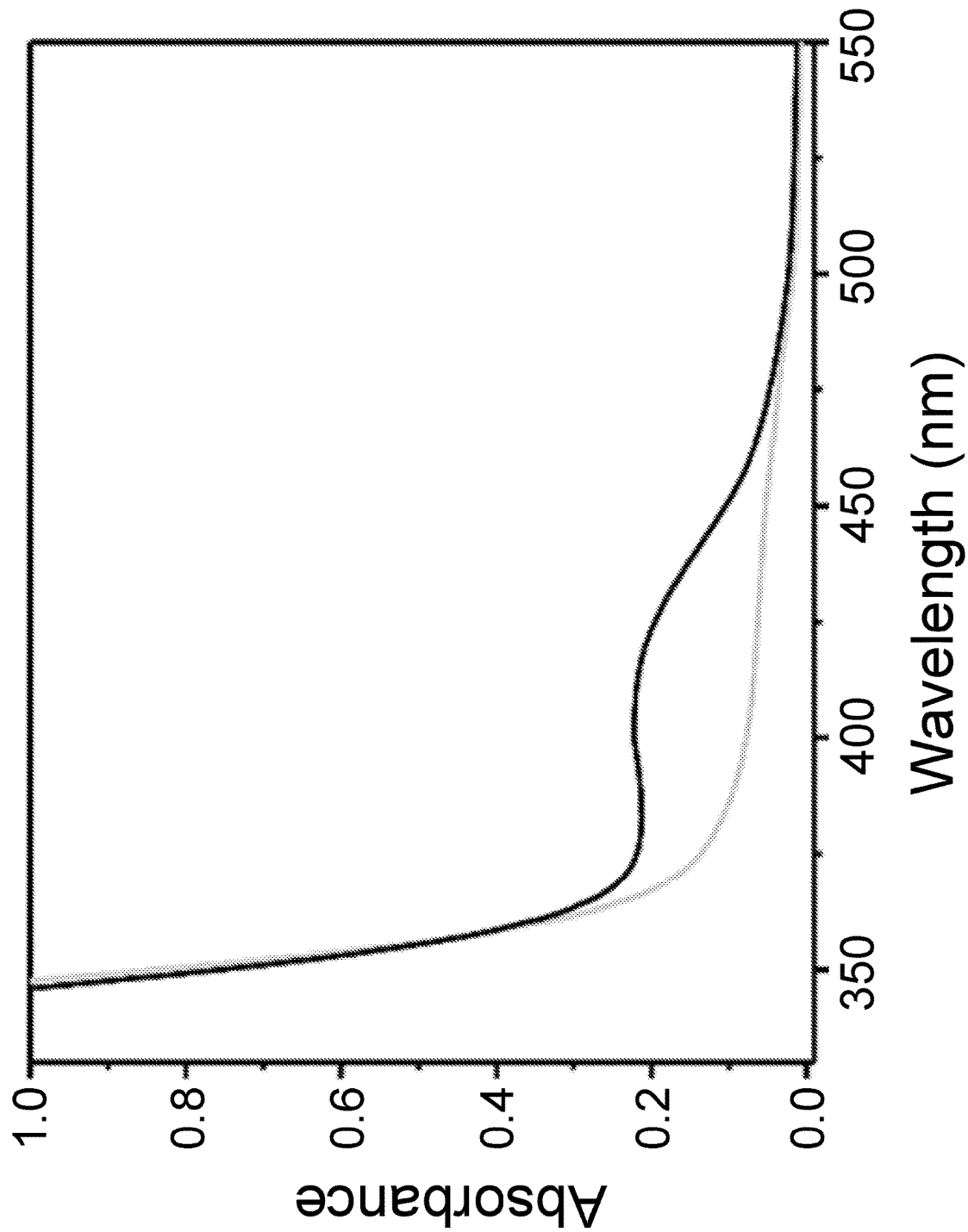
FIG. 3B Absorption spectra after 8-hydroxyquinoline addition to dried PAF-1-SMe with DMSO washes applied to heterozygous (light gray) and Wilson's disease (dark gray) urine specimens.
Figure 3C:
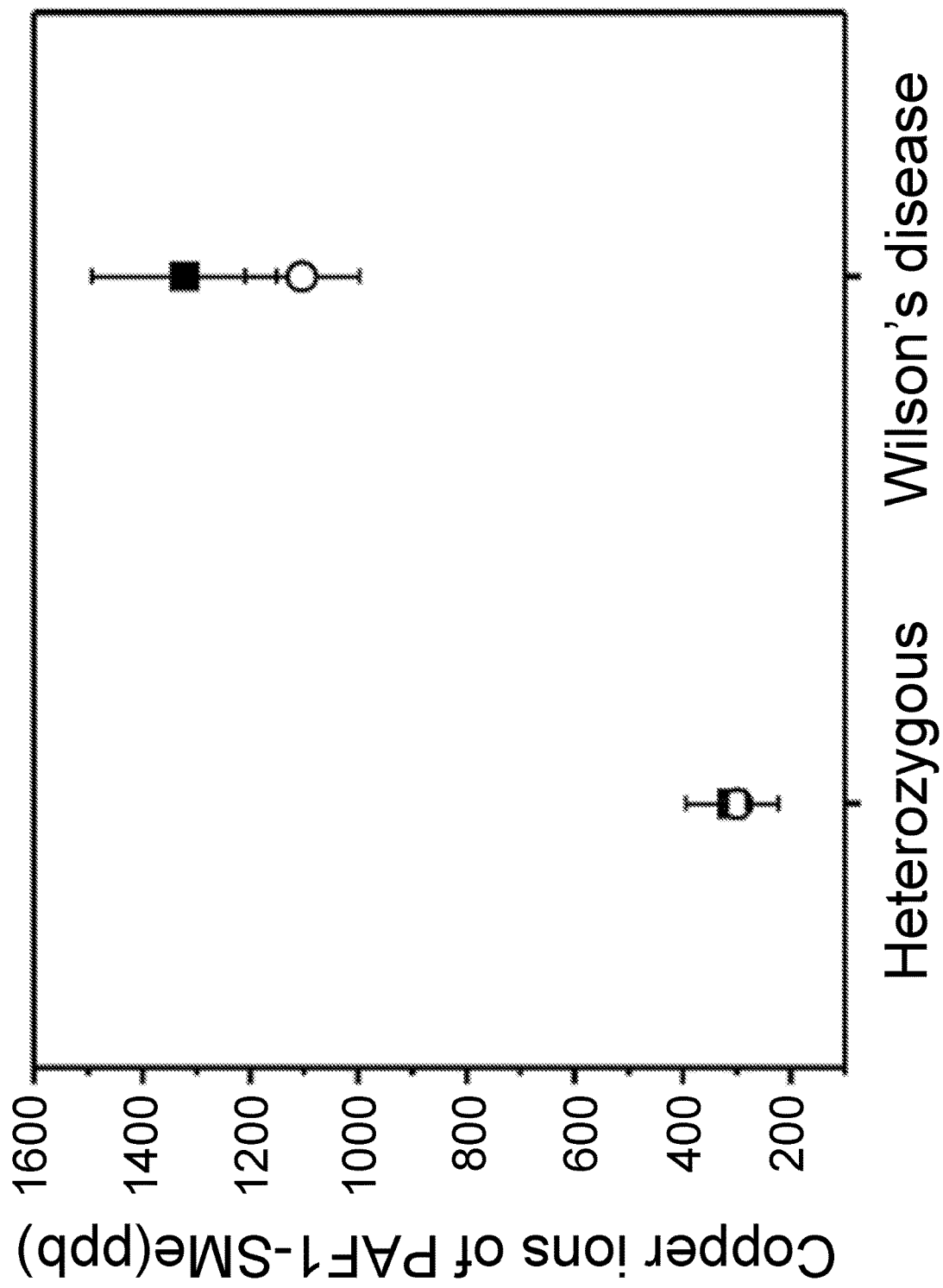
FIG. 3C Correlation between direct copper measurements by ICP-MS (open circles) versus calculated copper levels from 410-nm light absorption using 8-hydroxyquinoline as an indicator (black filled squares)
Figure 3D:
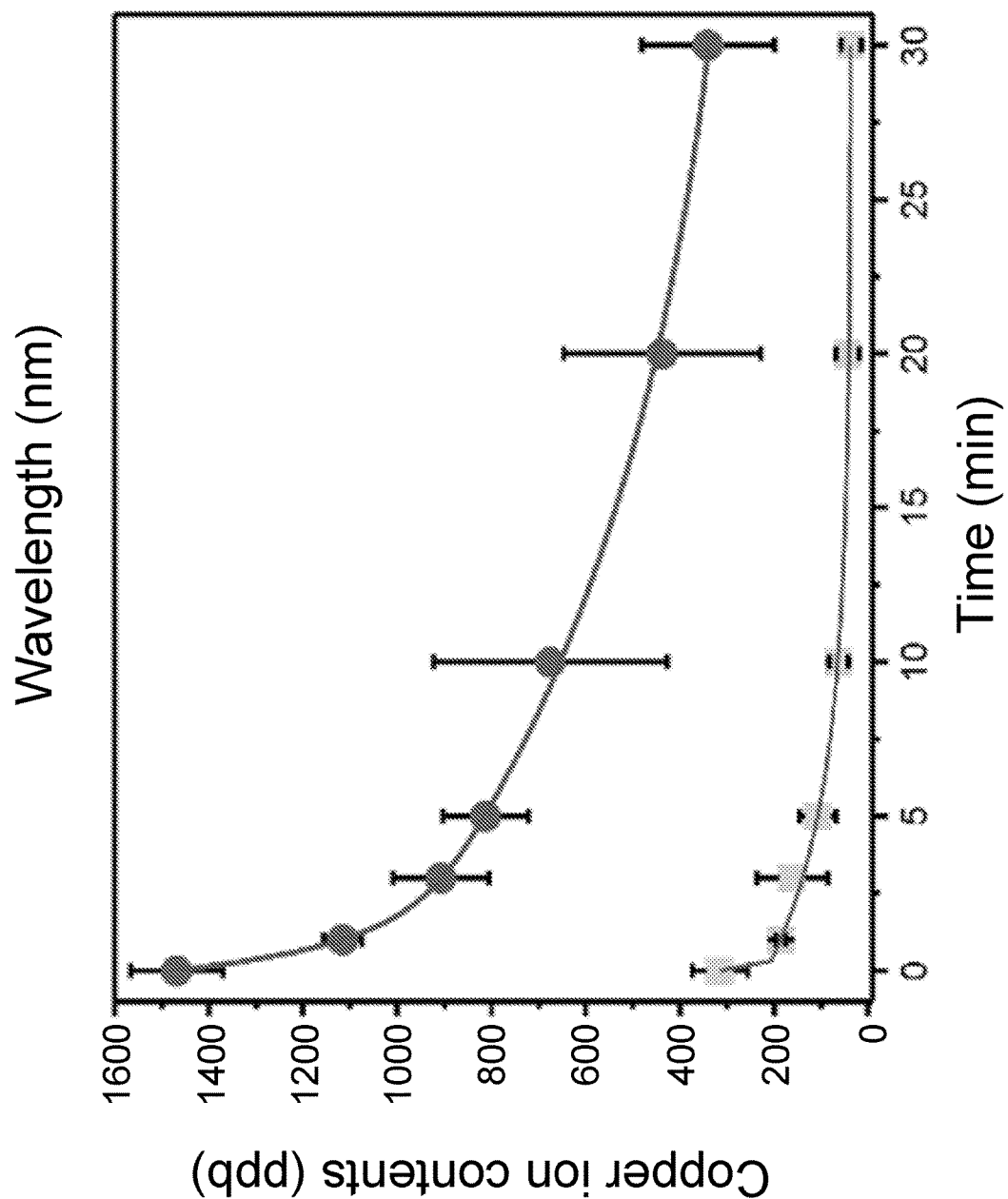
FIG. 3D Real time copper uptake of PAF-1-SMe in the urine samples of heterozygous (light gray) and Wilson's disease mice (dark gray) measured at 1, 3, 5, 10, 20, and 30 min intervals and fitted with the double exponential decay model: $y=A_1 \cdot \exp(-x/t_1)+A_2 \cdot \exp(-x/t_2)$; $<\tau_{Wilson's\ disease}>=15.9$ min and $<\tau_{Heterozygous}>=5.4$ min (lines connecting error bars).

After demonstrating the ability of PAF-1-SMe to capture copper with good affinity and selectivity in aqueous buffer, we examined its performance in biofluid samples, with specific application as part of a potential diagnostic tool for Wilson's disease. Initial ICP-MS characterization of urine samples from 14-week old Wilson's disease and healthy heterozygous control mice revealed a much greater urine copper level for the disease model (1420 ppb versus 295 ppb Cu, respectively, FIG. 3a). See, Gray et al., 2012, *PloS One* 7, e38327; Lech et al., 2007, *Clin. Toxicol.* 45, 688-694; Langner and Denk, 2004, *Virchows Arch* 445, 111-118, each of which is hereby incorporated by reference. The urine samples were accordingly treated with PAF-1-SMe, which resulted in successful capture of 1195 ppb copper from the Wilson's disease mice compared to 269 ppb for the control sample (capture efficiencies of 84% and 91%, respectively, FIG. 3a). Thus, PAF-1-SMe is capable of extracting copper directly from biofluid samples and importantly distinguishing between healthy and diseased mouse models. As further improvement of this diagnostic, we sought to identify the adsorbed copper concentration using a colorimetric agent, thus obviating the need for expensive ICP-MS or related instrumentation. We chose to apply 8-hydroxyquinoline (8-HQ), which undergoes a distinct color change upon copper binding from colorless (315 nm absorption, $\varepsilon = 1.95 \times 10^3$ M$^{-1}$ cm$^{-1}$) to green (410 nm absorption, $\varepsilon = 1.86 \times 10^3$ M$^{-1}$ cm$^{-1}$) by formation of a Cu(II)-8-HQ complex. See, Zhu et al., 2012, *Talanta.* 93, 55-61; Park et al., 2010, *Dyes and Pigments* 87, 49-54; and Yetisen et al., 2015, *Anal. Chem.* 87, 5101-5108, each of which is hereby incorporated by reference. To examine whether 8-HQ could bind copper captured within PAF-1-SMe, a solution of 8-HQ in DMSO was added to dried samples of PAF-1-SMe that had been exposed to urine from Wilson's disease or healthy control mice. Indeed, PAF-1-SMe copper capture from unprocessed urine samples followed by treatment with 8-HQ led to a visible change in the absorbance at 410 nm for the Wilson's disease murine models, which was sufficient to distinguish them from the heterozygous mice. (FIG. 3b). Calculation of the amount of copper adsorbed by PAF-1-SMe using the 410 nm absorbance peak as a standard also provided a good correlation with direct copper measurements by ICP-MS (FIG. 3c). Furthermore, PAF-1-SMe adsorbed copper completely from the urine of heterozygous and Wilson's disease mice in ~30 min and showed substantially different uptake in as little as 1 min (FIG. 3d), suggesting that these materials can be employed at shorter timescales.

Figure 4A:
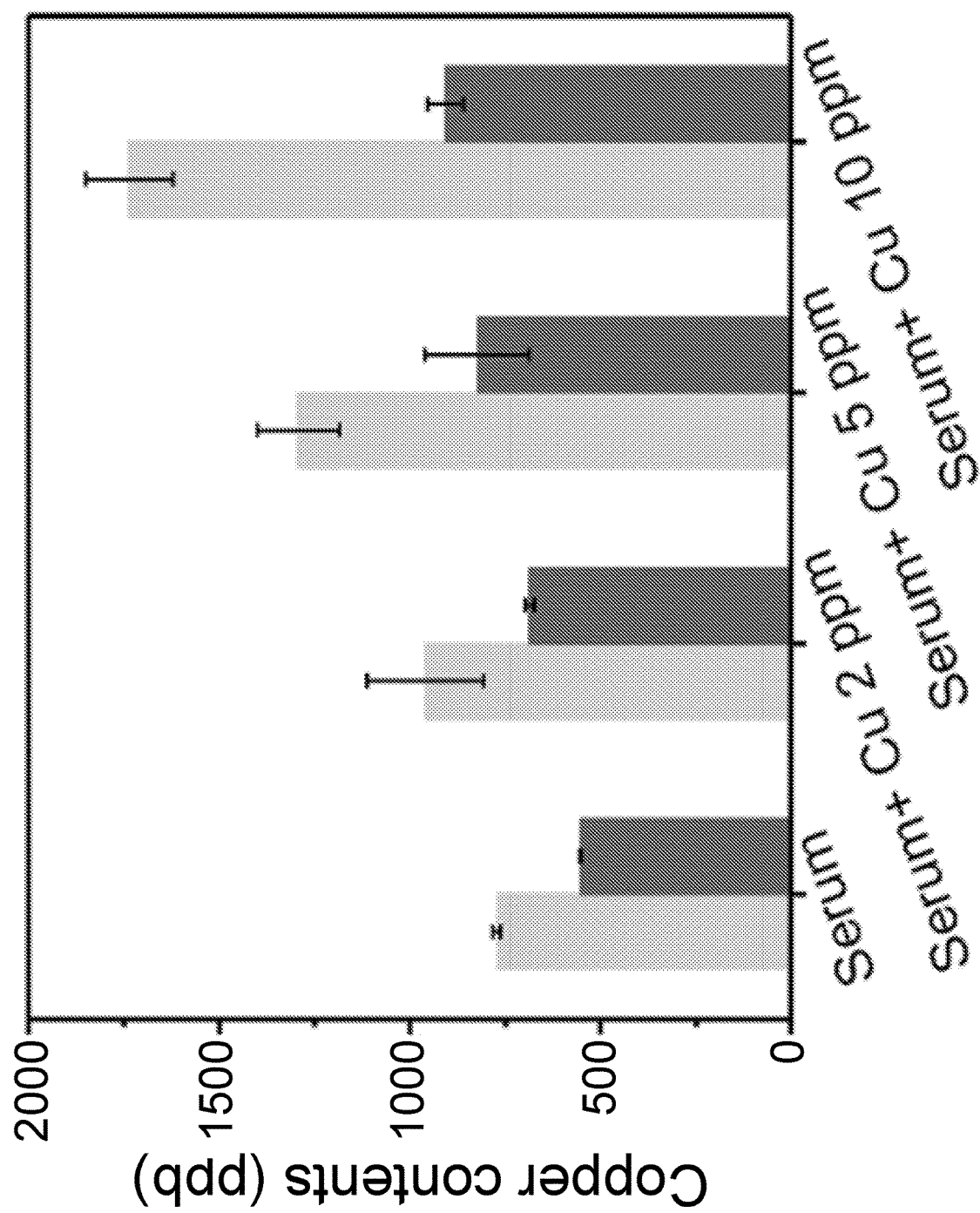
FIG. 4A illustrates porcine serum samples (4 mL) with varying amounts of exogenous copper analyzed by ICP-MS before (light grey bars) and after (black bars) addition of PAF-1-SMe.
Figure 4B:
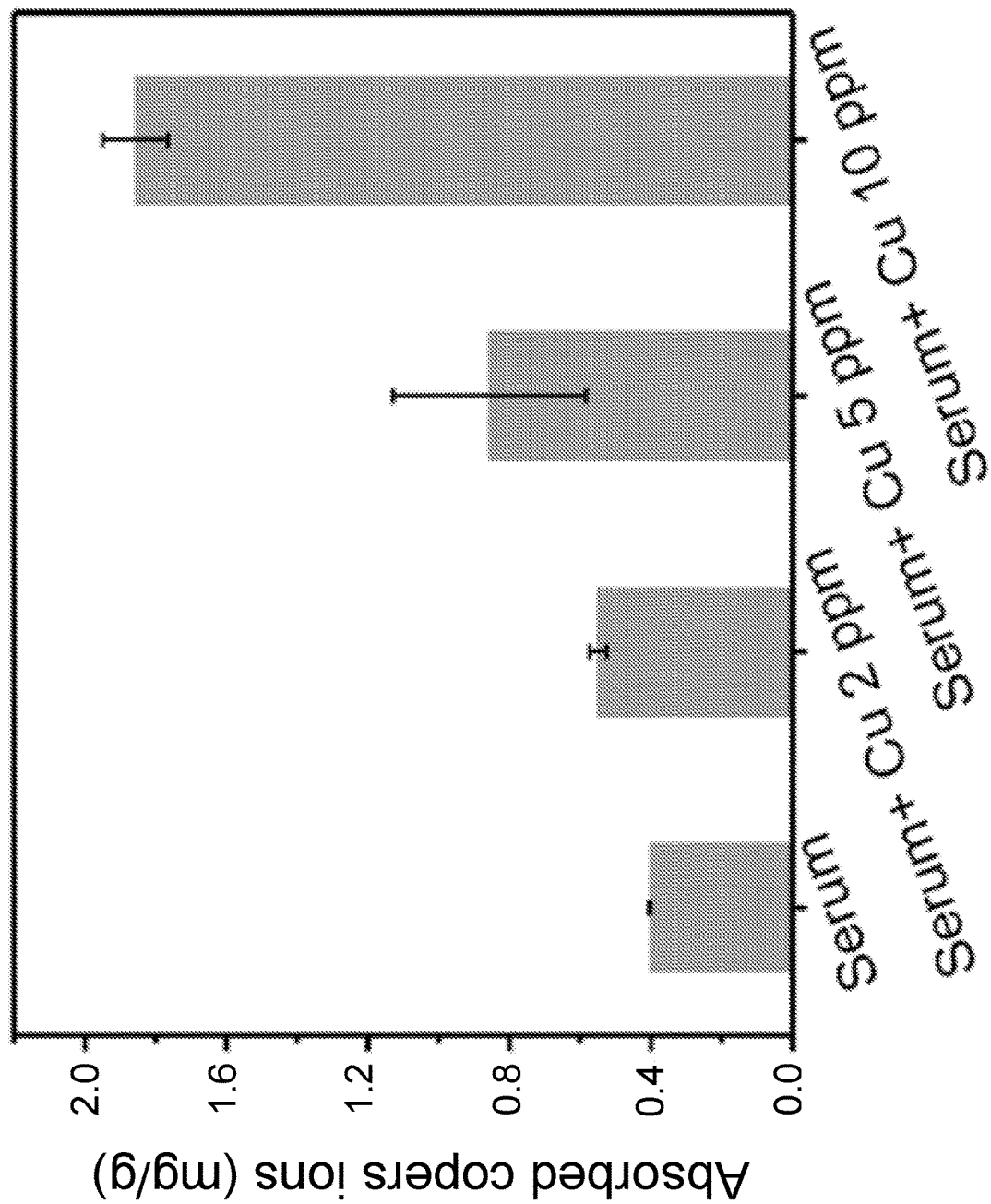
FIG. 4B dose-dependent adsorption of copper by PAF-1-SMe from serum samples.
Figure 4C:
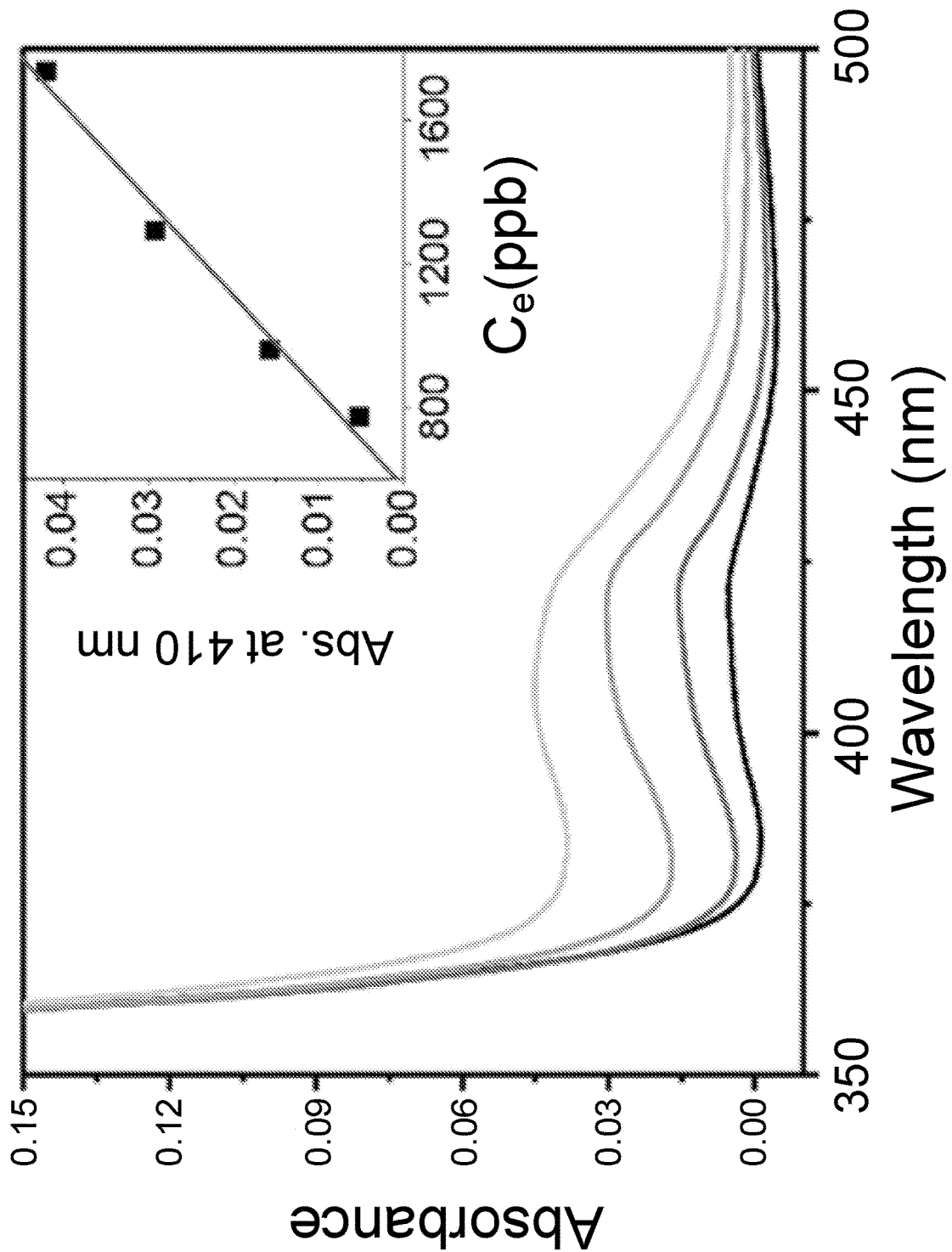
FIG. 4C absorption spectra after addition of 8-hydroxyquinoline to dried PAF-1-SMe with one DMSO wash applied to serum specimens with 0, 2, 5, and 10 ppm of exogenous copper; (Inset) Calibration curve showing dependence of absorbance at 410 nm on initial copper concentration for each sample.
Figure 4D:
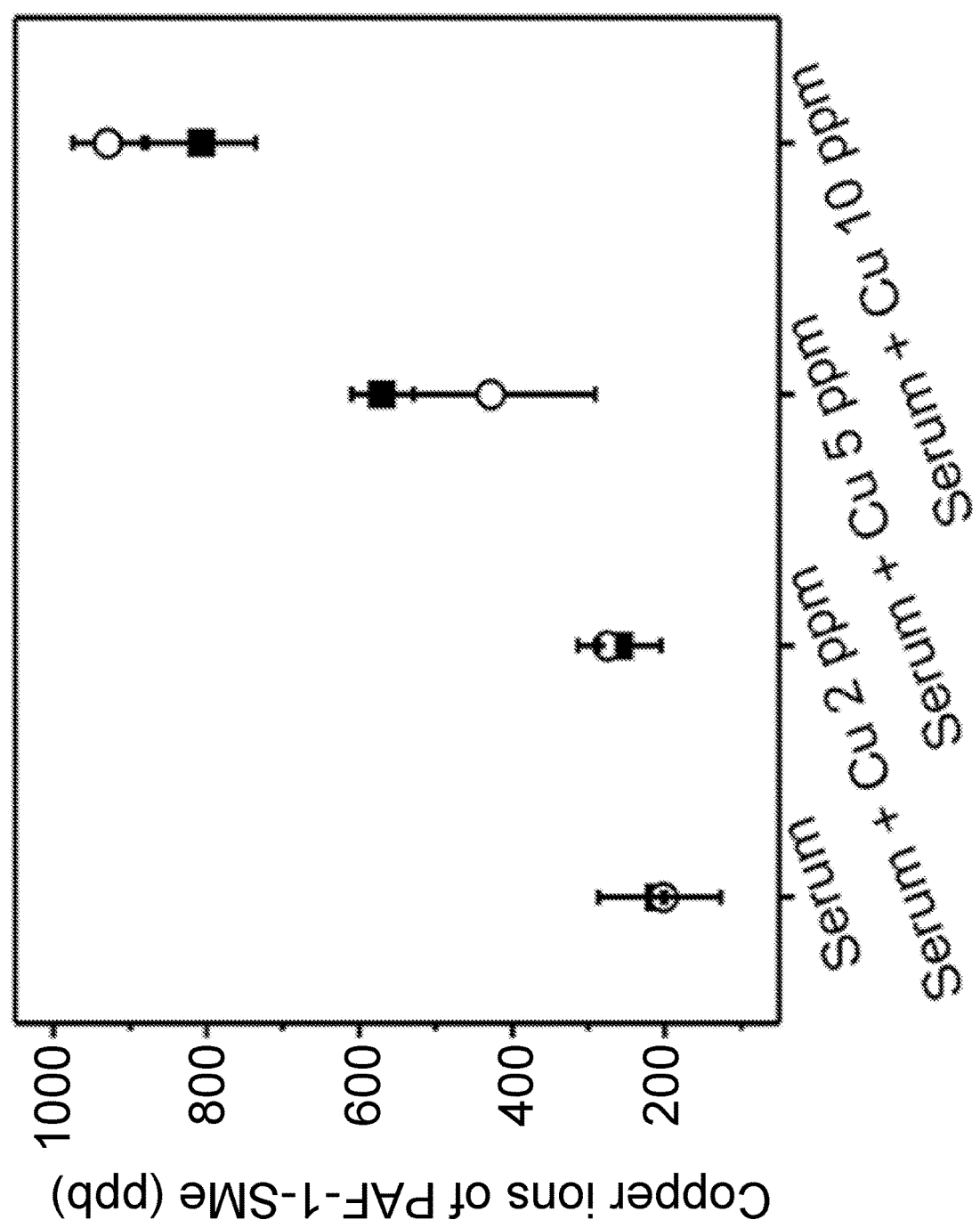
FIG. 4D comparison of direct copper measurements by ICP-MS (open circles) and calculated copper levels from absorbance at 410 nm using 8-hydroxyquinoline as an indicator (black filled squares) in accordance with some embodiments.
Figure 5:
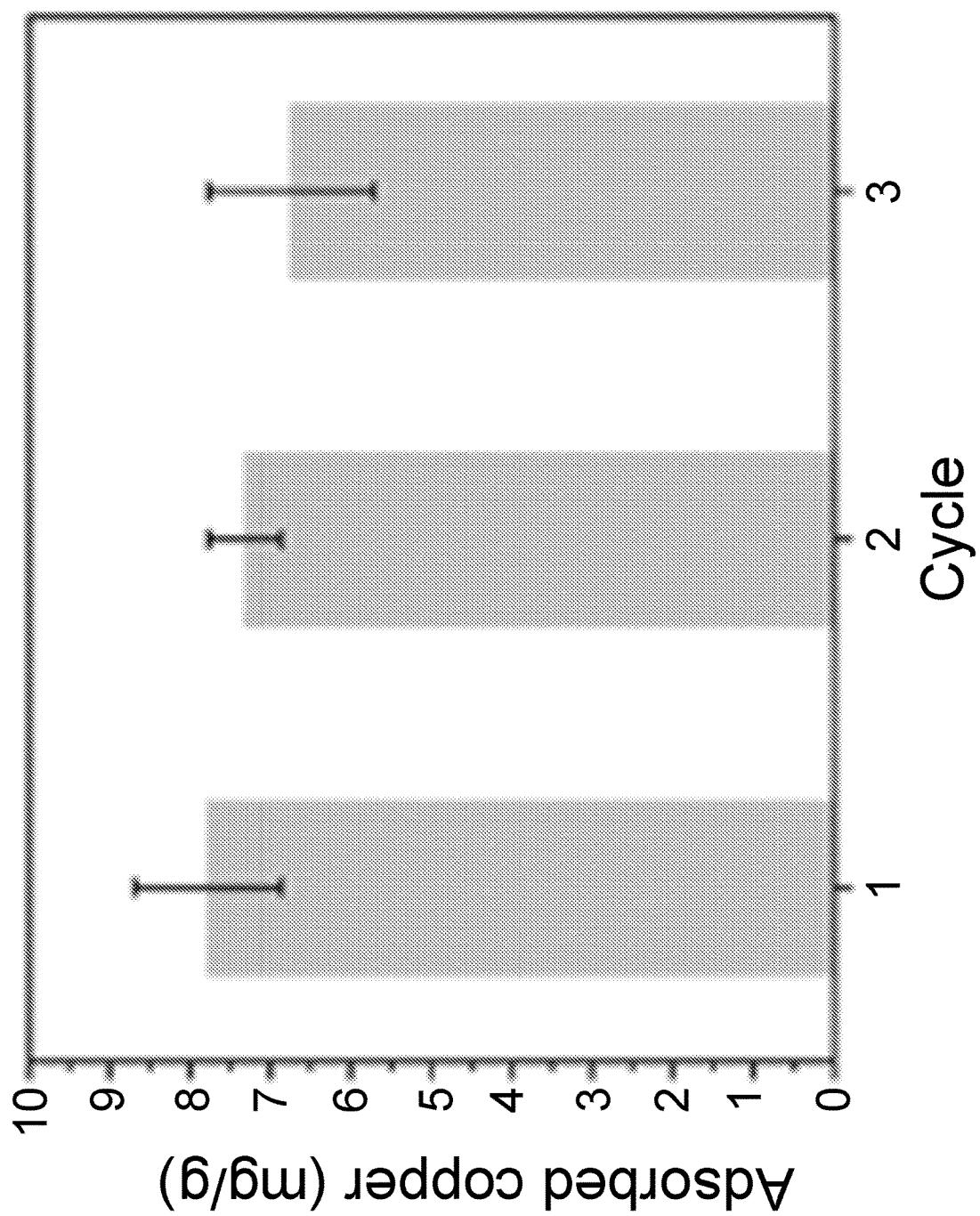
FIG. 5 illustrates comparison of copper uptake (10 ppm in 200 mM HEPES buffer, pH 6.7) by freshly synthesized PAF-1-SMe (cycle 1) with PAF-1-SMe regenerated twice by 8-hydroxyquinoline (1 mM) in DMSO (cycles 2 and 3) in accordance with some embodiments.
Figure 24:
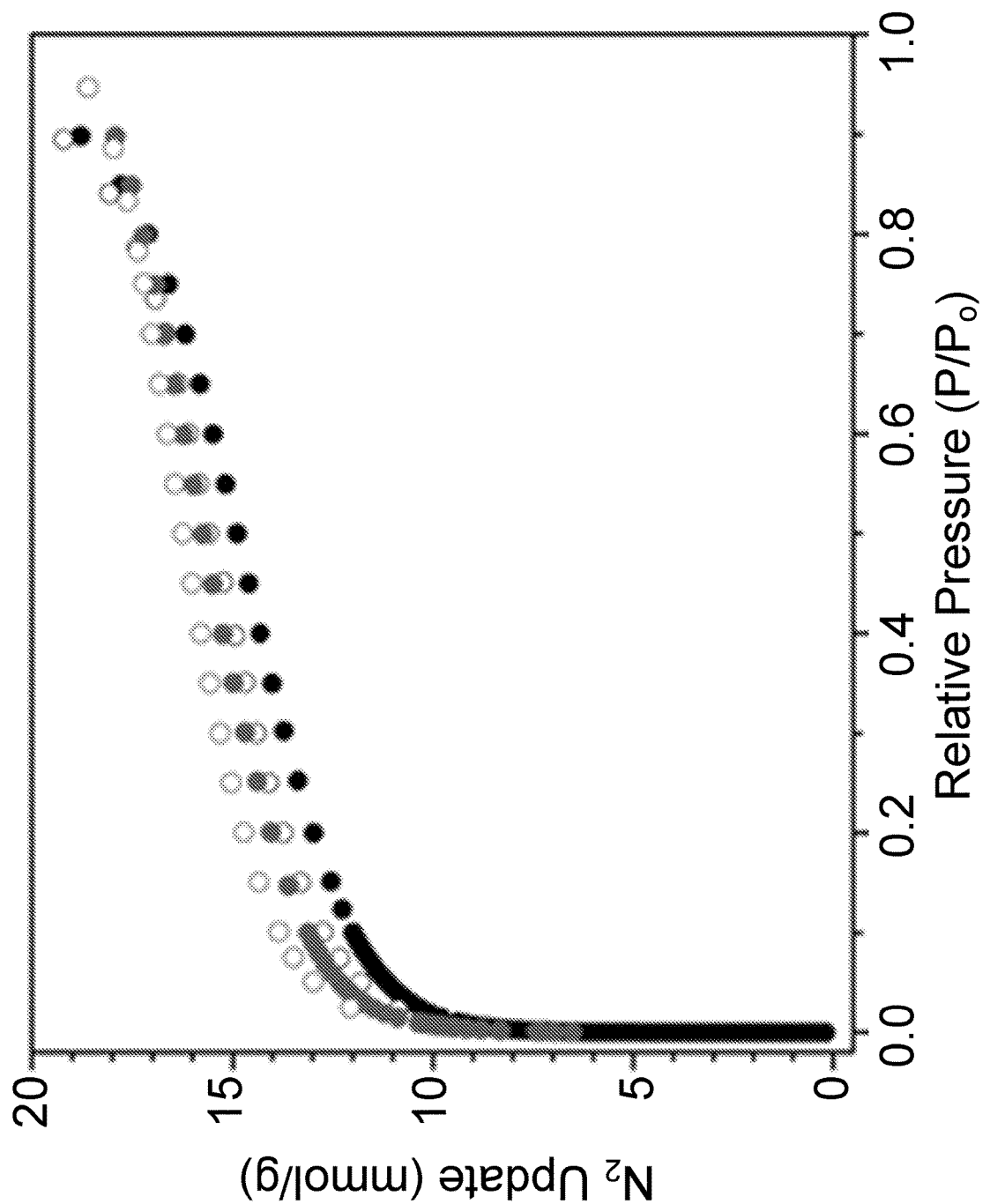
FIG. 24 illustrates $N_2$ sorption isotherms (77 K) of freshly synthesized PAF-1-SMe (black) and regenerated PAF-1-SMe (red) which was treated with biofluid and then followed by 8-HQ (100 mM).

We also evaluated the performance of PAF-1-SMe for the detection of copper in serum, which is notably a more complex biofluid compared to urine with iron concentrations approximately 5 times greater than that of copper. See, Afsana et al., 20014, *Biosci. Biotechnol. Biochem* 68, 584-592; and Ranganathan et al., 2011 *Blood* 118, 3146-3153, each of which is hereby incorporated by reference. We used porcine serum sources owing to limitations in obtaining sufficient amounts of murine specimens required for this first-generation assay. Exogenous copper was added to the samples to simulate elevated serum free copper levels observed in patients with Wilson's disease. See Brewer, *Wilson's disease A Clinician's Guide to Recognition, Diagnosis, and Management*, Springer Science+Business Media New York, 2001, Print; Huster, 2010, *Best Practice & Research Clinical Gastroenterology* 24, 531-539; Ala et al., 2007, *Lancet.* 369, 397-408; Ferenci, 2006, *Hum. Genet.* 120, 151-159; and Bandmann, 2015, *Lancet* 14, 103-113, each of which is hereby incorporated by reference. Although we observed that PAF-1-SMe could preferentially bind copper over iron(II), it also absorbed a significant amount of iron in unprocessed serum. This iron uptake disturbed the subsequent colorimetric assay with 8-HQ due to an interfering signal from the 8-HQ-iron(II) complex (FIG. 10). To reduce iron interference, we pre-treated the serum sample with acetohydroxamic acid (AHA), a high-affinity iron chelator that shows little interaction with copper. See Farkas et al., 1999, *Polyhedron* 18, 2391-2398; Witte et al., 2000, *Free Radic. Biol. Med.* 28, 693-700; Maekawa and Koshijima, 1990, *J. Appl. Polym. Sci.* 40, 1601-1613, each of which is hereby incorporated by reference. Indeed, PAF-1-SMe shows dose-dependent copper capture for exogenous copper addition over a range of 0-10 ppm (FIGS. 4a, 4b). Analogous to the urine sample results, with AHA pretreatment 8-HQ can also serve as a colorimetric indicator when coupled with PAF-1-SMe for direct copper capture from serum and the 8-HQ assay revealed a positive linear dependence of the absorbance at 410 nm with increasing serum copper concentration (FIG. 4c, inset). As also demonstrated for the urine samples, copper levels calculated from the 410 nm absorption was in good agreement with direct ICP-MS measurements (FIG. 4d). Using a three-sigma method (36/k), we determined that the detection limit for this PAF-1-SMe/8-HQ assay is 186 ppb in DMSO, 552 ppb in urine, and 756 ppb in serum (FIG. 23). On balance, we note that AHA pretreatment does add an extra step to the protocol for serum compared to urine, but this methodology still avoids expensive instrumentation and sample processing. Indeed, this AHA pretreatment followed by application of PAF-1-SME/8-HQ radically simplifies the traditional method to detect copper by ICP-MS, which includes boiling in nitric acid for digestion, centrifugation, and filtration. See Razmandeh et al., 2014, *J. Diabetes. Metab. Disord.* 13:43/1-43/6; Vanhoe, 1989, *Anal. Chem.* 61, 1851-1857, each of which is hereby incorporated by reference. Importantly PAF-1-SMe retained structure and porosity and maintained a high effective copper capture capacity after regeneration with 8-HQ (FIG. 5 and FIG. 24).

General Methods.

Starting materials and reagents were purchased from Sigma-Aldrich and used as received without further purification. Tetrakis(4-bromophenyl)methane was prepared following the procedure reported in the literature. See, Lu et al., 2010, *Chem. Mater.* 22, 5964-5972; and (b) Ben et al., 2009, *Angew. Chem. Int. Ed.* 48, 9457-9460, which is hereby incorporated by reference. All reactions were performed under a nitrogen or argon atmosphere and in dry solvents, unless otherwise stated.

Gas Adsorption Isotherms.

Gas adsorption isotherms were measured using a Micromeritics ASAP 2020 or 2040 instrument. Samples were transferred to a pre-weighed glass analysis tube, which was capped with a Transeal, and were evacuated on the ASAP until the outgas rate was less than 3 µbar/min. Ultrahigh-purity grade (99.999%) nitrogen was used for gas adsorption measurements. Nitrogen isotherms were obtained using a 77 K liquid-$N_2$ bath and used to determine the surface areas and pore volumes using the Micromeritics software, assuming a value of 16.2 $Å^2$ for the molecular cross-sectional area of $N_2$. Pore-size distributions were calculated using the density functional theory method with a QSDFT adsorption branch model of $N_2$ at 77 K adsorbed in carbon with slit/cylindrical/spherical pores, as implemented in the Quantachrome VersaWin software.

Infrared Spectra.

Infrared spectra were obtained on a Perkin-Elmer Spectrum 100 Optica FTIR spectrometer furnished with an attenuated total reflectance accessory.

Thermal Gravimetric Analysis.

Thermal gravimetric analysis (TGA) data was collected at ramp rates of 5° C./min under flowing nitrogen using a TA Instruments TGA Q5000.

Diffraction Data.

Diffraction data were collected with 0.2° steps using a Bruker AXS D8 Advance diffractometer equipped with Cu-Kα radiation (λ=1.5418 Å).

Scanning Electron Microscopy (SEM).

Scanning electron microscopy (SEM) samples of polymers were prepared by dispersing fine powders into methanol and drop casting onto a silicon chip. To dissipate charge, the samples were sputter coated with approximately 3 nm of Au (Denton Vacuum). Polymers were imaged at 5 keV and 12 µA by field emission SEM (JEOL FSM6430).

Carbon, Hydrogen, Nitrogen, and Sulfur Elemental Analyses.

Carbon, hydrogen, nitrogen, and sulfur elemental analyses were obtained from the Microanalytical Laboratory at the University of California, Berkeley. Elemental analysis for chlorine was performed at Galbraith Laboratories.

Solid state NMR spectra. Solid state NMR spectra $^1H$-$^{13}C$ cross-polarization (CP) spectra were collected on a 7.05 Tesla magnet at $^{13}C$ frequency of 75.5 MHz under 10 kHz magic-angle spinning (MAS) condition. A Chemagnetics 4 mm H/X probe and a Tecmag Discovery spectrometer were used. The Hartmann-Hahn condition for CP experiments was obtained on solid adamantane, which is also a secondary reference of $^{13}C$ chemical shift (the methylene signal of adamantane was set to 38.48 ppm relative to TMS). Two pulse phase modulation (TPPM) proton decoupling scheme was used. The TPPM angle was 15 degree and the decoupling field strength was ~60 kHz. A contact time of 10 ms and a pulse delay of 4 s were used in CP experiments.

EPR.

EPR measurements were recorded at ambient temperature using an Active Spectrum X-band continuous wave spectrometer. The sweep was from 210 mT to 420 mT.

UV-Vis Spectroscopic Measurements.

UV-Vis spectroscopic measurements were performed in 100 mM HEPES buffer (pH 6.7). Absorption spectra were recorded using a Varian Cary 50 spectrophotometer and samples for absorption measurements were prepared in 1 cm×0.5 cm quartz cuvettes (1.4-mL volume, Starna).

Inductively Coupled Plasma-Mass Spectrometry.

Inductively coupled plasma-mass spectrometry (ICP-MS) was performed on samples that had been diluted into 2% nitric acid (made freshly from concentrated nitric acid (BDH Aristar Ultra) and MilliQ water) containing 20 ppb Ga internal standard (Inorganic Ventures, Christiansburg, Va.). The samples were analyzed on a ThermoFisher iCAP-Qc ICP-MS in Kinetic Energy Discrimination (KED) mode against a calibration curve of known metal concentrations (made from CMS-5, Inorganic Ventures, Christiansburg, Va.).

Synthesis of PAF-1-SMe.

Anhydrous 1,5-cyclooctadiene (cod, 1.05 mL, 8.32 mmol, Aldrich) was added to a solution of bis(1,5-cyclooctadiene) nickel(0) (2.25 g, 8.18 mmol, Aldrich) and dried 2,2'-bipyridyl (1.28 g, 8.18 mmol, Aldrich) in distilled DMF (100 mL, Aldrich) in a dry box. The mixture was heated at 80° C. for 1 h. Tetrakis(4-bromophenyl)methane (1 g, 1.57 mmol) was added to the purple solution and the mixture was stirred at 80° C. overnight to obtain a deep purple suspension. After cooling to room temperature, concentrated HCl was added to the mixture. The residue was filtered with washing with warm THF (100 mL), H$_2$O (100 mL), ethanol (100 mL), and CH$_3$Cl (100 mL) respectively, and dried in vacuum oven (170° C.) to give PAF-1 as an off white powder. A pressure flask was charged with PAF-1 (200.0 mg), paraformaldehyde (1.0 g), glacial AcOH (6.0 ml), H$_3$PO$_4$ (3.0 ml) and conc. HCl (20.0 ml). The flask was sealed and heated to 100° C. for 3 days. The resulting solid was filtered and washed with H$_2$O (500 mL), THF (100 mL), ethanol (100 mL), and CH$_3$Cl (100 mL) and then dried under vacuum oven (150° C.) to produce pale yellow solid of PAF-1-CH$_2$Cl. Subsequently, PAF-1-CH$_2$Cl was mixed with NaSCH$_3$ (1.2 g, 21.0 mmol, Aldrich) in 100 mL ethanol under N$_2$ and stirred at 70° C. for 3 days. The resulting solid was collected, washed with H$_2$O (100 mL), THF (100 mL), ethanol (100 mL), and CH$_3$Cl (100 mL), and then dried under vacuum oven (150° C.) to produce PAF-1-SMe as pale yellow powder. Elemental analysis found for PAF-1-SMe: 68.28% C, 5.68% H, 0.502% Cl, 9.60% S.

Structural Characterization of PAF-1, PAF-1-CH$_2$Cl, and PAF-1-SMe.

Figure 8B:
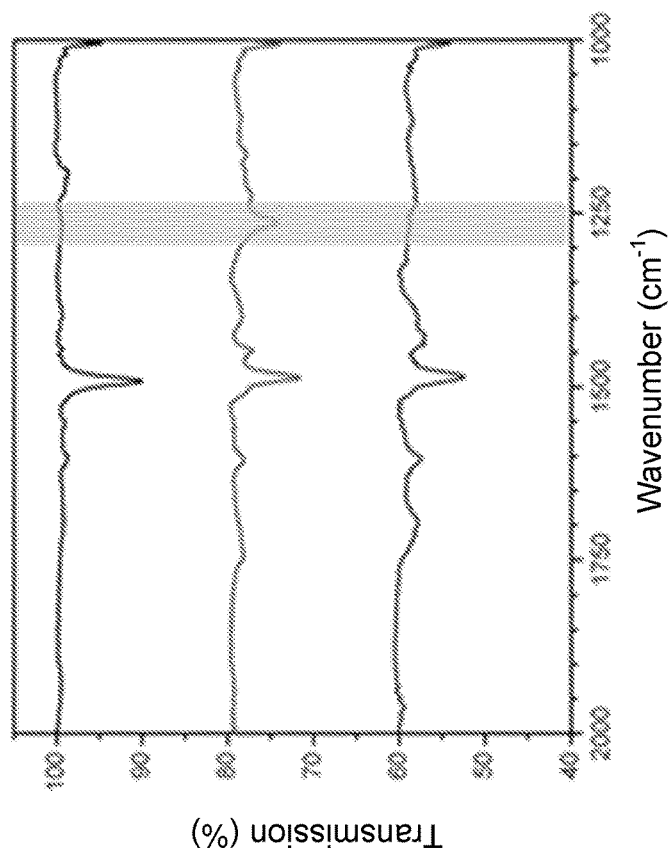
FIG. 8A and FIG. 8B illustrate FT-IR spectra of PAF-1, PAF-1-CH$_2$Cl, and PAF-1-SMe in accordance with some embodiments.
Figure 8A:
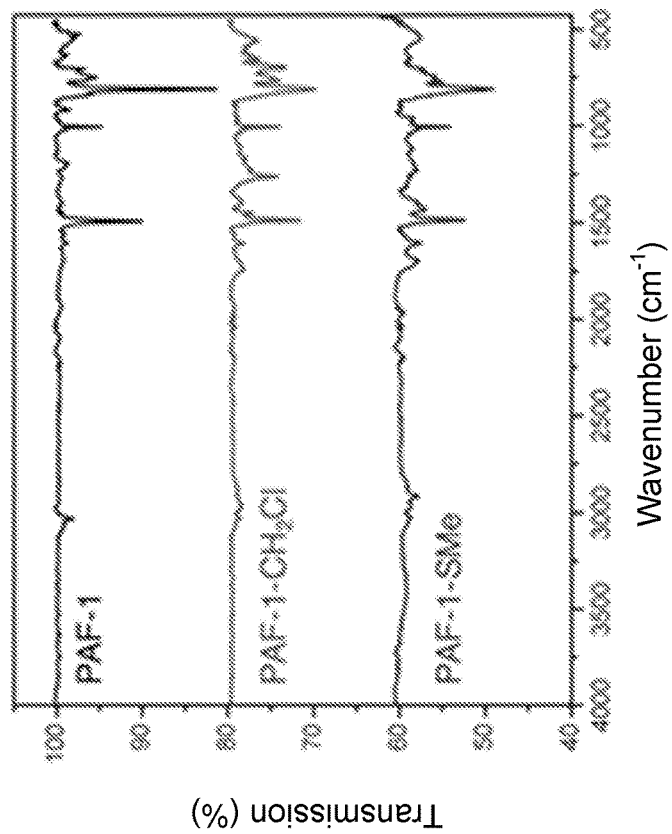

FIG. 8 illustrates (a,b) FT-IR spectra of PAF-1, PAF-1-CH$_2$Cl, and PAF-1-SMe in accordance with some embodiments.

Figures 9A, 9B:
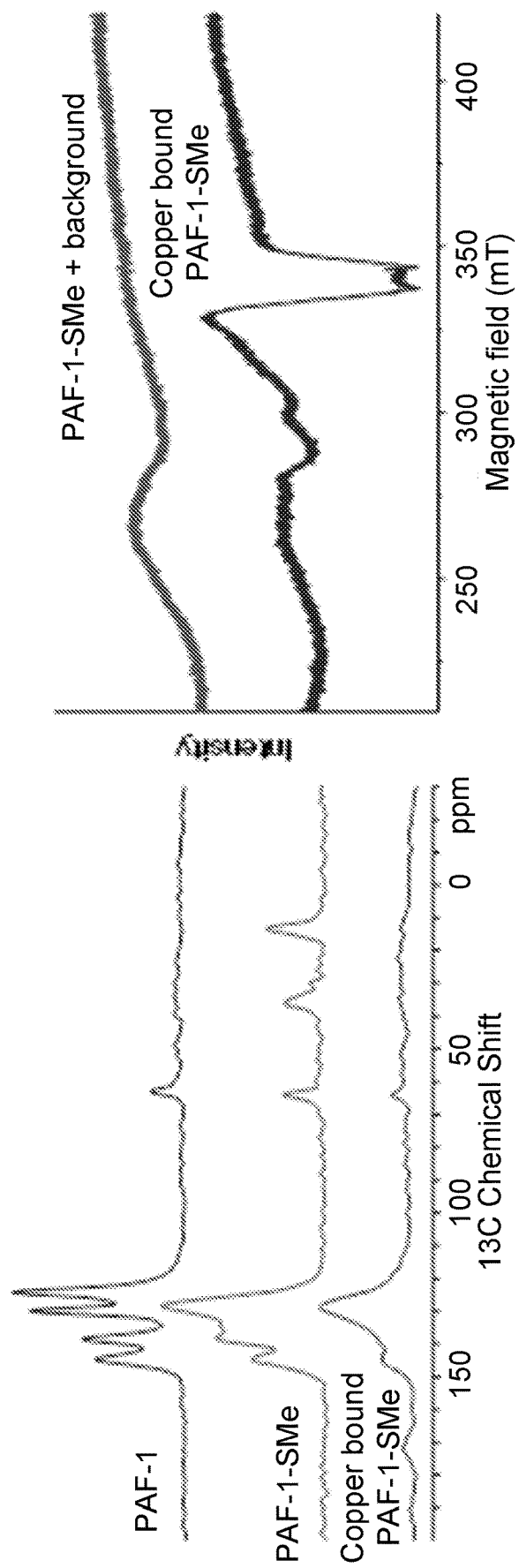
FIG. 9A illustrates Solid-state $^{13}C$ NMR spectra of PAF-1 and PAF-1-SMe and copper bound PAF-1-SMe.
FIG. 9B illustrates EPR spectra of PAF-1-SMe and copper bound PAF-1-SMe in accordance with some embodiments.

FIG. 9A illustrates Solid-state $^{13}$C NMR spectra of PAF-1 and PAF-1-SMe and copper bound PAF-1-SMe, FIG. 9B illustrates EPR spectra of PAF-1-SMe and copper bound PAF-1-SMe.

Figure 10A:
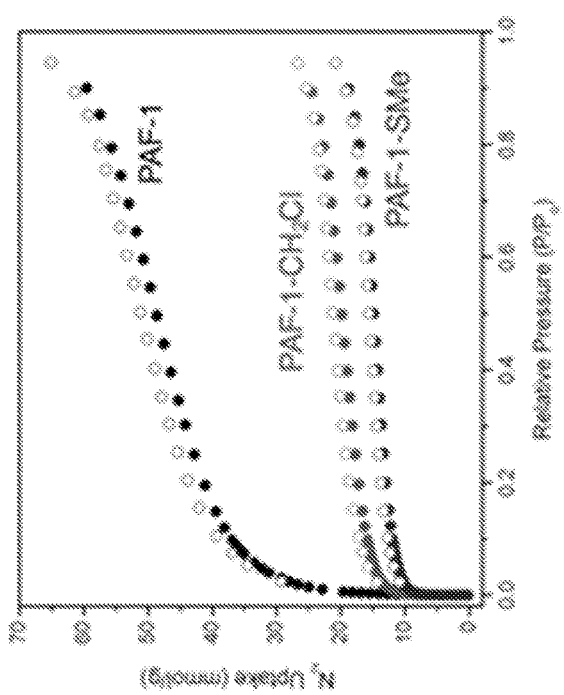
Figure 10C:
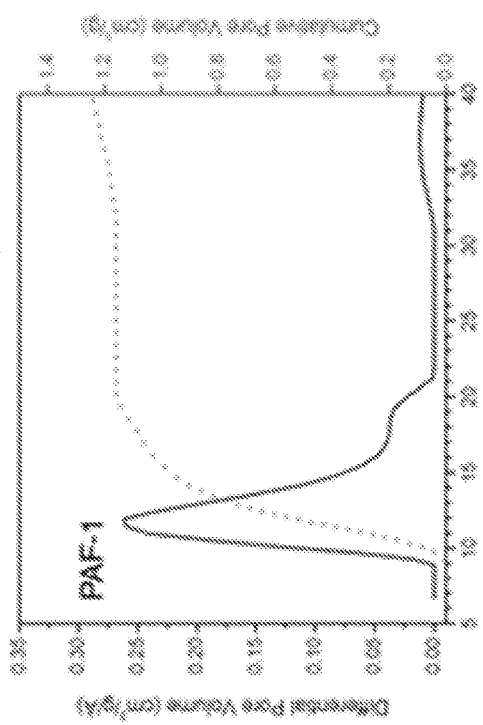

FIG. 10A illustrates N$_2$ sorption isotherms of PAF-1, PAF-1-CH$_2$Cl, and PAF-1-SMe at 77 K, (FIG. 10B) pore size distribution comparison of PAF-1 and PAF-1-SMe, (FIG. 10C) differential and cumulative pore volume graph of PAF-1, and (FIG. 10D) differential and cumulative pore volume graph of PAF-1-SMe.

Figure 11:
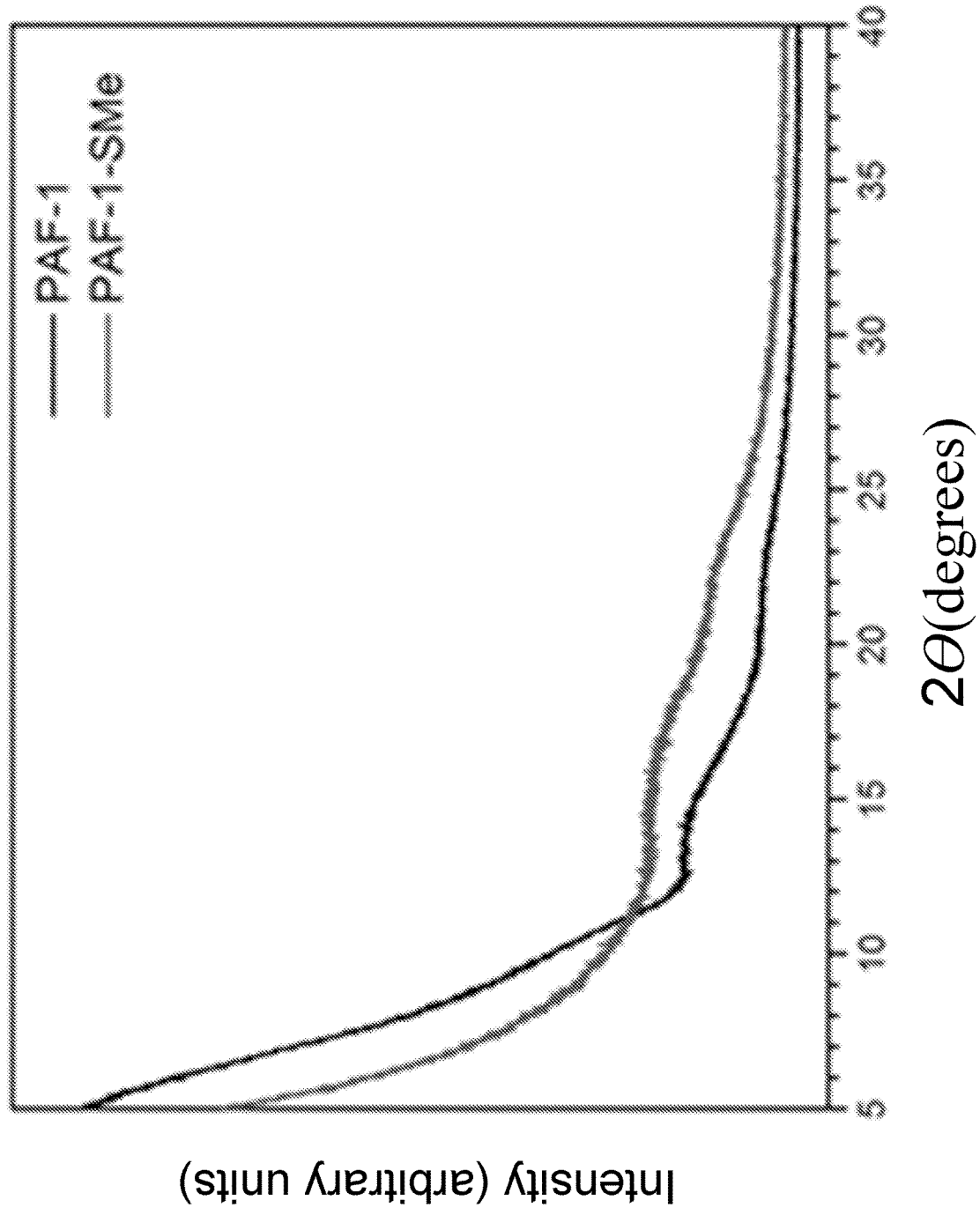
FIG. 11 illustrates powder X-ray diffraction patterns of PAF-1 and PAF-1-SMe, demonstrating the amorphous nature of both polymers.

FIG. 11 illustrates powder X-ray diffraction patterns of PAF-1 and PAF-1-SMe, demonstrating the amorphous nature of both polymers.

Figure 12:
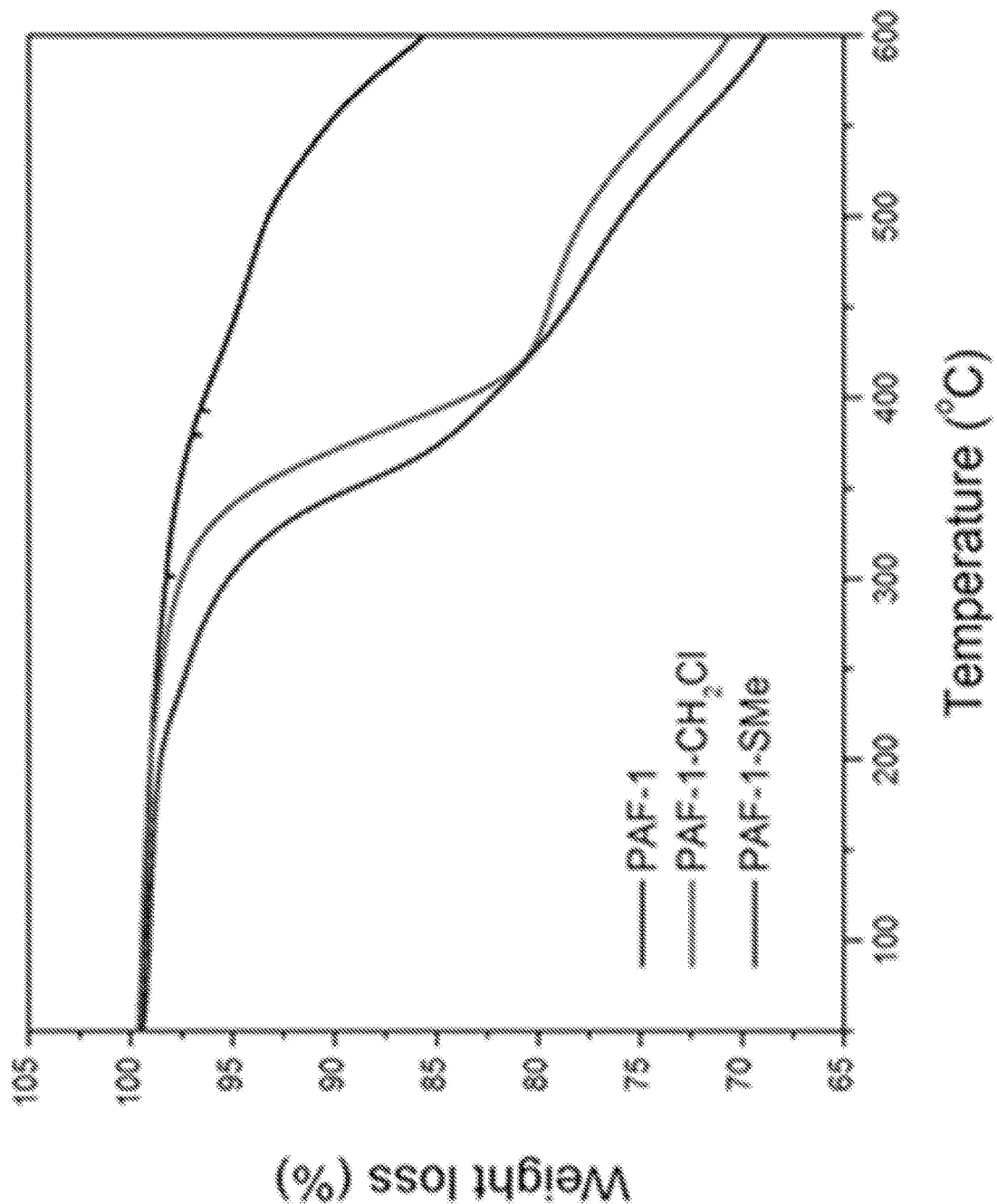
FIG. 12 illustrates thermogravimetric analysis of PAF-1, PAF-1-CH2Cl, and PAF-1-SMe.
Figure 13A:
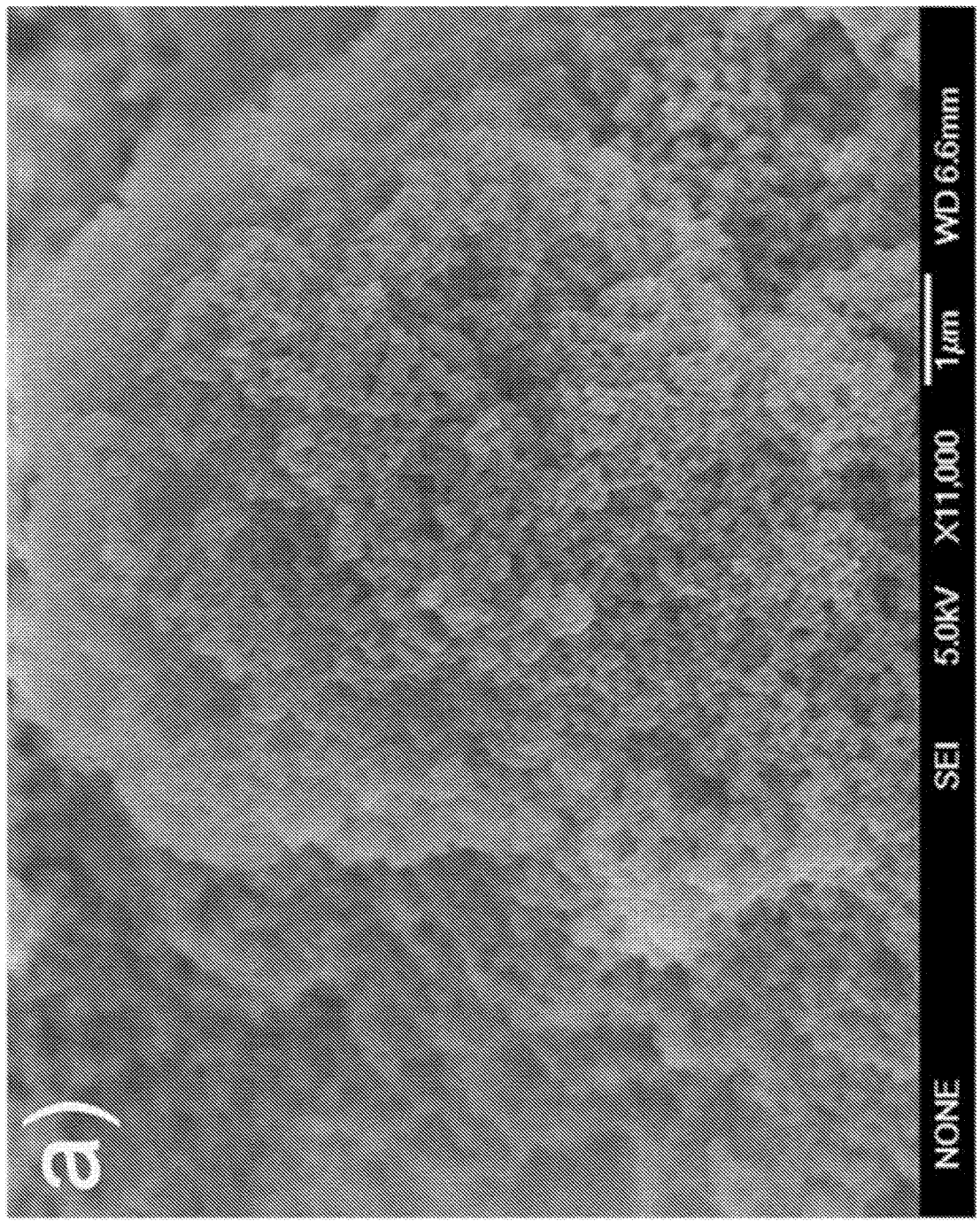
FIG. 13A illustrates SEM images of PAF-1 and FIG. 13B illustrates SEM images of PAF-1-SMe.
Figure 13B:
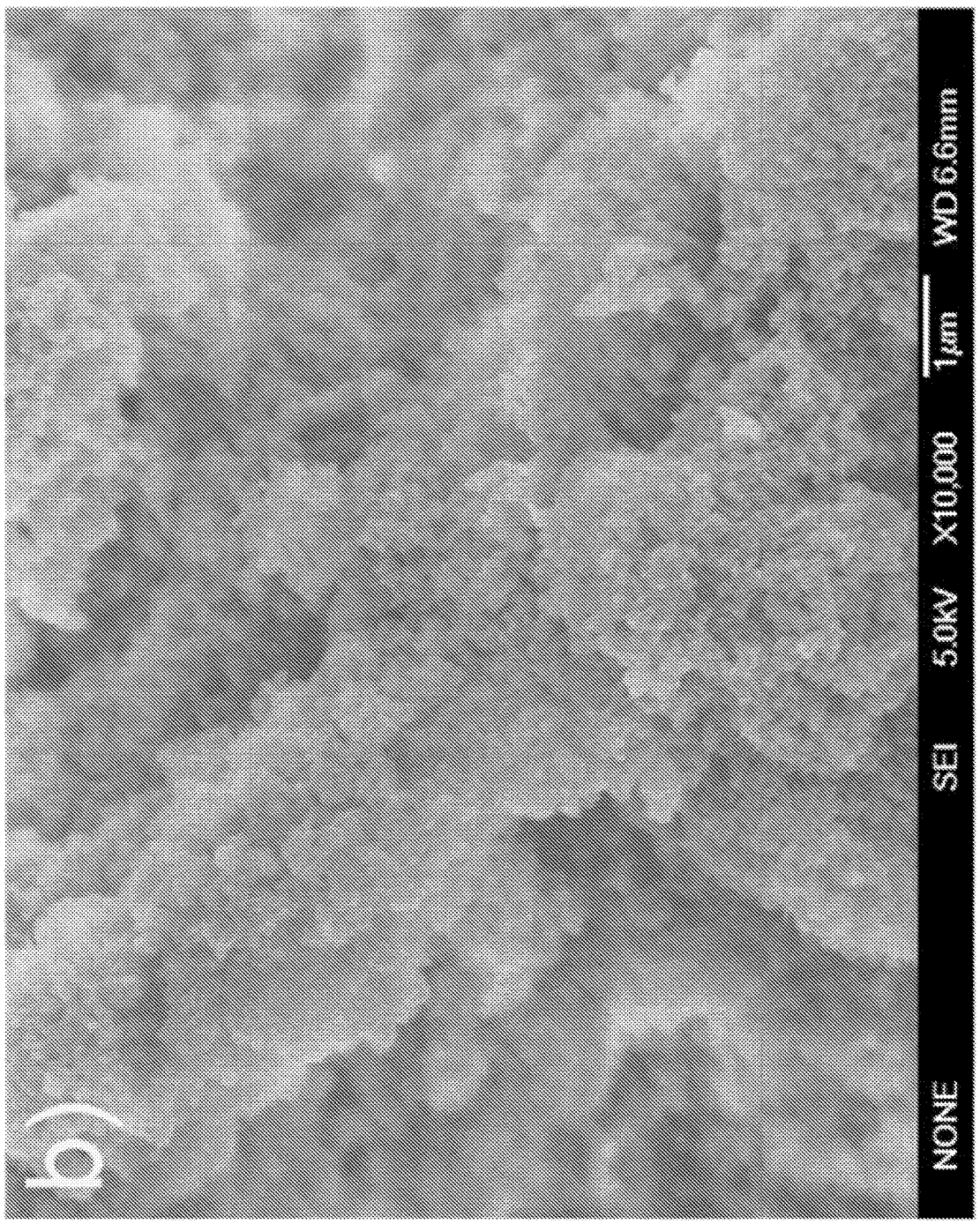

FIG. 12 illustrates Thermogravimetric analysis of PAF-1, PAF-1-CH2Cl, and PAF-1-SMe.

Determination of Distribution Coefficient (K$_d$) for Copper Uptake.

PAF-1-SMe (100.0 mg) was added to a column connected to a jar containing 1 L of 4.03 ppm CuCl$_2$ solution (100 mM HEPES buffer, pH 6.7). The copper solution was passed through PAF-1-SMe with flow rate of 0.5 mL/min. Subsequently, initial copper solution (C$_i$) and filtrate (C$_f$) were analyzed using ICP-MS (C$_i$=4.03 ppm; C$_f$=0.283 ppm) and used to determine the amount of copper captured by PAF-1-SMe. The amount of copper adsorbed by PAF-1-SMe was calculated by subtracting the residual copper concentration from the initial copper concentration. The following equation was used in order to determine the K$_d$ value:

$$K_d = \frac{(C_i - C_f)}{C_f} \times \frac{V}{m}$$

where C$_i$ is the initial metal ion concentration, C$_f$ is the final equilibrium metal ion concentration, V is the volume of the treated solution (mL) and m is the mass of sorbent used (g). See, Ebraheem and Hamdi, React. Funct. Polym. 1997, 34, 5-10; Boyd et al., 1947, J. Am. Chem. Soc. 69, 2836-2848; and (c) Kristiansen et al., 2011, J. Phys. Chem. C 115, 19260-19268, each of which is hereby incorporated by reference.

Adsorption Kinetics for Copper and Iron Removal.

A 10 mL aqueous CuCl$_2$ solution (10 ppm) or FeCl$_3$ solution (5 ppm in 100 mM HEPES buffer, pH 6.7) was added to an Erlenmeyer flask containing 2 mg of PAF-1-SMe. The mixture was stirred at room temperature for 8 h. During the stirring period, the mixture was filtered at intervals through a 0.45-mm membrane filter for all samples. The filtrates were analyzed using ICP-MS to determine the remaining copper concentration. The amount of copper adsorbed by PAF-1-SMe was calculated by subtracting the residual copper concentration from the initial copper concentration. The experimental data were fitted with a pseudo-second-order kinetic model using the following equation:

$$\frac{t}{q_t} = \frac{1}{k_2 q_e^2} + \frac{t}{q_e}$$

where k$_2$ is the pseudo-second-order rate constant of adsorption (g/mg·min) and q$_e$ is the amount of copper ion adsorbed at equilibrium (mg/g). The slope and intercept of the linear plot t/q$_t$ vs t yielded the values of q$_e$ and k$_2$, respectively.

Adsorption Isotherm.

Figure 16A:
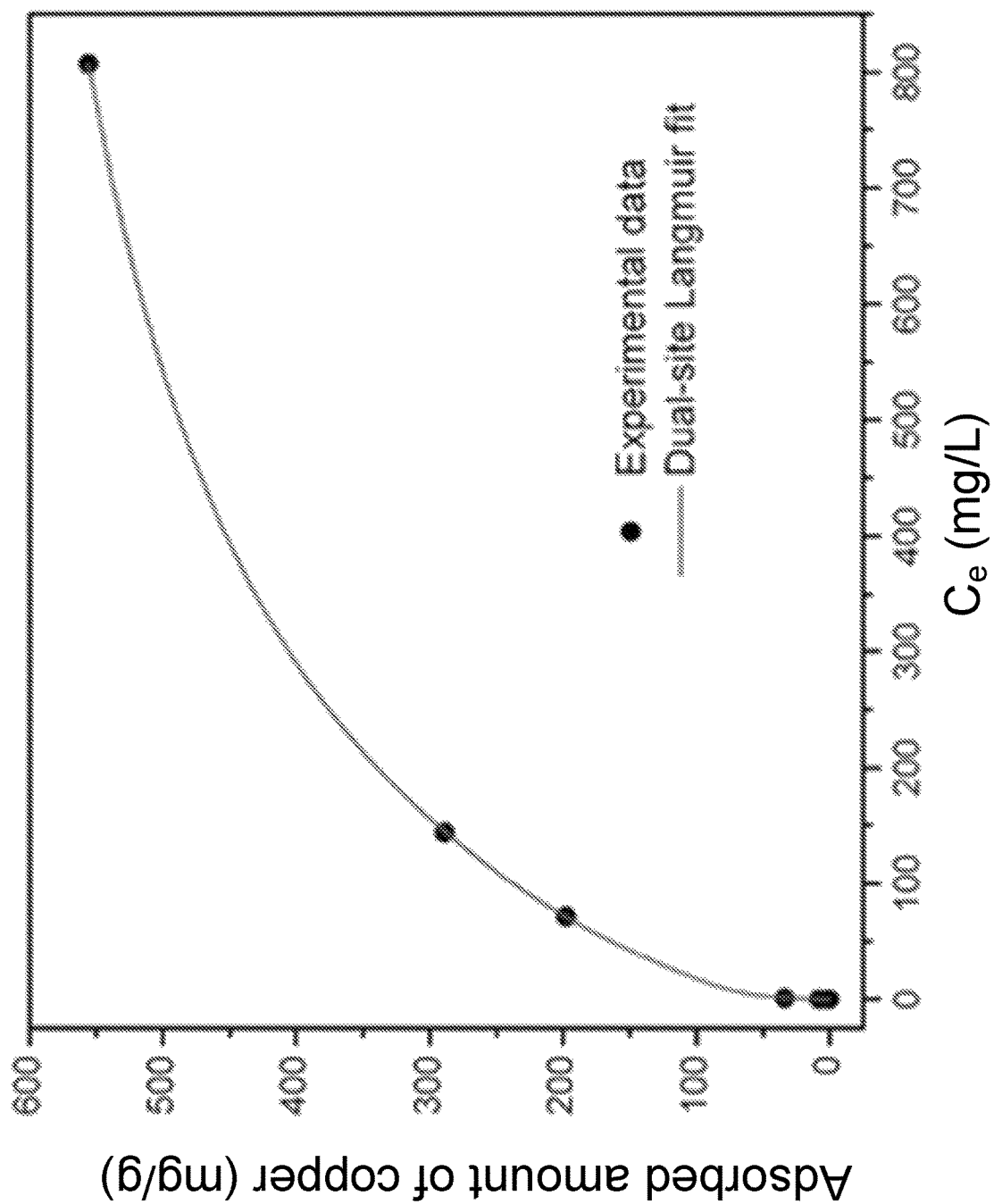
FIG. 16A, FIG. 16B and FIG. 16C illustrate adsorption isotherm of copper(II) uptake using PAF-1-SMe and dual-site Langmuir fit of the experimental data.
Figure 16B:
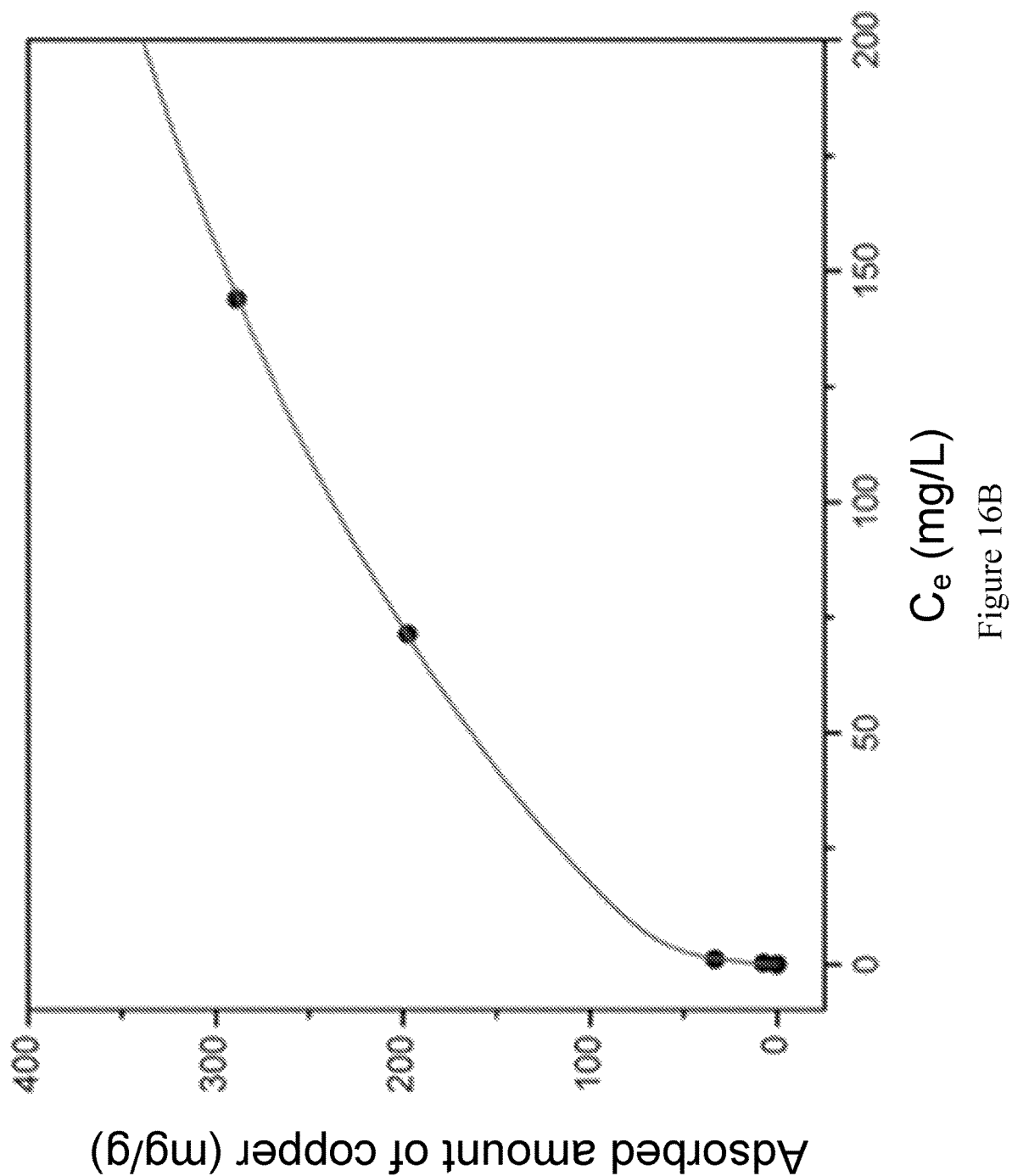
Figure 16C:
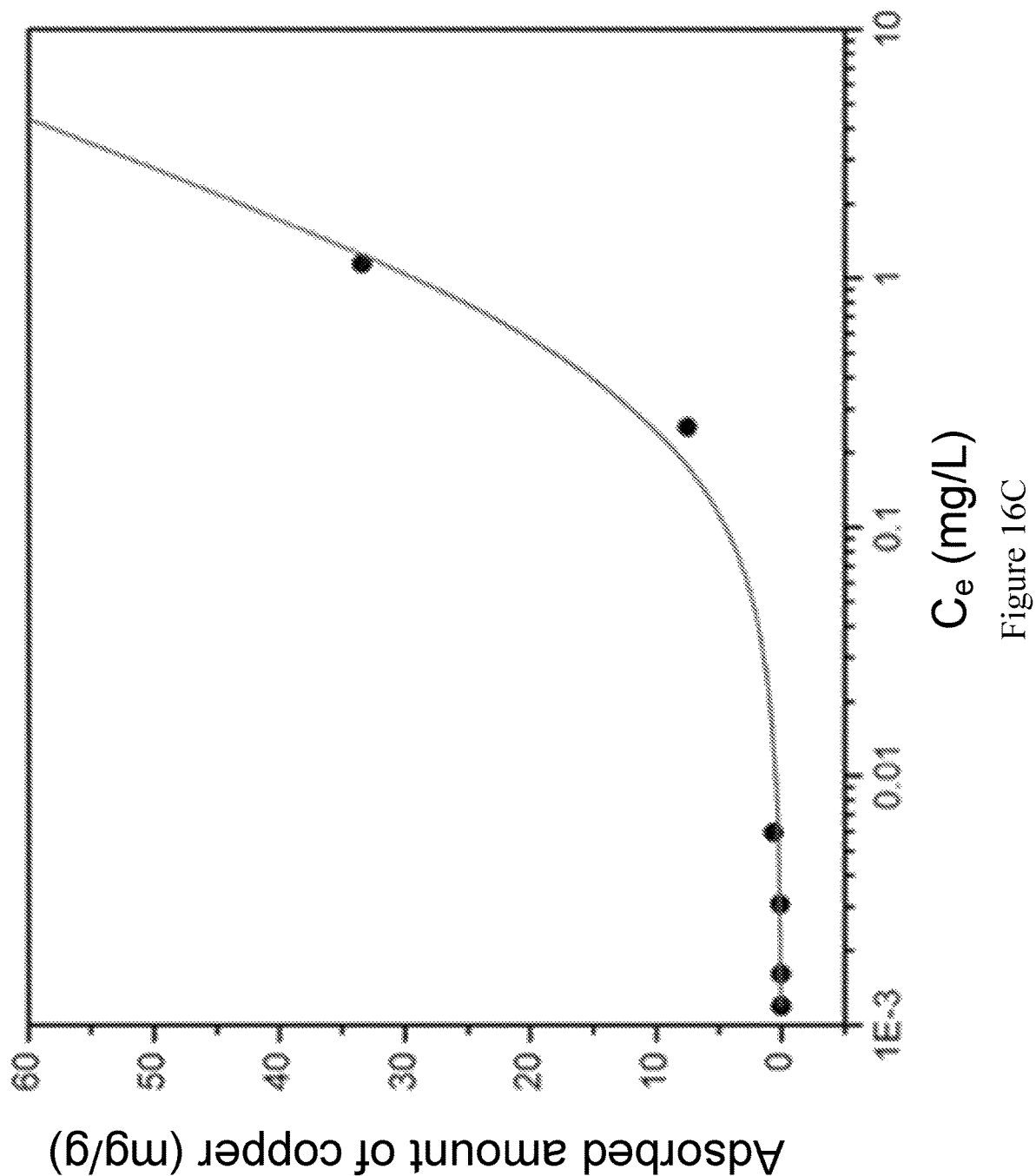
Figure 17A:
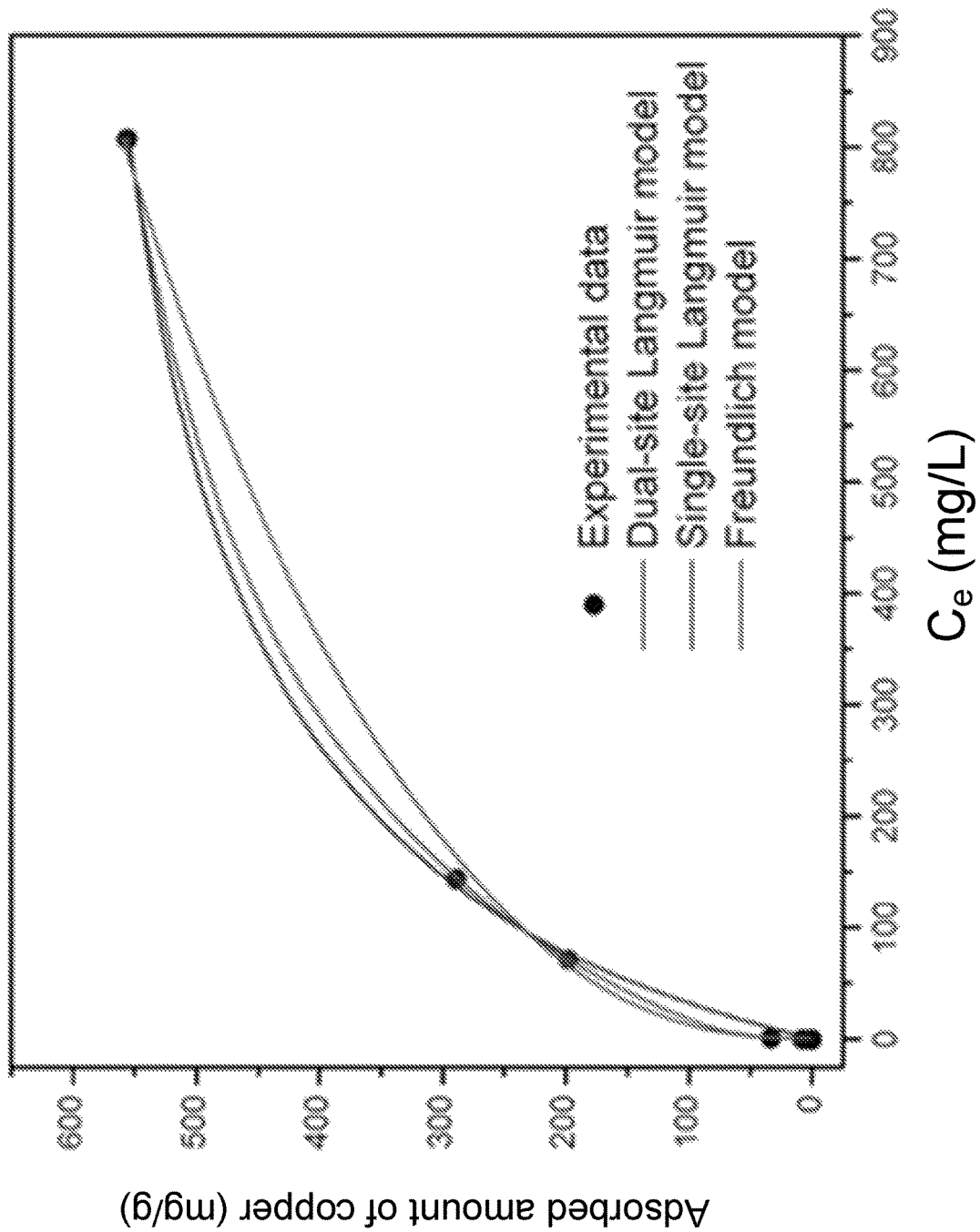
FIG. 17A, FIG. 17B and FIG. 17C illustrate the comparison of dual-site Langmuir, single-site Langmuir, and Freundlich models of PAF-1-SMe for fitting the experimental copper uptake data.
Figure 17B:
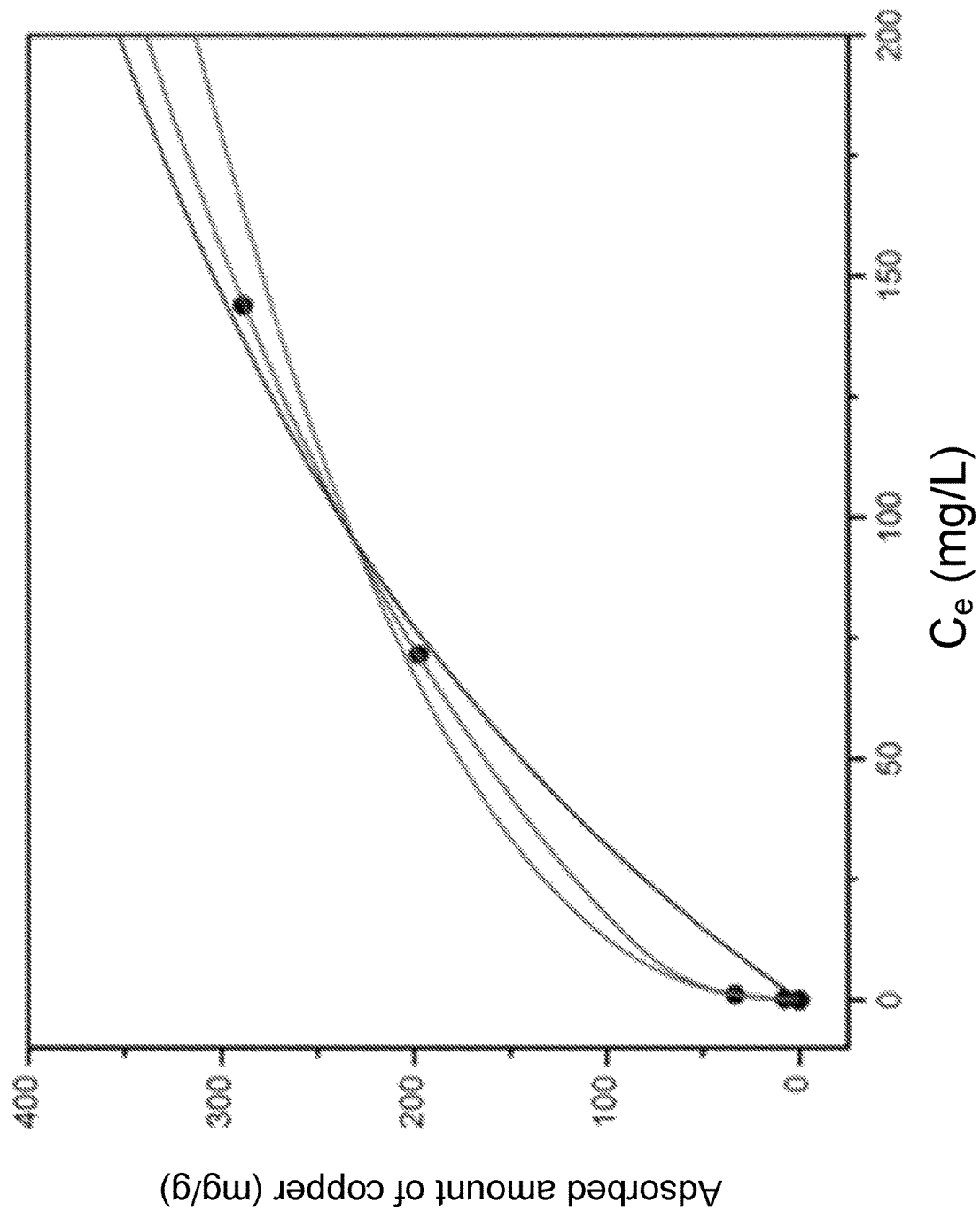
Figure 17C:
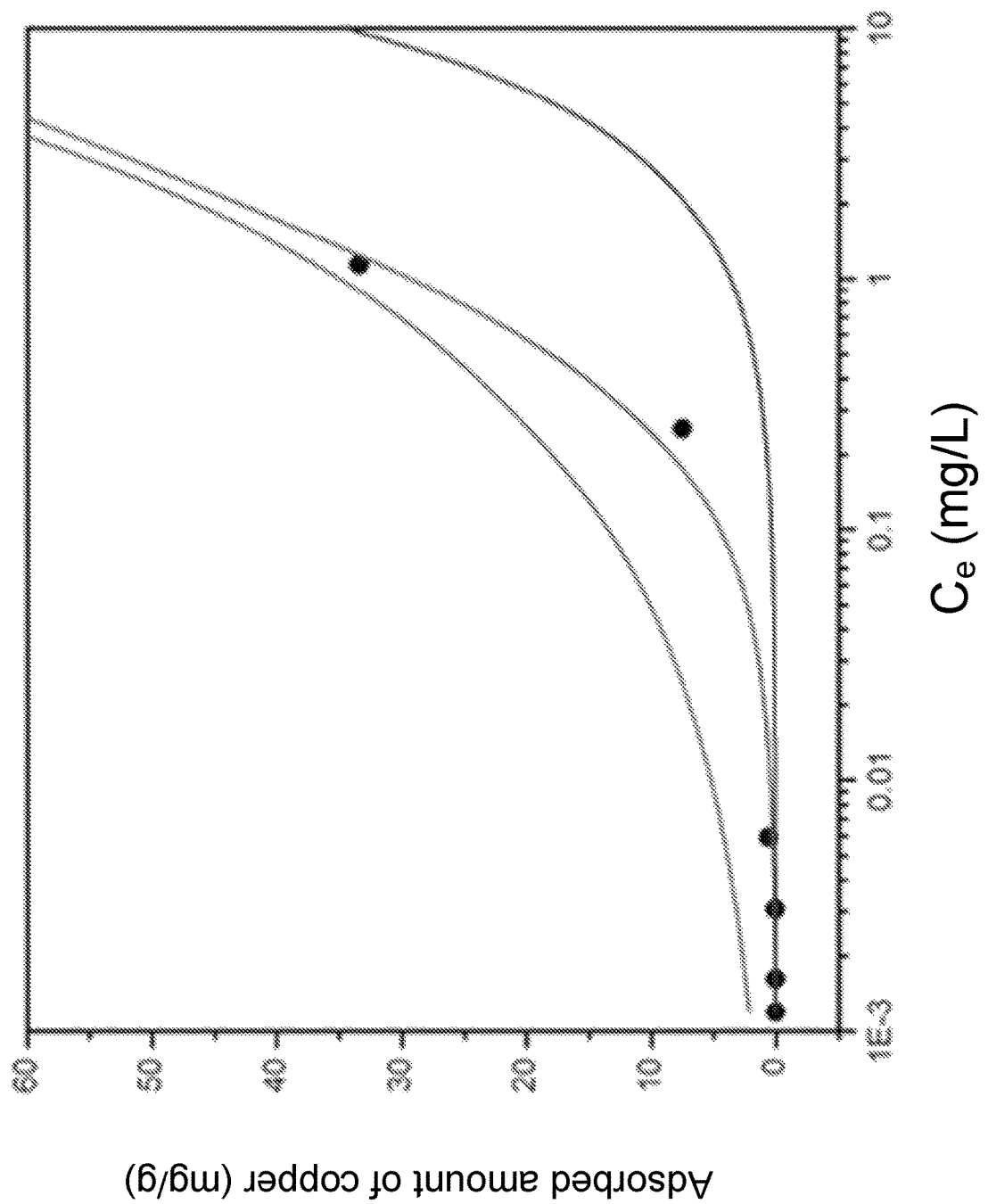
Figure 18:
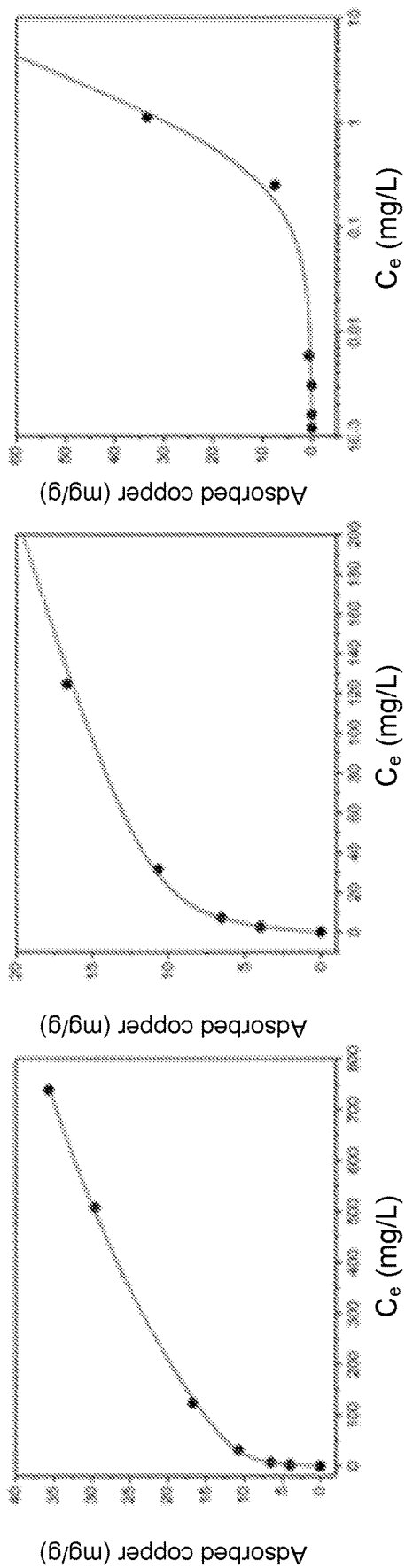
FIG. 18 illustrates Adsorption isotherm of copper(II) uptake using PAF-1-CH2Cl and dual-site Langmuir fit of the experimental data.

PAF-1-SMe (2.0 mg) was added to conical tubes containing 10 mL CuCl$_2$ solution (100 mM HEPES buffer, pH 6.7) with a wide range of copper concentrations. Each mixture was capped and stored in a shaker at room temperature overnight, and then filtered separately through a 0.45 mm membrane filter. The filtrates were analyzed by ICP-MS to determine the remaining copper content. The amount of copper adsorbed by PAF-1-SMe was calculated by subtracting the residual copper concentration from the initial copper concentration. The experimental copper uptake data were best fitted using a dual-site Langmuir model:

$$q_e = \frac{q_{sat,1} K_{L,1} C_e}{1 + K_{L,1} C_e} + \frac{q_{sat,2} K_{L,2} C_e}{1 + K_{L,2} C_e}$$

where q$_e$ is the adsorption capacity (mmol/g), C$_e$ is the equilibrium concentration of the metal ion (mg/L), q$_{sat,1}$ and q$_{sat,2}$ are saturation adsorption capacities (mmol/g) of two distinct adsorption sites, and K$_{L,1}$ and K$_{L,2}$ are the Langmuir constants (L/mg) that are related to the binding affinities of those adsorption sites (FIG. 16). For comparison, the experimental data were also fitted using commonly employed single-site Langmuir and Freundlich models, top and bottom equations below, respectively:

$$q_e = \frac{q_{sat} K_L C_e}{1 + K_L C_e}$$

$$q_e = K_F C_e^{1/n}$$

where K$_F$ is the binding energy constant (mg$^{1-(1/n)}$·L$^{1/n}$/g) and n is the Freundlich exponent (FIG. 17). Overall, the dual-site Langmuir model provided a good description of the experimental data, particularly in the low concentration region. The fitting parameters and correlation coefficients are summarized in Table 1. Nonlinear regression was used in fitting all models.

TABLE 1

Fitting parameters for three different models for the adsorption of copper(II) ions of PAF-1-SMe using nonlinear regression.

| Model | Dual-site Langmuir | Single-site Langmuir | Freundlich |
|---|---|---|---|
| Parameters | $q_{sat,1}$ = 67<br>$K_{L,1}$ = 0.68<br>$q_{sat,2}$ = 662<br>$K_{L,2}$ = 0.0035 | $q_{sat}$ = 682<br>$K_L$ = 0.0054 | $K_F$ = 34.99<br>n = 2.42 |
| $R^2$ | 0.9999 | 0.9961 | 0.9981 |

TABLE 2

Fitting parameters for dual-site Langmuir model for the adsorption of copper(II) ions of PAF-1-SMe using nonlinear regression.

| Model | Dual-site Langmuir |
|---|---|
| Parameters | $q_{sat,1}$ = 11<br>$K_{L,1}$ = 0.18<br>$q_{sat,2}$ = 72<br>$K_{L,2}$ = 0.007 |
| $R^2$ | 0.9992 |

Selectivity Studies.

2 mg of PAF-1-SMe was added into separate conical tubes containing 10 mL aqueous solution of $ZnCl_2$, $CaCl_2$, $MgCl_2$, NaCl, KCl, $NiCl_2$, $CoCl_2$, $MnCl_2$, or $NH_4Fe(SO_4)_2 \cdot 12H_2O$ (10 ppm each in 100 mM HEPES buffer, pH 6.7). The slurry was stored in a shaker at room temperature overnight, and then was filtered through a 0.45 mm membrane filter. The filtrates were analyzed using ICP-MS to determine the concentration of remaining metal ions. The amount of metal ion adsorbed by PAF-1-SMe was calculated by subtracting the residual copper concentration from the initial copper concentration.

Copper Uptake Studies in Biofluid Samples and its Colorimetric Detection:

Urine Collection.

To collect urine, 14-week-old Wilson's disease mice and controls from the background strain C57BLx129s6/svev were placed in Tecniplast metabolic cage systems for a period of 48 hours. During this period, the animals had access to water and food. The collected urine was centrifuged at 4,000×g for 5 min at 4° C. to remove debris or food particles, and then stored at −80° C. until further analysis.

Serum Collection.

2 L of porcine blood was purchased from Marin Sun Farm Inc. and was allowed to clot by leaving it undisturbed at room temperature for 30 minutes. The clot was removed by centrifuging at 3000×g for 15 minutes in a refrigerated centrifuge, and the resulting supernatant was transferred to 6 mL tubes from Becton Dickinson (BD Vacutainer REF 367815 6.0 mL). The samples were stored at −20° C. and freshly thawed before each experiment.

Copper Uptake in Biofluid Samples.

A 1 mL sample of the urine of 14-week-old mice from a murine model of Wilson's disease or heterozygous type controls was added to a 1.5 mL tube containing 2 mg of PAF-1-SMe. In case of serum, additional copper salts (2, 5, 10 ppm) were added in 4 mL of serum to simulate Wilson's disease. See Bandmann et al., 2015, Lancet 14, 103-113, which is hereby incorporated by reference.

Moreover, as serum contains ca. 4-fold higher levels of iron compared to copper (See, Afsana et al., 2004, Biosci. Biotechnol. Biochem. 68, 584-592; and Ranganathan et al., 2011, Blood 118, 3146-3152, each of which is hereby incorporated by reference), 1 mM acetohydroxyamic acid (AHA) as iron chelator was additionally added into serum (See, Farkas et al., 1999, Polyhedron 18, 2391-2398; (b) Witte et al., 2000, Free Radic. Biol. Med. 28, 693-700; and (c) Maekawa and Koshijima, 1990, J. Appl. Polym. Sci. 40, 1601-1613, each of which is hereby incorporated by reference). PAF-1-SMe (2 mg) was added into each urine and serum sample, and biofluid samples with/without PAF-1-SMe were kept in a shaker at room temperature for overnight, filtered through 0.45 mm membrane filters, and analyzed by ICP-MS to determine remaining copper content. The amount of copper adsorbed by PAF-1-SMe was calculated by subtracting the residual copper concentration from the initial copper concentration.

Colorimetric Detection.

PAF-1-SMe applied to heterozygous and Wilson's disease urine specimens and serum samples was dried open to air overnight. Before treatment with 8-hydroxyquinoline (8-HQ), dried PAF-1-SMe was washed by adding 1 mL of DMSO and remove DMSO by immediate filtration. Subsequently, 1 mM 8-HQ in DMSO (1 mL) was added to the washed PAF-1-SMe and shaken three times. The liquid was filtered through a 0.45 mm membrane filter and transferred into 1 cm×0.5 cm quartz cuvette (1.4-mL volume, Starna). The formation of complex between 8-HQ and copper extracted from PAF-1-SMe was monitored using a Varian Cary 50 spectrophotometer.

Detection limit of 8-HQ was measured in DMSO, in serum by adding external copper salt (1, 2, and 5 ppm of 1 mL of serum), and in urine by adding external copper salt (1.5, 3, and 5 ppm in 200 μL of urine sample). PAF-1-SMe (2 mg) was stored in each sample overnight in a shaker and dried after filtration. Dried PAF-1-SMe was washed by adding 1 mL of DMSO, and 1 mM 8-HQ in DMSO (1 mL) was added into washed PAF-1-SMe. The absorbance at 410 nm of each samples was plotted against initial copper concentrations. The detection limit of 8-HQ was calculated by the three-sigma method 3σ/k as 186 ppb in DMSO, 756 ppb in serum samples, and 552 ppb for urine samples, respectively.

CONCLUSION

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

We claim:

1. A method of selective detection of a concentration of a first metal ion species in a subject, the method comprising:
   a) obtaining a biofluid sample from the subject;
   b) exposing the biofluid sample to a functionalized porous aromatic polymer, wherein the functionalized porous aromatic polymer selectively captures and concentrates the first metal ion species from the biofluid sample;
   c) washing the biofluid sample from the porous aromatic polymer;
   d) exposing the washed functionalized porous aromatic polymer to a solution comprising a colorimetric indicator that extracts the first metal ion species from the washed functionalized porous aromatic polymer thereby changing a color of the solution as a function of an amount of the first metal ion species in the washed functionalized porous aromatic polymer; and e) spectroscopically determining the concentration of the first metal ion species in the subject from the color of the solution.

2. The method of claim 1, wherein the biofluid sample is urine, serum, whole blood, saliva, tears, sweat, breast milk, mucus, blister fluid, or cyst fluid.

3. The method of claim 1, wherein the first metal ion species is copper, and the functionalized porous aromatic polymer is functionalized with an alkyl thioether, a dialkyl thioether, 2,5-dithiahexane, 3,4-dithiahexane, 4,5-dithiahexane, (2-methoxyethyl)(methyl)sulfane, (2-methoxyethyl)(methyl)sulfane, 3-(methylthio)propanoic acid, ethylglycine, N-hydroxy-2-(methyl amino)acetamide, 2-thiopentane, N-hydroxyacetamide, or 2-methylhydrazine-1-carbothioamide.

4. The method of claim 1, wherein the first metal ion species is copper and the method further comprises pretreating the biofluid sample prior to the exposing b) with a chelator for a second metal ion species.

5. The method of claim 4, wherein the second metal ion species is iron and the chelator is acetohydroxamic acid, desferoxamine (DFO), 2,2'-bypyridyl, 1,10-phenantholine, or ethylenediaminetetraacetic acid (EDTA).

6. The method of claim 1, wherein the first metal ion species is copper and the functionalized porous aromatic polymer is formed from the monomer of Formulas (I), (II), (III) or (IV):

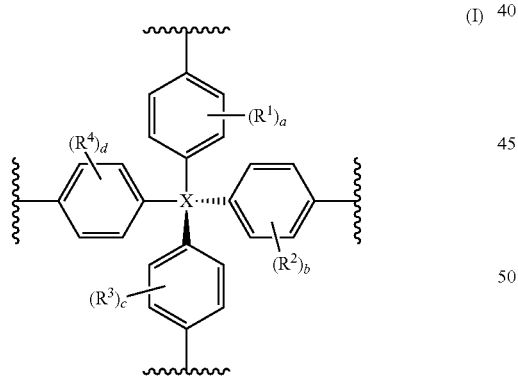

(I)

(II)

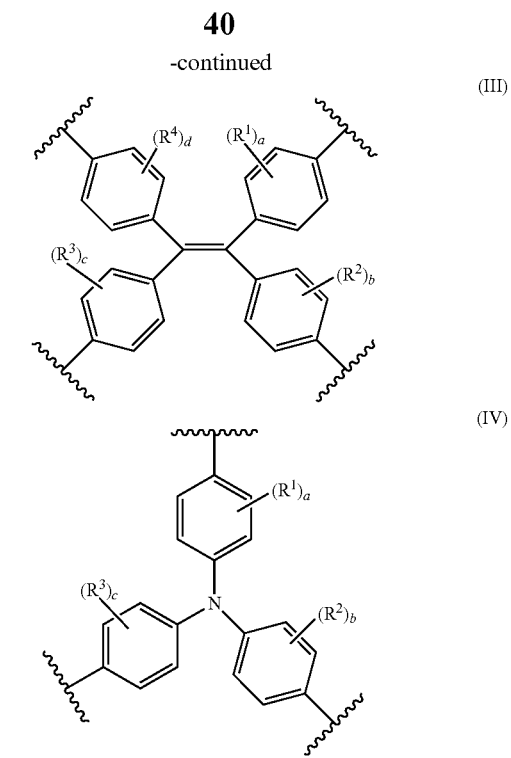

(III)

(IV)

wherein,

X is selected from C, Si, and a three-dimensional polycyclic cycloalkyl moiety, $R^1$, $R^2$, $R^3$ and $R^4$ are independently selected from an alkyl thioether, a dialkyl thioether, 2,5-dithiahexane, 3,4-dithiahexane, 4,5-dithiahexane, (2-methoxyethyl)(methyl)sulfane, (2-methoxyethyl)(methyl)sulfane, 3-(methylthio)propanoic acid, ethylglycine, N-hydroxy-2-(methylamino)acetamide, 2-thiopentane, N-hydroxyacetamide and 2-methylhydrazine-1-carbothioamide, and the indeces a, b, c and d are members independently selected from the integers 0, 1, 2, 3, and 4, such that when a, b, c, or d is greater than 1, each $R^1$, $R^2$, $R^3$ and $R^4$, respectively, is independently selected.

7. The method of claim 1, wherein the first metal ion species is copper, and the functionalized porous aromatic polymer is a copolymer formed from a first monomer of Formula (I), (II), (III) or (IV) of claim 6 and a second monomer according to Formula (V):

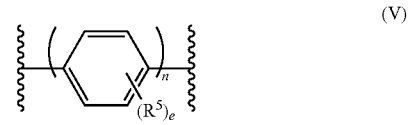

(V)

wherein, $R^5$ is a member selected from H, an alkyl thioether, a dialkyl thioether, 2,5-dithiahexane, 3,4-dithiahexane, or 4,5-dithiahexane, (2-methoxyethyl)(methyl)sulfane, (2-methoxyethyl)(methyl)sulfane, 3-(methylthio)propanoic acid, ethylglycine, N-hydroxy-2-(methylamino)acetamide, 2-thiopentane, N-hydroxyacetamide and 2-methylhydrazine-1-carbothioamide, n is 1, 2, or 3, e is an integer selected from 0, 1, 2, 3, and 4, such that when e is greater than 1, each $R^5$ is independently selected, and said first monomer and said second monomer are covalently bound in said copolymer.

8. The method of claim 1, wherein the metal ion species is copper and the functionalized porous aromatic polymer is according to Formula (VI), (VII), (VIII), or (IX):

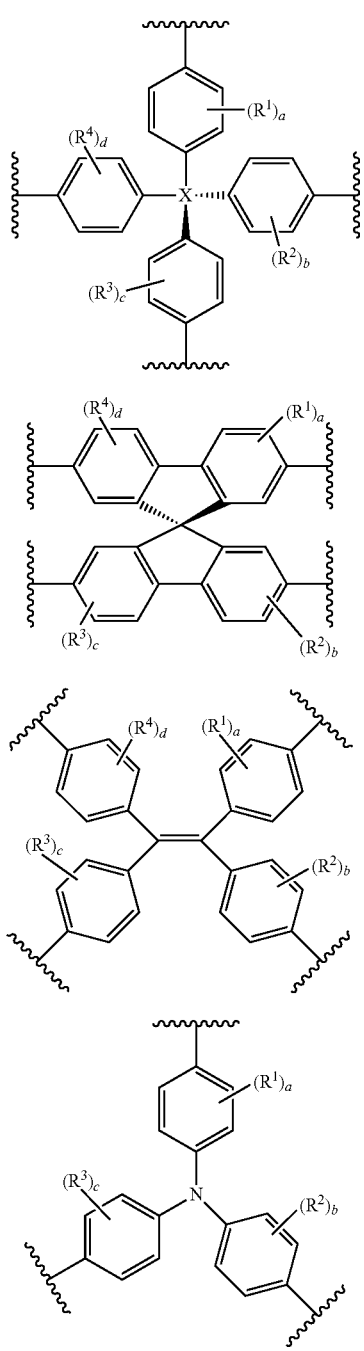

wherein,

X is selected from C, Si, and a three-dimensional polycyclic cycloalkyl moiety; and $R^1$, $R^2$, $R^3$ and $R^4$ are each independently selected from Formula (X) or (XI)

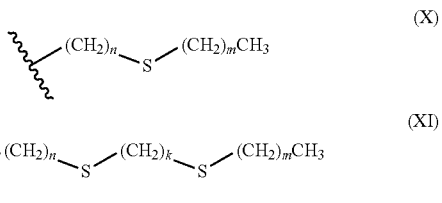

wherein, n is a zero or positive integer, m is zero or a positive integer, k is a positive integer, the indeces a, b, c and d are members independently selected from the integers 0, 1, 2, 3, and 4, such that when a, b, c, or d is greater than 1, each $R^1$, $R^2$, $R^3$ and $R^4$, respectively, is independently selected.

9. The method of claim 1, wherein the first metal ion species is copper and wherein the functionalized porous aromatic polymer is a copolymer formed from a first monomer of Formula (VI), (VII), (VIII) or (IX) of claim 8 and a second monomer of Formula (XII):

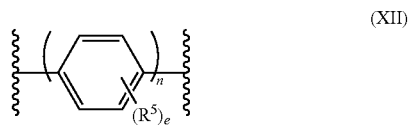

wherein, $R^5$ is a member selected from H, an alkyl thioether, a dialkyl thioether, 2,5-dithiahexane, 3,4-dithiahexane, 4,5-dithiahexane, (2-methoxyethyl)(methyl)sulfane, (2-methoxyethyl)(methyl)sulfane, 3-(methylthio)propanoic acid, ethylglycine, N-hydroxy-2-(methylamino) acetamide, 2-thiopentane, N-hydroxyacetamide and 2-methylhydrazine-1-carbothioamide, e is an integer selected from 0, 1, 2, 3, and 4, such that when e is greater than 1, each $R^5$ is independently selected, and said first monomer and said second monomer are covalently bound in said copolymer.

10. The method of any one of claims 1-8, wherein the first metal ion species is copper, and the colorimetric indicator comprises 8-hydroxyquinoline, 2,2'-bipyridine, or 1,10-phenanthroline.

11. The method of claim 1, wherein the first metal ion species is copper, and the spectroscopically determining e) determines whether the subject has Wilson's disease from the color of the solution.

12. The method of claim 1, wherein the first metal ion species is iron, and the functionalized porous aromatic polymer is according to Formula (XIII), (XIV), (XV), or (XVI):

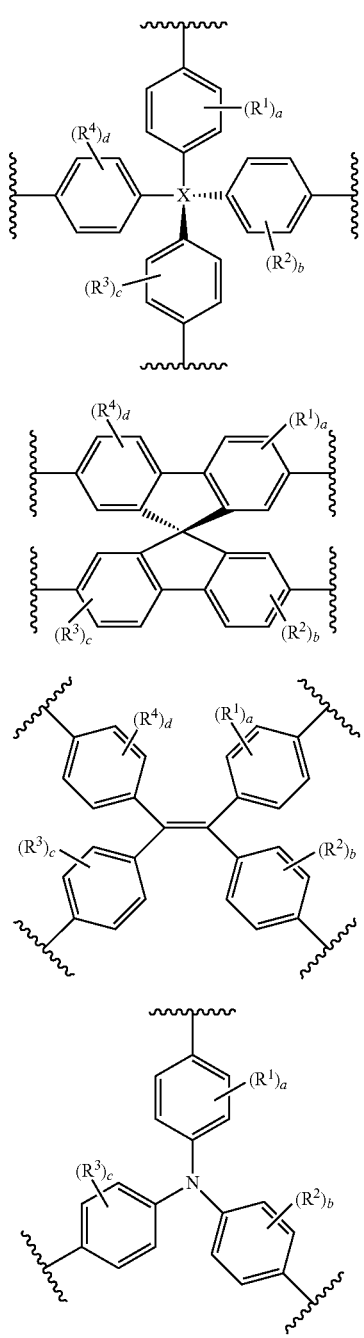

(XIII)

(XIV)

(XV)

(XVI)

wherein,
X is selected from C, Si, and a three-dimensional polycyclic cycloalkyl moiety;
$R^1$, $R^2$, $R^3$ and $R^4$ are independently selected from Formula (XVII) or (XVIII)

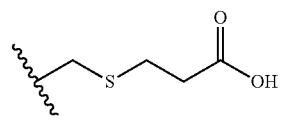

(XVII)

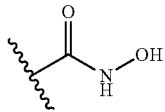

(XVIII)

wherein,
the indeces a, b, c and d are members independently selected from the integers 0, 1, 2, 3, and 4, such that when a, b, c, or d is greater than 1, each $R^1$, $R^2$, $R^3$ and $R^4$, respectively, is independently selected.

13. The method of claim 1, wherein
the first metal ion species is iron, and
the functionalized porous aromatic polymer is a copolymer formed from a first monomer of Formula (XIII), (XIV), (XV) or (XVI) of claim 12 and a second monomer according to Formula (XIX):

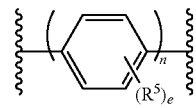

(XIX)

wherein,
$R^5$ is independently selected from Formula (XX) or (XXI)

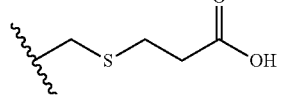

(XX)

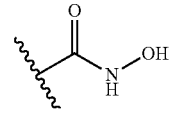

(XXI)

e is an integer selected from 0, 1, 2, 3, and 4, such that when e is greater than 1, each $R^5$ is independently selected, and
said first monomer and said second monomer are covalently bound in said copolymer.

14. The method of claim 1, wherein
the first metal ion species is iron or copper, and
the colorimetric indicator is according to Formula (XXII):

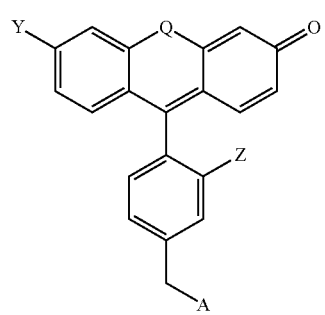

(XXII)

wherein,
Q=O, Si(Me)$_2$, or C(Me)$_2$,
Y=—OH, morpholine, piperidine, pyrrolidine, or a piperazine derivative,
Z=—CH$_3$, —CF$_3$, or —COOH, and
A is a metal ion acceptor.

15. The method of claim 14, wherein
the first metal ion is copper, and
A is 3,6,12,15-tetrathia-9-monoazaheptadecane.

16. A method of detecting copper in a subject, the method comprising:
a) obtaining plasma or urine from the subject;
b) exposing the plasma or urine to a functionalized porous aromatic polymer, wherein the functionalized porous aromatic polymer selectively captures and concentrates copper from the plasma or urine;
c) washing the plasma or urine from the functionalized porous aromatic polymer;
d) exposing the washed functionalized porous aromatic polymer to a solution comprising a colorimetric indicator that extracts the copper from the washed functionalized porous aromatic polymer thereby changing a color of the solution as a function of an amount of the copper in the washed functionalized porous aromatic polymer; and
e) spectroscopically determining, after the exposing d), the concentration of the copper in the subject from the color of the solution by measuring a characteristic absorption wavelength of a complex between copper and the colorimetric indicator.

17. The method of claim 16, wherein the functionalized porous aromatic polymer is formed from the monomer of Formula (XXIII):

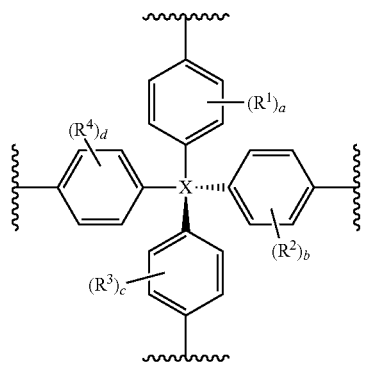

(XXIII)

wherein,

X is carbon;

$R^1$, $R^2$, $R^3$ and $R^4$ are independently selected from Formula (XXIV) or (XXV)

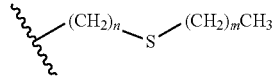

(XXIV)

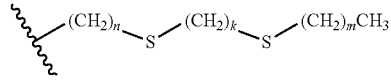

(XXV)

wherein, n is 1, 2 or 3, m is 1 or 2, k is 1, 2 or 3, and the indeces a, b, c and d are members independently selected from the integers 0, 1, 2, 3, and 4, such that when a, b, c, or d is greater than 1, each $R^1$, $R^2$, $R^3$ and $R^4$, respectively, is independently selected.

18. The method of claim 17, wherein the method further comprises pretreating the biofluid sample prior to the exposing b) with a chelator for iron.

19. The method of claim 18, wherein the chelator is acetohydroxamic acid, desferoxamine (DFO), or 2,2'-bypyridyl.

* * * * *